US012260555B2

(12) United States Patent
Jordan

(10) Patent No.: US 12,260,555 B2
(45) Date of Patent: Mar. 25, 2025

(54) POST OPERATIVE IMPLANTATION SITE MONITORING AND MEDICAL DEVICE PERFORMANCE

(71) Applicant: Medtronic, Inc., Minneapolis, MN (US)

(72) Inventor: Michael Erich Jordan, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 563 days.

(21) Appl. No.: 17/217,632

(22) Filed: Mar. 30, 2021

(65) Prior Publication Data

US 2021/0343017 A1    Nov. 4, 2021

Related U.S. Application Data

(60) Provisional application No. 63/018,047, filed on Apr. 30, 2020.

(51) Int. Cl.
*G16H 30/00*     (2018.01)
*A61B 5/33*      (2021.01)
(Continued)

(52) U.S. Cl.
CPC .............. *G06T 7/0016* (2013.01); *A61B 5/33* (2021.01); *G06T 7/337* (2017.01); *G16H 15/00* (2018.01);
(Continued)

(58) Field of Classification Search
USPC .............. D24/158–186; 600/300–595, 1–29; 604/890.1–892.1, 28; 704/1–275;
(Continued)

(56) References Cited

U.S. PATENT DOCUMENTS 5,321,618 A    6/1994   Gessman
6,108,635 A *  8/2000   Herren ................... G16H 10/60
                                                    600/300

(Continued)

FOREIGN PATENT DOCUMENTS

CN       103961722 A     8/2014
KR    20160023849 A      3/2016
(Continued)

OTHER PUBLICATIONS

Wollowick Noah D; Systems and Methods for Intra-Operative Image Analysis; 2017 (Year: 2017).*

(Continued)

*Primary Examiner* — Marcellus J Augustin
(74) *Attorney, Agent, or Firm* — Shumaker & Sieffert, P.A.

(57) ABSTRACT

Techniques for remote monitoring of a patient and corresponding medical device(s) are described. The remote monitoring comprises identifying a first set of images that represent a particular location of a body of a patient in which at least one component of an implantable medical device (IMD) coincides, determining a projection of alteration characteristics of the particular location of the body, identifying a second set of images, determining a second set of alteration characteristics, comparing the second set of alteration characteristics to the projection, and identifying a potential abnormality at the particular location of the body.

22 Claims, 23 Drawing Sheets

(51) Int. Cl.
| | |
|---|---|
| *G06T 7/00* | (2017.01) |
| *G06T 7/33* | (2017.01) |
| *G16H 15/00* | (2018.01) |
| *G16H 30/20* | (2018.01) |
| *G16H 30/40* | (2018.01) |
| *G16H 50/30* | (2018.01) |
| *G16H 50/50* | (2018.01) |
| *G16H 50/70* | (2018.01) |
| *G16H 40/40* | (2018.01) |
| *G16H 40/67* | (2018.01) |
| *G16H 50/20* | (2018.01) |

(52) U.S. Cl.
CPC ............ *G16H 30/20* (2018.01); *G16H 30/40* (2018.01); *G16H 50/30* (2018.01); *G16H 50/50* (2018.01); *G16H 50/70* (2018.01); *G06T 2207/30004* (2013.01); *G16H 40/40* (2018.01); *G16H 40/67* (2018.01); *G16H 50/20* (2018.01)

(58) Field of Classification Search
USPC ...................................................... 901/1–50
See application file for complete search history.

(56) References Cited

U.S. PATENT DOCUMENTS

| | | |
|---|---|---|
| 6,442,432 B2 | 8/2002 | Lee |
| 6,497,655 B1 | 12/2002 | Linberg et al. |
| 8,301,254 B2 | 10/2012 | Mosesov et al. |
| 9,615,744 B2 | 4/2017 | Denison et al. |
| 10,729,502 B1 | 8/2020 | Wolf et al. |
| 11,074,760 B2 | 7/2021 | Bidne et al. |
| 11,141,115 B2 | 10/2021 | Benson et al. |
| 2002/0032470 A1 | 3/2002 | Linberg |
| 2004/0116981 A1 | 6/2004 | Mazar |
| 2005/0065555 A1 | 3/2005 | Er |
| 2005/0171411 A1 | 8/2005 | KenKnight et al. |
| 2005/0192844 A1 | 9/2005 | Esler et al. |
| 2005/0228693 A1 | 10/2005 | Webb et al. |
| 2005/0283198 A1 | 12/2005 | Haubrich et al. |
| 2006/0189869 A1 | 8/2006 | Sela et al. |
| 2007/0203538 A1 | 8/2007 | Stone et al. |
| 2007/0276309 A1 | 11/2007 | Xu et al. |
| 2008/0051638 A1 | 2/2008 | Iliff |
| 2008/0071161 A1* | 3/2008 | Jaeb ........................ A61B 5/107 600/407 |
| 2008/0097793 A1 | 4/2008 | Dicks et al. |
| 2008/0262323 A1 | 10/2008 | Gerber et al. |
| 2008/0317195 A1 | 12/2008 | Kobayashi et al. |
| 2009/0088620 A1 | 4/2009 | Zagorchev et al. |
| 2010/0022990 A1 | 1/2010 | Karpowicz et al. |
| 2010/0036209 A1 | 2/2010 | Ferren et al. |
| 2010/0185064 A1 | 7/2010 | Bandic et al. |
| 2010/0316259 A1 | 12/2010 | Liu et al. |
| 2010/0324936 A1 | 12/2010 | Vishnubhatla et al. |
| 2011/0117025 A1 | 5/2011 | Dacosta et al. |
| 2012/0044070 A1 | 2/2012 | Putrino |
| 2012/0232339 A1 | 9/2012 | Csiky |
| 2012/0274804 A1 | 11/2012 | Tanabe |
| 2013/0012835 A1* | 1/2013 | Chono ................... A61B 8/467 600/587 |
| 2013/0053657 A1 | 2/2013 | Ziarno et al. |
| 2014/0059237 A1 | 2/2014 | Pittman et al. |
| 2014/0088990 A1 | 3/2014 | Nawana et al. |
| 2014/0122120 A1 | 5/2014 | Doudian |
| 2014/0276928 A1 | 9/2014 | Vanderpool et al. |
| 2014/0378964 A1 | 12/2014 | Pearson |
| 2015/0089590 A1 | 3/2015 | Krishnan et al. |
| 2015/0104085 A1 | 4/2015 | Schilling et al. |
| 2015/0112705 A1* | 4/2015 | Neville ................. G16H 50/30 705/2 |
| 2015/0133945 A1 | 5/2015 | Dushyant et al. |
| 2015/0150457 A1 | 6/2015 | Wu et al. |
| 2015/0286787 A1 | 10/2015 | Chen et al. |
| 2016/0069919 A1 | 3/2016 | Holmes et al. |
| 2016/0192878 A1 | 7/2016 | Hunter |
| 2016/0228034 A1* | 8/2016 | Gluncic ................. G06T 7/0012 |
| 2016/0310031 A1 | 10/2016 | Sarkar |
| 2017/0084024 A1* | 3/2017 | Gurevich ............. A61B 5/7239 |
| 2017/0312023 A1* | 11/2017 | Harlev ................. A61M 25/007 |
| 2018/0028079 A1* | 2/2018 | Gurevich ............. A61B 5/7232 |
| 2018/0070875 A1* | 3/2018 | Kshetrapal ............. A61B 5/388 |
| 2018/0114591 A1 | 4/2018 | Pribanic et al. |
| 2018/0310828 A1 | 11/2018 | DiMaio et al. |
| 2018/0365833 A1* | 12/2018 | Dhaini ................. G06V 10/763 |
| 2019/0073772 A1* | 3/2019 | Ishihara ............... A61B 5/4842 |
| 2019/0122330 A1* | 4/2019 | Saget ...................... A61F 2/461 |
| 2020/0100881 A1* | 4/2020 | Emery, III ............. G06T 7/593 |
| 2020/0129136 A1 | 4/2020 | Harding et al. |
| 2020/0160510 A1 | 5/2020 | Lindemer et al. |
| 2020/0327670 A1 | 10/2020 | Connor |
| 2020/0357513 A1 | 11/2020 | Katra et al. |
| 2020/0364864 A1 | 11/2020 | Shanbhag et al. |
| 2021/0045640 A1* | 2/2021 | Poltorak ............. A61B 5/7264 |
| 2022/0047894 A1* | 2/2022 | Kenney ................. G16H 40/67 |

FOREIGN PATENT DOCUMENTS

| | | |
|---|---|---|
| WO | 2008/013722 A1 | 1/2008 |
| WO | 2013082289 A1 | 6/2013 |
| WO | 2013188470 A1 | 12/2013 |
| WO | 2014123978 A2 | 8/2014 |
| WO | 2015200704 A1 | 12/2015 |
| WO | 2017096224 A1 | 6/2017 |
| WO | 2017106858 A1 | 6/2017 |
| WO | 2018/144715 A1 | 8/2018 |
| WO | 2018/210692 A1 | 11/2018 |
| WO | 2019/030384 A1 | 2/2019 |
| WO | 2019/096828 A1 | 5/2019 |
| WO | 2019/136559 A1 | 7/2019 |

OTHER PUBLICATIONS

Hunter William L;Devices, Systems and Methods for Monitoring Knee Replacements; 2016 (Year: 2016).*
Brooks Amanda; Implantable Devices for Bone or Joint Defects; 2014 (Year: 2014).*
U.S. Appl. No. 16/863,590, filed Apr. 30, 2020, by Katra et al.
U.S. Appl. No. 17/215,419, filed Mar. 29, 2021, by Katra et al.
International Search Report and Written Opinion of International Application No. PCT/US2021/028092, mailed Aug. 31, 2021, 8 pp.
Response to Office Action mailed Aug. 3, 2021, from U.S. Appl. No. 16/863,590, filed Nov. 3, 2021, 17 pp.
Response to Office Action dated Feb. 15, 2023 from U.S. Appl. No. 17/215,419, filed May 12, 2023, 14 pp.
Response to Office Action dated Jul. 19, 2022 from U.S. Appl. No. 16/863,590, filed Nov. 2, 2022, 14 pp.
Advisory Action from U.S. Appl. No. 17/215,419 dated Sep. 25, 2023, 3 pp.
Final Office Action from U.S. Appl. No. 17/215,419 dated Jul. 17, 2023, 27 pp.
Response to Final Office Action dated Jul. 17, 2023 from U.S. Appl. No. 17/215,419, filed Sep. 14, 2023, 12 pp.
Office Action from U.S. Appl. No. 16/863,590, dated Aug. 3, 2021, 20 pp.
Advisory Action from U.S. Appl. No. 16/863,590, dated Apr. 18, 2022, 4 pp.
Response to Final Office Action dated Apr. 18, 2022, from U.S. Appl. No. 16/863,590, filed May 31, 2022, 19 pp.
Response to Final Office Action dated Jan. 28, 2022, from U.S. Appl. No. 16/863,590, filed Mar. 28, 2022, 22 pp.
Final Office Action from U.S. Appl. No. 16/863,590, dated Jan. 28, 2022, 23 pp.
Notice of Allowance from U.S. Appl. No. 16/863,590 dated Apr. 21, 2023, 10 pp.
Notice of Allowance from U.S. Appl. No. 16/863,590 dated Feb. 15, 2023, 10 pp.

(56) References Cited

OTHER PUBLICATIONS

Office Action from U.S. Appl. No. 17/215,419 dated Feb. 15, 2023, 29 pp.
Office Action from U.S. Appl. No. 16/863,590 dated Jul. 19, 2022, 30 pp.
"SBP scientist helps develop smartphone app for one-hour identification of bacteria," Sanford Burnham Prebys Medical Discovery Institute, Sep. 20, 2018, 3 pp.
"TYRX® Comments on Medicare Decision to Stop Paying for Infections Following Pacemaker or Defibtillator Implants," Pappas Capital, LLC, retrieved from http://www.pappas-capital.com/tyrx-comments-medicare-decision-stop-paying-infections-following-pacemaker-or-defibrillator-implants/, Aug. 2, 2012, 1 pp.
"Ugandan Student Create Vaginal infection Detection App," retrieved from https://herhealthuganda.com/ugandan-students-create-vaginal-infection-detection-app/, Oct. 17, 2017, 2 pp.
Baddour et al., "Update on Cardiovascular Implantable Electronic Device Infections and Their Management," American Heart Association, Inc., vol. 121, Issue 3, Jan. 26, 2010, 20 pp.
Daneman et al., "The predictors and economic burden of early-, mid-, and late-onset cardiac implantable electronic device infections: a retrospective cohort study in Ontario, Canada," Clin Microbiol Infect, Feb. 2019, 6 pp.
Dillon, "User Interface Design," MacMillian Encyclopedia of Cognitive Science, vol. 4, 2003, 16 pp. (Applicant points out, in accordance with MPEP 609.04(a), that the year of publication, 2003, is sufficiently earlier than the effective U.S. filing date, so that the particular month of publication is not in issue.).
Eby et al., "Analysis of Cardiac Implantable Electronic Device Infection Costs at One Year in a Large United States Health Care Organization," Poster presented at IDWeek, San Diego, CA, Oct. 4-8, 2017, 1 pp.
Greenspon et al., "16-Year Tends in the Infection Burden for Pacemakers and Implantable Cardioverter-Defibrillators In the United States," J Am Coll Cardiol, vol. 58., No. 10, 2011, 6 pp. (Applicant points out, in accordance with MPEP 609.04(a), that the year of publication, 2011, is sufficiently earlier than the effective U.S. filing date, so that the particular month of publication is not in issue.).
Gunter et al., "Evaluating Patient Usability of an Image-Based Mobile Health Platform for Postoperative Wound Monitoring," JMIR Mhealth Unhealth, vol. 4, Issue 3, Sep. 28, 2016, 15 pp.
Gutiérrez-Carretero et al., "Infections on Cardiovascular Implantable Electronic Devices: a Critical Review," Medical Research Archives, vol. 7, issue 3, Mar. 2019, 64 pp.
Harper et al., "Clinical presentation of CIED infection following initial implant versus reoperation for generator change or lead addition," Open Heart, British Cardiovascular Society, 2018, 7 pp. (Applicant points out, in accordance with MPEP 609.04(a), that the year of publication, 2011, is sufficiently earlier than the effective U.S. filing date, so that the particular month of publication is not in issue.).
Henrickson et al., "Antibacterial Envelope Is Associated With Low Infection Rates After Implantable Cardioverter-Defibrillator and Cardiac Resynchronization Therapy Device Replacement," JACC EP. May 2017, 10 pp.
Kirsh, "This smartphone app could detect infectious diseases," retrieved from https://www.medicaldesignandoutsourcing.com/this-smartphone-app-could-detect-infectious diseases/, Nov. 6, 2018, 15 pp.
Mittal et al., "Cardiac implantable electronic device infections: Incidence, risk factors, and the effect of the AigisRx antibacterial envelope," Heart Rhythm Society, Mar. 7, 2014, 7 pp.
Nielsen et al., "Infected cardiac-implantable electronic devices: prevention, diagnosis, and treatment," European Heart Journal, Mar. 6, 2015, 7 pp.
Shandrow, "This Smart Skin-Scanning App Could Save Your Life," retrieved from https://wwww.entrpreneur.com/article/237953, Oct. 2, 2014, 8 pp.
Sohail, "Cardiovascular Implantable Electronic Device (CIED) Infection," retrieved from https://www.infectiousdiseaseadvisor.com/home/decision-support-in-medicine/infectious-diseases/cardiovascular-implantable-electronic-device-cied-infection/, Jan. 20, 2019, 12 pp.
Strachan, "Value-Based Healthcare: What role does HTA play?," HTAi 2018 Annual Meeting Vancouver Canada, Jun. 1-5, 2018, 14 pp.
Strickland, "Diagnosing Ear Infections With Your Smartphone," retrieved from https://www.wbur.org/hereandnow/2014/12/17/ear-infections-app, Dec. 17, 2014, 4 pp.
Tarakji, "WRAP-IT Substudy Provides Strong Prospective Support for CIED Infection Prevention," Heart, Vascular, and Thoracic Research, retrieved from https://consultqd.clevelandclinic.org/wrap-it-substudy-provides-strong-prospective-support-for-cied-infection-prevention/, Nov. 18, 2019, 3 pp.
U.S. Appl. No. 17/021,521, filed Sep. 15, 2020, by Sarkar et al.
Li et al., "Imaging in Chronic Wound Diagnostics," Advances in Wound Care vol. 9, No. 5, Mar. 19, 2020, 19 pp.
Office Action from U.S. Appl. No. 17/215,419 dated Nov. 8, 2023, 29 pp.
Response to the Final Office Action dated Jul. 17, 2023 and the Advisory Action dated Sep. 25, 2023, from U.S. Appl. No. 17/215,419, filed Oct. 16, 2023, 13 pp.
Response to Office Action dated Nov. 8, 2023 from U.S. Appl. No. 17/215,419, filed Feb. 7, 2024, 15 pp.
Advisory Action from U.S. Appl. No. 17/215,419 dated Jun. 28, 2024, 8 pp.
Final Office Action from U.S. Appl. No. 17/215,419 dated Apr. 22, 2024, 39 pp.
Final Office Action from U.S. Appl. No. 18/355,260 dated Jun. 21, 2024, 28 pp.
Office Action from U.S. Appl. No. 18/355,260 dated Mar. 4, 2024, 23 pp.
Response to Final Office Action dated Apr. 22, 2024 from U.S. Appl. No. 17/215,419, filed Jun. 11, 2024, 19 pp.
Response to Office Action dated Mar. 4, 2024 from U.S. Appl. No. 18/355,260, filed Jun. 3, 2024, 18 pp.
Advisory Action from U.S. Appl. No. 18/355,260 dated Sep. 6, 2024, 3 pp.
Notice of Allowance from U.S. Appl. No. 17/215,419 dated Aug. 26, 2024, 9 pp.
Notice of Allowance from U.S. Appl. No. 17/215,419 dated Nov. 1, 2024, 9 pp.
Office Action from U.S. Appl. No. 18/355,260 dated Oct. 2, 2024, 37 pp.
Pre-Appeal Brief Request for Review from U.S. Appl. No. 17/215,419, filed Jul. 17, 2024, 6 pp.
Response to Final Office Action dated Jun. 21, 2024 from U.S. Appl. No. 18/355,260, filed Aug. 20, 2024, 16 pp.
Response to Final Office Action dated Jun. 21, 2024 from U.S. Appl. No. 18/355,260, filed Sep. 16, 2024, 22 pp.
Pre-Brief Appeal Conference decision from U.S. Appl. No. 17/215,419 dated Aug. 20, 2024 2 pp.
Response to Office Action dated Oct. 2, 2024 from U.S. Appl. No. 18/355,260, filed Dec. 23, 2024, 24 pp.
Final Office Action from U.S. Appl. No. 18/355,260 dated Jan. 17, 2025, 15 pp.

\* cited by examiner

POST OPERATIVE IMPLANTATION SITE MONITORING AND MEDICAL DEVICE PERFORMANCE

This application claims the benefit of U.S. Provisional Application Ser. No. 63/018,047, filed Apr. 30, 2020, the entire content of which is incorporated herein by reference.

FIELD

This disclosure relates to medical devices, and in some specific examples, relates to computing devices (e.g., mobile devices) configured to evaluate a patient's recovery from implantation of a medical device and/or to evaluate the performance of a medical device that is presently implanted in the patient.

BACKGROUND

Medical devices may be used to treat a variety of medical conditions. Example medical devices include implantable medical devices (IMDs), such as cardiac or cardiovascular implantable electronic devices (CIEDs). An IMD, also referred to at times as an "implanted medical device," may include a device implanted in a patient at a surgically or procedurally prepared implantation site. The IMD may include a diagnostic device configured to diagnose various ailments of a patient, monitor a health status of the patient, etc. In addition, or alternatively, an IMD may also be configured to deliver electrical stimulation therapy to a patient via electrodes, such as implanted electrodes, where the device may be configured to stimulate the heart, nerves, muscles, brain tissue, etc. In any case, the IMD may, in some instances, include a battery powered component, such as when referring to implantable cardiac pacemakers, implantable cardioverter-defibrillators (ICDs), other electrical stimulators including spinal cord, deep brain, nerve, and muscle stimulators, infusion devices, cardiac and other physiologic monitors, cochlear implants, etc. In such instances, the battery powered component of the IMD may be implanted, such as at a surgically or procedurally prepared implantation site. In addition, associated devices, such as elongated medical electrical leads or drug delivery catheters, can extend from the IMD to other subcutaneous implantation sites or in some instances, deeper into the body, such as to organs or various other implantation sites.

While preparation and implantation are conducted in a sterile field, and the IMD components are packaged in sterile containers or sterilized prior to introduction into the sterile field, there can still be a risk of introduction of microbes into the sites. Implanting clinicians therefore typically apply disinfectant or antiseptic agents to the skin at the surgical site prior to surgery, directly to the site before the incision is closed, and prescribe oral antibiotics for the patient to ingest during recovery. Despite these precautions, infections can occur.

Accordingly, infection associated with implantation of medical devices remains a health and economic concern. If an infection associated with an IMD occurs, explanting the device can often be the only appropriate course of action. In addition, once a site becomes infected, the infection can migrate, e.g., along the lead or catheter to locations in which the lead and/or catheter are implanted. Removal of a chronically implanted lead or catheter, e.g., in response to such an infection, can be difficult. Aggressive systemic drug treatment is prescribed to treat such infections. However, early detection of infections associated with IMDs may allow for earlier intervention, resulting in fewer device explants.

In some instances, patients who have had certain medical devices implanted, such as CIEDs, are required to have a post-implant follow-up consultation visit with a healthcare professional (HCP). The HCP visit typically occurs anywhere from a few days to a few weeks after the implantation. The HCP typically performs a wound check and possibly initiates a device interrogation session to determine performance metrics of the CIED. These visits are non-remarkable and brief in the majority of cases, at a level as high as over 90%. However, the post-implant follow-up visit may still constitute for the patient a required checkpoint with the HCP. In some cases, this follow-up visit uncovers a potential infection or device-related complications that potentially warrant clinical intervention.

SUMMARY

While the actual follow-up consultation visits with the healthcare professional (HCP) tend to be relatively short, the visits can still constitute a burden on the patient's life, the physician's clinic, and on the healthcare system overall. Aspects of this disclosure are directed to one or more computing devices having processing circuitry, where the processing circuitry is configured to facilitate or simulate a virtual check-in for a patient, such as a virtual follow-up or other wellness check, where a patient and/or physician may check on the status of medical devices, including implantable medical devices (IMDs), and/or on the patients themselves.

A system of processing circuitry of the one or more computing devices may implement various tools and techniques (hereinafter, "tools," a system of processors, or a processing circuitry system) in order to provide a virtual check-in for the patient. The processing circuitry system may be configured to provide an option for the patient to engage in an interactive session (e.g., virtual check-in process, interactive check-in session, interactive reporting process, etc.) as part of a post-implant evaluation, for which the patient can undergo an interactive reporting session remotely, as in remotely from a formal doctor's office setting or other HCP setting. In some examples, processing circuitry of a mobile or portable computing device may be configured to manage the interactive session, such that a user may be able to effectively navigate the interactive session from any remote location. In addition, the processing circuitry system may communicate patient and/or medical device data between various computing devices (e.g., end-user mobile devices, camera devices, wearable devices, edge devices, etc.). In some examples, the processing circuitry system may be configured to manage the interactive session to ensure proper interaction with the check-in tools, such that the system may accurately determine whether any complications have arisen with the patient and/or the IMD. The processing circuitry system may communicate such information over a network and/or through implementation of various communication protocols.

In some instances, the processing circuitry system may implement the interactive session in a secure setting, such as on an authenticated mobile computing device and/or over a secure data network. In some instances, the processing circuitry system may implement the interactive session on a mobile device configured to perform one or more of the various techniques of this disclosure, with or without the assistance of other devices (e.g., network devices). That is, the mobile device may operate various software tools configured to perform the virtual check-in process. A patient may then conduct an entire session of the virtual interactive check-in session (e.g., a plurality of subsessions of an interactive session) without network access or with limited network use as in the use of wireless communication with an edge device (e.g., an IoT device with additional processing resources to assist or perform the various check-in functions). The mobile device may, at a later point in time following the completion of a check-in session (e.g., a plurality of subsessions of an interactive session), synchronize the virtual check-in data with other network devices. In this way, a HCP may access the data at that time, where it might not be critical that the HCP access such data in real-time or near real-time as the patient conducts the particular check-in session (e.g., a plurality of subsessions of an interactive session).

In accordance with techniques of this disclosure, a processing circuitry system is configured to provide a comprehensive user interface (UI) to a user (e.g., the patient), where the UI is configured to guide the user through the interactive session and/or an evaluation process. The processing circuitry of a computing device may provide the UI to the user by generating UI program data and/or accessing UI program data from memory. In some instances, the processing circuitry may access UI program data from a separate computing device of a virtual check-in computing system. In some instances, the processing circuitry of the computing device may tailor the UI program data to each particular user or class of users. In some instances, the processing circuitry system may tailor UI program data by deploying various artificial intelligence (AI) algorithms and/or machine learning (ML) models that are configured to determine a UI that reflects the particular user or class of users and the one or more medical devices corresponding to the particular user or class of users. In any case, the processing circuitry system may be configured to provide, via a display device, the UI to the user of a user-operated computing device.

In some examples, the UI may include interactive UI check-in elements (e.g., UI tiles) configured to guide a patient systematically through the virtual check-in process. The UI check-in elements may be configured to actively assist a particular patient with providing specific patient input to the system. The patient input may include specific types of information and particular amounts of information. In some examples, the processing circuitry system may use the information to, for example, identify various maladies of the patient, such as device pocket infections, or otherwise, identify abnormalities with the medical device and/or the patient. In some examples, the processing circuitry system may deploy AI and/or ML models in order to evaluate input received via the UI in order to determine a health status of the patient and/or a status of the one or more medical devices, including of an IMD. In another example, the processing circuitry system may communicate input from the patient to a HCP. The processing circuitry system may, in turn, receive input from the HCP. In such instances, the processing circuitry system may determine, based on the HCP input, the health status of the patient and/or the status of the one or more medical devices. In any case, the processing circuitry system may train the AI and/or ML models on patient input and/or on HCP input, where the processing circuitry system may obtain HCP input that, in some instances is based on the patient input (e.g., uploaded images of implantation site, ECG waveforms, etc.). Accordingly, the processing circuitry system may utilize information from multiple sources to determine various maladies of the patient. While described with reference to a comprehensive UI, the techniques of this disclosure are not so limited, and it will be understood that the UI elements may be implemented as stand-alone UIs that involve a subset of the UI elements of this disclosure. That is, processing circuitry of the computing device may not include all UI elements in a single UI program, and may in some instances, include additional UI elements configured to provide various other check-in functionalities.

In some examples, the UI check-in elements may include general patient-status check-in elements, physiological parameter check-in elements, medical device check-in elements, site check elements, such as wound check elements, etc. The processing circuitry system may obtain information relating to the various discrete check-in elements and determine a health status of the patient, such as a status of an IMD of the patient. In some instances, a patient may perform such virtual checks periodically to check on a status of the medical device or implantation site. That is, the patient may perform wellness checks even after performing a number of virtual check-in sessions (e.g., a plurality of subsessions of an interactive check-in session) that were either mandated or recommended by a HCP following a surgical event of the patient.

The interactive reporting session can replace, and/or in some instances supplement, in-person HCP visits. In some examples, the processing circuitry system of this disclosure may use the results of the computing device-implemented check to determine whether or not to provide an indication to the patient, and in certain cases, a physician or other HCP, as to whether an in-person visit is warranted, or alternatively, if the IMD wound recovery is progressing with the patient as expected. In addition, a processing circuitry system may implement one or more subsessions of the interactive session to determine if the one or more medical devices are functioning within acceptable bounds, etc. In some instances, the processing circuitry system may obtain information from a user, via one computing device, such as a mobile telephone device, and evaluate the information, via another computing device, such as an edge device or a network server. In such instances, an edge device may deploy AI and/or ML models trained on medical device data, patient data, and/or heuristic data obtained from a network. The processing circuitry system may, in some instances, train the AI or ML models on data obtained from the computing device of the user and/or from data obtained directly from the medical devices of the patient. In such instances, those medical devices may be configured to communicate with an edge device, as well as a user computing device.

In one example, the disclosure provides a method of imaging a body of a patient of an IMD, the method comprising: identifying, via processing circuitry of a computing device, a first set of images that represent a particular location of the body in which at least one component of the IMD coincides; determining, from the first set of images, a projection of alteration characteristics of the particular location of the body projected over time; identifying, via the processing circuitry, a second set of images that represent the particular location of the body at a progression interval that follows in time the first set of images; determining, from the second set of images, a second set of alteration characteristics; comparing, via the processing circuitry, the second set of alteration characteristics to the projection; and identifying, based at least in part on the comparison, a potential abnormality at the particular location of the body.

In another example, the disclosure provides a system for imaging a body of patient of an IMD, the system comprising: a memory configured to store one or more frames of image data, the one or more frames representing at least a first set of images; and one or more processors in communication with the memory, the one or more processors configured to: identify the first set of images that represent a particular location of the body in which at least one component of the IMD coincides; determine, from the first set of images, a projection of alteration characteristics of the particular location of the body projected over time; identify a second set of images that represent the particular location of the body at a progression interval relative to the first set of images; determine, from the second set of images, a second set of alteration characteristics; compare the second set of alteration characteristics to the projection; and identify, based at least in part on the comparison, a potential abnormality at the particular location of the body.

The disclosure also provides non-transitory computer-readable media comprising instructions that cause a programmable processor to perform any of the techniques described herein. In an example, this disclosure provides a non-transitory computer-readable storage medium having stored thereon instructions that, when executed, cause one or more processors to: identify a first set of images that represent a particular location of a body of a patient in which at least one component of an implantable medical device (IMD) coincides; determine, from the first set of images, a projection of alteration characteristics of the particular location of the body projected over time; identify a second set of images that represent the particular location of the body; determine, from the second set of images, a second set of alteration characteristics; compare the second set of alteration characteristics to the projection; and identify, based at least in part on the comparison, a potential abnormality at the particular location of the body.

The disclosure also provides means for performing any of the techniques described herein.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
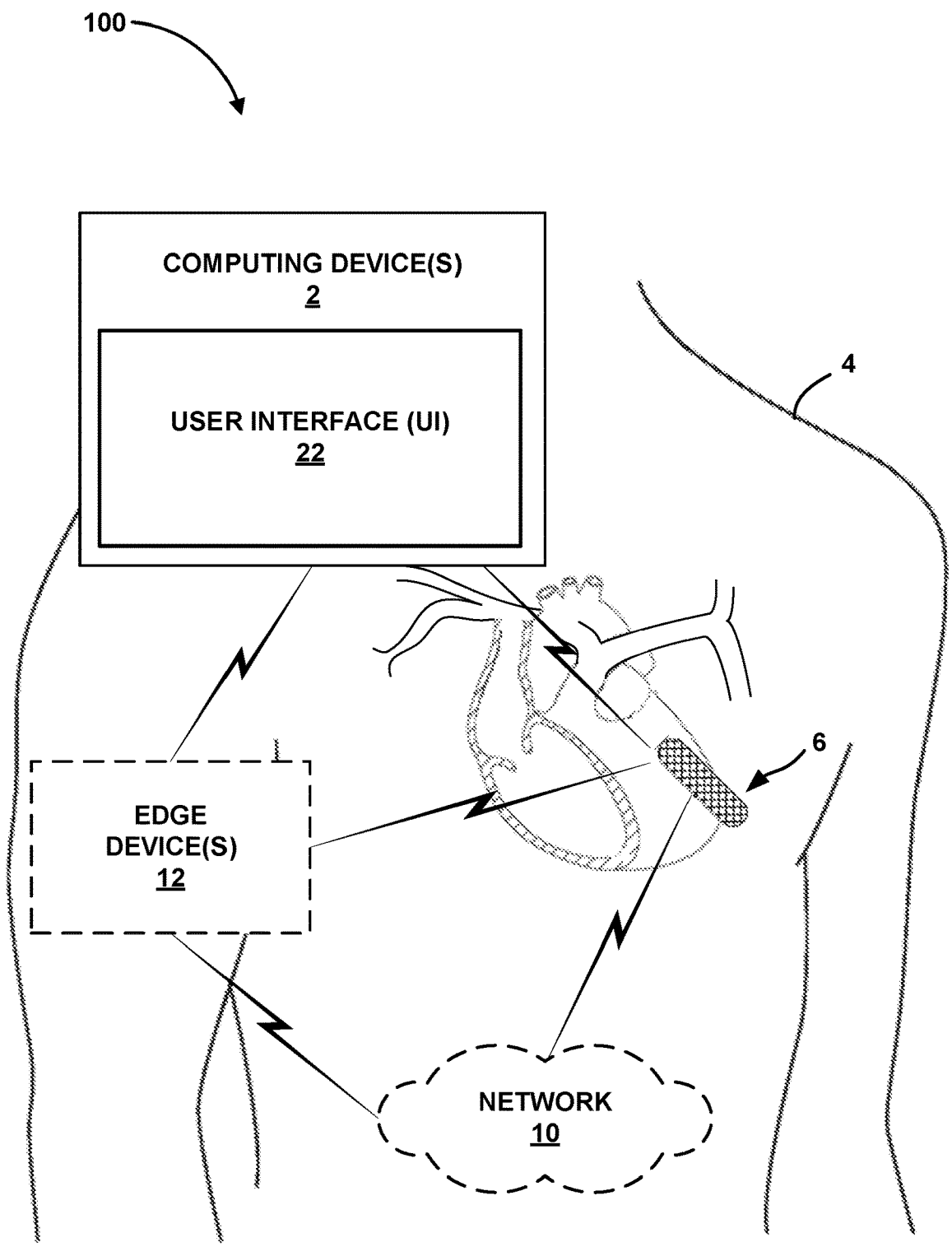
FIG. 1 illustrates the environment of an example monitoring system in conjunction with a patient, in accordance with one or more techniques disclosed herein.

In 2019, over 1.5 million implantable medical device (IMD) implants were expected to be implanted in patients worldwide. Per Heart Rhythm Society (HRS) and European Heart Rhythm Association (EHRA) guidelines, each of those implants should have had an in-person follow-up within two to twelve weeks. Patient adherence with the post-implant visit improves mortality and patient outcome. Patient compliance with this visit, however, ranges from 55-80%. For 93-99% of these visits, patients present without abnormalities (e.g., infections). That is, many of these visits could be performed virtually.

This disclosure presents systems and methods for remote post-IMD monitoring for implantation site infections. Implantation infections are estimated to occur in about 0.5% of IMD implants and about 2% of IMD replacements. Early diagnosis of IMD infections can help drive effective antibiotic therapy or device removals to treat the infection. This is done in an in-hospital, post-op setting where the patients can be continuously monitored.

A post-discharge infection diagnosis typically follows when patients feel any infection-related symptoms, such as pain or fever. However, for the subset of asymptomatic patients with infection that are unable to self-report any implantation site abnormalities, there is a need for expert review. Since having all patients come-in for a physical infection review can be cumbersome for both patients and caregivers, there is a need for remote monitoring of implantation sites.

In general, this disclosure is directed to a browser interface or a mobile device app that can be operated via a variety of user-facing computing devices, including, but not limited to, a smartphone, tablet computer, mobile device, virtual reality (VR), augmented reality (AR), or mixed reality (MR) headset, etc. The computing device may execute a software app that causes the computing device to perform various functionalities described herein either locally, using the computing resources of the computing device, or via cloud computing, such as by transmitting captured data via a network interface to a backend system (e.g., a server system) that performs some or all of the analysis described herein. In addition, as described herein, some or all of the analysis may be performed, via edge computing, such as by transmitting captured data to an edge device (e.g., an IoT device or another computing device). In some examples, edge devices may include user-facing or client devices, such as smartphones, tablet computers, PDAs, and other mobile computing devices. In any case, a backend system may or may not include certain edge devices as part of the backend system. In one examples, a network may interface with one or more edge devices operating at the edge of the backend system, so as to form an intermediary between a computing device of a user and the various servers of a network. In such examples, a computing device may perform the various techniques of this disclosure by leveraging edge computing, cloud computing, or a combination thereof. An example combination of edge and cloud computing may include distributive computing or distributed computing systems. In any case, the computing device may perform the techniques of this disclosure in-app, in-tablet and/or in cloud environments.

In the cloud-based implementations of this disclosure, the mobile device app may receive various types of post-analysis data from the backend system, and present the data to the user, either in as-received form, or after performing some additional processing or formatting of the data locally.

The computing device executing the app (e.g., a virtual check-in process) may perform various functionalities described below, whether via local computing resources provided by the computing device, via cloud-based backend systems, or both. In some examples, the computing device may implement the app via a web browser. In some examples, the computing device may perform a device check. In such examples, the computing device may implement one or more interrogations of one or more medical devices (e.g., IMDs, CIEDs, etc.). In addition, the computing device may analyze medical device settings, parameters, and performance metrics.

In some examples, the computing device may perform a physiologic check. In such examples, the computing device may enable monitoring and/or analysis of physiologic signals detected from the patient including electrocardiogram (ECG) signals, and other health signals that can be recorded (e.g. respiration, impedance, activity, pressure, etc.).

In addition, the computing device may perform a check of one or more surgical sites (e.g., an implant wound, an implant-removal implantation site, etc.). In some examples, the computing device may implement image processing with respect to an area indicative of an implantation site (e.g., a wound site). In some examples, the computing device may perform image processing using camera(s) of, or otherwise communicatively coupled to, the computing device to detect abnormalities, such as in wound healing and/or by determining potential infections at an implantation site.

In some examples, the computing device may perform a patient status check. The app may implement an interactive logging, journaling, or diary function for the patient to respond to a few key questions regarding patient health information, medications, symptoms, physiological or anatomical metrics, or any relevant patient-reported information.

The tools of this disclosure may, in some examples, use artificial intelligence (AI) engines and/or machine learning (ML) models. In some examples, the AI engines may use cohort data to conduct individual checks. A cohort may include any number of cohorts, including a CIED cohort that includes CIED patients, an age cohort, a skin pigmentation cohort, an IMD type cohort, etc. or combinations thereof. In addition, the ML models may be trained using cohort data to conduct individual checks. In the wound check example, the tools of this disclosure may invoke image recognition or image processing AI that leverages (e.g., is trained using) wound and infection libraries available from various sources.

To perform ECG checks, the tools of this disclosure may use arrhythmia classification AI with a QRS model to classify normal rhythm and any underlying arrhythmias relative to the patient demographics and characteristics. It will be understood that a QRS model generally refers to a QRS complex that contains a combination of various graphical deflections included with a typical electrocardiogram (e.g., a Q wave, an R wave, an S wave, etc.).

To perform device check functionalities of this disclosure, the app may leverage various communication hardware components of the computing device to interrogate the one or more medical devices (e.g., an IMD) to retrieve medical device parameters specific to the medical device family. The processing circuitry system may be configured to compare the retrieved parameters to the physician's earlier-provided settings as well as to comparable medical device families for deviation of normality/normalcy analysis.

The tools of this disclosure may also provide patient status check functionalities using an interactive session with the patient in which the patient provides elicited input to answer questions related to the patient's health and present condition. In various examples, the tools of this disclosure may enable the patient to enter information (e.g., condition information or results) via text entry, dropdown menu selection from prepopulated responses, and/or radio buttons as shown in one or more of the accompanying drawings. In some non-limiting examples, the tools of this disclosure may output questions, to elicit patient responses by which the patient could enter information such as medications, doses thereof, as well as other prompted information.

At the completion of the session (e.g., an interactive reporting session), the tools of this disclosure may mark the results on the UI provided via the mobile device app, with date and time stamping. The tools of this disclosure may provide the patient with the capability to generate a report (e.g., as a portable document format (PDF) or in various other formats) for the records of the patient, to email or otherwise transfer the report or select contents of the report to family members or to a doctor (e.g., via a File Transfer Protocol (FTP)), etc.

The app of this disclosure may, in some non-limiting examples, provide the patient the capability to save the results locally to the computing device (e.g., a smartphone or tablet computer) for future comparison, reference, or use as a standalone file. In some instances, the computing device may store the results locally to the computing device for use as a retrievable session within the app or other app, or as part of a health kit implemented on the computing device. The app of this disclosure may, in some non-limiting examples, push the report to a proprietary network (e.g., via an online portal). By pushing the report or other data in this way, the tools of this disclosure enable the HCP to review the patient's health information and enter data into an electronic medical records (EMR) database or repository. The tools of this disclosure may generate a confirmation of receipt by the HCP based on various criteria (and in some examples, an indication of whether the report was reviewed by the HCP), and provide this communication to the patient via communication to the mobile device or other patient-accessible computing modality. In some examples, the computing device may be configured to receive an indication as to whether the report was reviewed by the HCP. In such examples, the computing device may be configured to provide, based at least in part on the indication, a user with a status of the report (e.g., HCP reviewed, review in-progress, etc.).

If the tools of this disclosure determine that any one check or any combination of checks described above yielded an abnormal result (or abnormal outside an acceptable margin of normal), the tools of this disclosure may use the mobile device app to output a prompt to the patient. In some examples, the prompt may indicate an abnormality. In some examples, the prompt may include a recommendation or instruction to schedule a follow-up visit with the HCP.

In some examples, the tools of this disclosure may store session information (e.g., subsession information, combined session information, etc.) and results of previous checks (e.g., locally at the computing device, to a cloud storage resource, or to both). The computing device may do this in order to assist the patient and/or the HCP in tracking a progress or changes with respect to the patient's wound recovery, the functioning of the medical device, etc. In some examples, the tools of this disclosure may implement a limited date counter with respect to the app in order to deter or prevent the patient from continually using the app after the follow-up time window has expired. Aspects of this disclosure enable bidirectional communication, e.g. to loop in the physician, who may communicate with various messages, such as "call my office," etc.

As would be appreciated by one of skill in the art, the remote medical device monitoring, as disclosed herein, represents a significant technological advance over prior implementations. Specifically, the disclosed techniques can identify and display a tailored set of patient-related content elements and additionally augmented content, resulting in an increased efficiency in accessing the relevant content quickly and allowing user interactions with multiple patient-related content elements (e.g., content tiles, subsession interfaces, time lapse representations, etc.). Further, the disclosed techniques can yield health benefits by dynamically determining the presence of abnormalities by using specific tools that are deployed and implemented at particular moments in order to achieve the highest accuracy of an abnormality detection. A user may also be presented with the relevant control mechanisms that allow the user to intuitively operate the UI in order to capture the correct images (e.g., frequent images over a first time frame and less frequent images over a second time frame in order to determine a projection of healing or other alterations at a particular bodily site of patient 4), the correct physiological parameters, the correct device interrogation data, and the correct patient-status updates, that will be used to achieve the highest accuracy of an abnormality detection. As such, the examples described herein represent significant improvements in this computer-related technology.

Additional examples disclosed herein also represent improvements in computer-related technology. For example, the camera system may use augmented overlays (e.g., wireframes) in order to allow a user to accurately align an implantation site or other part of the body of the patient, such that images may be obtained in a consistent and reliable manner. In addition, the use of such augmented overlays allows a computing device to receive consistent images at particular angles and/or with particular implantation-site sizes in order to determine a progression of a healing of the patient over time based on a particular analysis of the images over time. Another technical improvement includes the use of stored images of a body of the patient (e.g., images taken shortly after surgery) in order to develop a wireframe (e.g., a transparent augmented reality overlay) that emulates the implantation site, such that a patient may be able to accurately align the implantation site with the wireframe as a guide to capturing the image at a particular angle and/or size or with particular contrast, lighting, zoom, etc. Advantageously, the computing device may initiate an automatic still-image capture of the image of the implantation site when, for example, a healing scar at the implantation site fits within a particular area of the wireframe. The computing device may utilize the still-image capture in order to determine a projection over time from a plurality of advantageously aligned images, rather than determining a projection of healing over time from images that the capture or alignment thereof has not been controlled in any meaningful way. Additionally, the monitoring system disclosed herein may, in some examples, be native to other software applications, and thus, the tiles may be displayed using similar UI/UX elements. Other example improvements include the ability to call external sources of information to provide a greater relevance and complexity to a post-implant report and in some examples, the ability to call APIs (e.g., language translation APIs, machine learning APIs, ECG waveform analysis APIs) to perform additional work within the monitoring system. In one example, a cloud-deployed API may serve as the accessible endpoint for an ML model. In addition, various ML models or AI engines may be deployed as so-called light versions that are configured to operate efficiently on devices with significantly limited resources (e.g., mobile devices, tablets, etc.).

The ideas disclosed herein exist within the realm of computer-related technology. For example, the display of information in a UI where the relevant data does not necessarily reside in a storage device locally coupled to the relevant display device would be virtually impossible to replicate outside the realm of computer-related technology. That is, in some instances, relevant data (e.g., training sets, physiological parameter data, images, time lapse sets, image overlays, etc.) may be stored on a cloud storage device, whereas in some examples, the relevant data may be stored locally (e.g., on a mobile device of a patient) and/or synchronized with a cloud storage device or another device, such as a mobile device of a HCP, at a time advantageous to the system so as to converse computing resources (e.g., processing, memory, power resources, etc.). In a non-limiting example, the multi-faceted information representing, e.g., the static content tiles, dynamically augmented content tiles, etc., may be simultaneously or dynamically obtained from disparate systems, identified by metadata in some instances, and simultaneously or dynamically presented in an interactive session UI and subsession UIs. Additionally, the monitoring system may intuitively present the data on the proper display, through the proper medium, and/or at the proper moment (e.g., on a static schedule or dynamically-updating schedule). In addition, the techniques of this disclosure provide abnormality determination techniques that may utilize, in some examples, non-visual sensors, such as thermal imaging with cameras in order to detect temperature changes at an implantation site. In addition, various data analysis techniques are described that utilize a particular examples of synthesizing various data items (e.g., images of an implantation site, device status information, etc.), where the information sources may be optimized to provide specific data relative to the specific technical problem of patient monitoring post-implant. That is, the synthesis of data, in some examples, provides a robust algorithm for identifying abnormalities, notwithstanding the algorithms described for obtaining and analyzing specific sections of data, such as image data, for potential abnormalities.

Additionally, it has been noted that design of computer UIs "that are useable and easily learned by humans is a non-trivial problem for software developers." (Dillon, A. (2003) User Interface Design. MacMillan Encyclopedia of Cognitive Science, Vol. 4, London: MacMillan, 453-458.). The various examples of interactive and dynamic UIs of the present disclosure are the result of significant research, development, improvement, iteration, and testing and in some examples, provide a particular manner of obtaining information, summarizing, and presenting information in electronic devices. This non-trivial development has resulted in the UIs described herein, which are likely to provide significant cognitive and ergonomic efficiencies and advantages over previous systems going forward. The interactive and dynamic UIs include improved human-computer interactions that may provide, for a user, reduced mental workloads/burdens, improved decision-making, reduced work stress, etc. For example, a UI with the interactive UIs described herein may provide an optimized presentation of patient-specific information from various sources and may enable a user to more quickly access, navigate, assess, and utilize such information than with previous systems which can be slow, complex and/or difficult to learn, particularly to novice users. Thus, the presentation of concise and compact information on a particular UI that corresponds to a particular patient makes for efficient use of the information available and optimal use of the medical devices and virtual check-up functionalities of this disclosure.

FIG. 1 illustrates the environment of an example monitoring and/or check-in system 100 in conjunction with a patient 4. In some examples, system 100 may implement the various patient and medical device monitoring and abnormality detection techniques disclosed herein. System 100 includes one or more medical device(s) 6 and one or more computing device(s) 2. While medical device(s) 6, in some instances, include an IMD, as shown in FIG. 1, the techniques of this disclosure are not so limited. For illustrative purposes, however, medical device(s) 6 may in some instances be referred to herein simply as IMD 6 or IMD(s) 6.

Computing device(s) 2 may be a computing device with a display viewable by a user. The user, may be a physician technician, surgeon, electrophysiologist, clinician (e.g., implanting clinician), or patient 4. Patient 4 ordinarily, but not necessarily, will be a human. For example, patient 4 may be an animal needing ongoing monitoring for various health conditions (e.g., cardiac conditions, spinal cord conditions, etc.). In such instances, a human caregiver may operate aspects of the disclosed technology that utilize user input that may not be feasibly available from an animal patient 4.

Computing device(s) 2 may be referred to in some instances herein as a plurality of "computing device(s) 2," while in other instances may be referred to simply as "computing device 2," where appropriate. System 100 may be implemented in any setting where at least one of computing device(s) 2 may interface with and/or monitor at least one of medical device(s) 6 and/or an implantation site of medical device(s) 6, in accordance with one or more techniques of this disclosure. Computing device(s) 2 may interface with and/or monitor medical device(s) 6, for example, by imaging the implantation site of the medical device(s) 6, in accordance with one or more techniques of this disclosure. In addition, computing device(s) 2 may interrogate medical device(s) 6 to obtain data from medical device(s) 6, such as performance data, historical data stored to memory, battery strength of the medical device(s) 6, impedance, pulse width, pacing percentage, pulse amplitude, pacing mode, internal device temperature, etc. In some examples, computing device(s) 2 may perform an interrogation subsession with medical device(s) 6 by establishing a wireless communication with one or more of the medical device(s) 6. In some instances, medical device(s) 6 may or may not include an IMD. In an example, computing device(s) 2 interrogate the memory of a wearable medical device 6 in order to determine device operating parameters as the interrogation data. In another example, computing device(s) 2 may receive (e.g., obtain) physiological parameters from medical device(s) 6, such as waveforms of a physiological parameter, parameter labels (e.g., "abnormal ECG detected"), etc. In another example, computing device(s) 2 may obtain a patient-status entered into computing device(s) 2 by a user (e.g., patient 4, a caretaker of patient 4, etc.). In one example, the user may enter the patient-status updates via a user interface of computing device(s) 2. In another example, the user may enter the patient-status updates via another computing device 2 that may then transfer patient-status data to one of computing device(s) 2 that is/are configured to operate an interactive check-in session. In such examples, network 10 or edge device(s) 12 may facilitate the exchange of data between various computing device(s) 2, medical device(s) 6, etc., as described in further detail with reference to FIG. 3.

In some examples, computing device(s) 2 may include one or more of a cellular phone, a "smartphone," a satellite phone, a notebook computer, a tablet computer, a wearable device, a computer workstation, one or more servers, a personal digital assistant, a handheld computing device, virtual reality headsets, wireless access points, motion or presence sensor devices, or any other computing device that may run an application that enables the computing device to interact with medical device(s) 6 or interact with another computing device that is, in turn, configured to interact with medical device(s) 6.

At least one of computing device(s) 2 may be configured to communicate with medical device(s) 6 and, optionally, other ones of computing device(s) 2, via wired or wireless communication. Computing device(s) 2, for example, may communicate via near-field communication (NFC) technologies (e.g., inductive coupling, NFC or other communication technologies operable at ranges less than 10-20 cm) and/or far-field communication technologies (e.g., Radio Frequency (RF) telemetry according to the 802.11, Bluetooth® specification sets, or other communication technologies operable at ranges greater than NFC technologies). In some examples, computing device(s) 2 may include an interface for providing input to edge device(s) 12, network 10, and/or medical device(s) 6. For example, computing device(s) 2 may include a user input mechanism, such as a touchscreen, that allows a user to store image(s) to a database. In such examples, one of edge device(s) 12 may manage the database, which in some instances, computing device(s) 2 may access via network 10 in order to perform one or more of the various techniques of this disclosure.

Computing device(s) 2 may include a user interface (UI) 22. In some examples, UI 22 may be a graphical UI (GUI), an interactive UI, etc. In some examples, UI 22 may further include a command line interface. In some examples, computing device(s) 2 and/or edge device(s) 12 may include a display system (not shown). In such examples, the display system may comprise system software for generating UI data to be presented for display and/or interaction. In some examples, processing circuitry, such as that of computing device(s) 2, may receive UI data from another device, such as from one of edge device(s) 12 or server(s) 94 (FIG. 3), that computing device(s) 2 may use to generate UI data to be presented for display and/or interaction.

Computing device(s) 2 may be configured to receive, via UI 22, input from the user. UI 22 may include, for example, a keypad and a display, which may for example, be a liquid crystal display (LCD) or light emitting diode (LED) display. In some examples, a display of computing device(s) 2 may include a touch screen display, and a user may interact with computing device(s) 2 via the display. It should be noted that the user may also interact with computing device(s) 2 remotely via a network computing device.

UI 22 may further include, in some examples, a keypad. In some examples, UI 22 may include together the keypad with the display. The keypad may take the form of an alphanumeric keypad or a reduced set of keys associated with particular functions. Computing device(s) 2 may additionally or alternatively include a peripheral pointing device, such as a mouse, via which the user may interact with UI 22. In some instances, UI 22 may include a UI that utilizes virtual reality (VR), augmented reality (AR), or mixed reality (MR) UIs, such as those that may be implemented via a VR, AR, or MR headset.

In some examples, processing circuitry, e.g., processing circuitry 20 (FIG. 2) of computing device(s) 2, processing circuitry 64 of edge device(s) 12 (FIG. 3), processing circuitry 98 of server(s) 94 (FIG. 3), or processing circuitry 40 of medical device(s) 17, may determine identification data for patient 4, such as authentication data. In an example, processing circuitry 20 may identify, based at least in part on the identification data, IMD information that corresponds to IMD 6. As such, processing circuitry 20 may determine, based at least in part on the IMD information, an interactive session program that defines one or more parameters for imaging an implantation site, such as the implantation site of patient 4. In one example, the interactive session program may define one or more parameters for imaging one or more implantation sites of patient 4. The interactive session program may include the site-check subsession application, a patient-status subsession application, etc. (e.g., mobile app (s) installed from an app store). In some examples, the interactive session program may further include subsession process(es) (e.g., a site-check subsession imaging program, patient-status subsession program, physiological parameter subsession program, etc.) that are tailored to the user (e.g., patient 4, HCP, etc.) of computing device(s) 2.

In an illustrative example, system 100 includes a system for monitoring patient 4. The system includes a system of processors and storage devices, as those elements are described further with reference to FIGS. 2-4. In some examples, the storage devices may include a memory, such as a memory device of computing device(s) 2, where the memory may be configured to store image data (e.g., frames of image data, images of an implantation site, etc.). In addition, the storage devices may be configured to store additional data items, such as physiological parameter values, patient-status updates, device interrogation data, etc. The system of processors, which may include one or more processors, may be in communication with at least one of the storage devices configured to store image data.

In some examples, one of computing device(s) 2, may include one or more of the system of processors implemented in circuitry, where the one or more processors may be configured to provide an interactive session, such as an virtual check-in interactive session, via computing device 2. In such examples, the virtual check-in interactive session may be configured to allow a user to navigate a plurality of subsessions (e.g., via computing device 2). The plurality of subsessions may include at least two subsessions as part of the interactive session. In one example, the plurality of subsessions may include at least a first subsession and a second subsession. In such examples, the second subsession is distinct from the first subsession. In addition, the first subsession may include a subsession that involves capturing the image data via one or more cameras. That is, the first subsession may include a site-check subsession. The second subsession may include a device-check subsession, physiological parameter check subsession, a patient-status subsession, or other subsession configured to elicit information of patient 4 that would be useful in monitoring patient 4 (e.g., an IMD patient). In some instances, the interactive session may include a third and/or a fourth subsession, including one or more of a device-check subsession, physiological parameter check subsession, a patient-status subsession, or other subsessions, as particular example subsessions are described herein.

In the illustrative example, computing device 2 may determine a first set of data items in accordance with the first subsession of the interactive session. In such examples, the first set of data items includes the image data, such as frames of the image data. That is, computing device 2 may capture frames of image data via a camera (e.g., camera 32 of FIG. 2) and may store the frames to memory. In one example, the image data may include a frame of a still-image of an implantation site of medical device 6. In another example, the image data may include a frame of a still-image of areas of the body of patient 4 adjacent the implantation site, such as where leads may be routed beneath the skin of patient 4.

In some instances, computing device 2 may process the image data prior to storing the image data as the first set of data items. In an example, computing device 2 may deploy an AI engine and/or ML model trained to identify abnormalities in images of implantation sites or other body parts of patient 4. AI engine and/or ML model may determine abnormality metrics, such as a likelihood (e.g., a confidence value) of an abnormality at the implantation site, a type of abnormality, etc. In any case, computing device 2 may determine the first set of data items to include the image data (e.g., abnormality determination, etc.).

In addition, computing device 2 may determine a second set of data items in accordance with the second subsession of the interactive session. In such instances, the second set of data items may be distinct from the first set of data items. This is because the second subsession includes a subsession configured to obtain complementary or supplemental data relative to the first subsession, rather than to serve as a duplicate of the first subsession. To illustrate, the second set of data items may include one or more of: interrogation data obtained from medical device(s) 17 (e.g., IMD 6), one or more physiological parameters of patient 4, and/or user-input data. In such examples, computing device 2 may determine, based at least in part on the first set of data items and the second set of data items, an abnormality corresponding to at least one of the patient or the IMD. In one example, the first set of data items and the second set of data items may indicate various abnormality states. The abnormality states may include device migration, a potential infection, abnormal healing, abnormal physiological parameters, abnormal device parameters, patient-input indicating a perceived abnormality, etc. In addition, the abnormality states may include healing granulation around edges of an implantation site, discharge from an implantation site, inflammation at the implantation site, tissue erosion at or around the implantation site, etc. Thus, the abnormality corresponding to patient 4 or IMD 6 may include an abnormality determination based on the various abnormality states observed from the various data items.

In one example, computing device 2 may determine, from physiological parameters obtained via a second subsession, an ECG change that indicates device migration and as such, increases the likelihood that a potential abnormality is being detected from the image data. In such instances, computing device 2 may analyze the image data using a bias toward detecting an abnormality or may include, in a post-implant report, a heightened likelihood (e.g., probability, confidence interval) that is based on the likelihood of a potential abnormality determined from the first and second set data items. Computing device(s) 2 may output the post-implant report of the interactive session. In an illustrative example, the post-implant report may include an indication of the abnormality and/or indication of an amount of time that has transpired since the date of implantation of the IMD.

In some examples, computing device(s) 2 may include a programming head or paddle (not shown). In such examples, computing device(s) 2 may interface with medical device(s) 6 via the programming head. The programming head may be placed proximate to the body of patient 4 near medical device(s) 6 (e.g., near an implantation site of IMD 6). Computing device(s) 2 may include a programming head in order to improve the quality or security of communication between computing device(s) 2 and medical device(s) 6. In addition, computing device(s) 2 may include a programming head in order to improve the quality or security of communication between computing device(s) 2, medical device(s) 6, and/or edge device(s) 12.

In the illustrative and non-limiting example of FIG. 1, medical device(s) 6 include at least one IMD. In such examples, the at least one IMD may be implanted outside of a thoracic cavity of patient 4 (e.g., subcutaneously in the pectoral location illustrated in FIG. 1). In some examples, medical device(s) 6 may be positioned near the sternum near or just below the level of the heart of patient 4, e.g., at least partially within the cardiac silhouette. As used herein, an IMD may include, be, or be part of a variety of devices or integrated systems, such as, but not limited to, implantable cardiac monitors (ICMs), implantable pacemakers, including those that deliver cardiac resynchronization therapy (CRT), implantable cardioverter-defibrillators (ICDs), diagnostic devices, cardiac devices, etc. In some examples, the tools of this disclosure may be configured to monitor functioning of or user adaptation to implants other than CIEDs, such as spinal cord stimulators, deep brain stimulators, gastrological stimulators, urological stimulators, other neurostimulators, orthopedic implants, respiratory monitoring implants, etc.

In some examples, medical device(s) 6 may include one or more CIEDs. In some examples, patient 4 may interface with multiple medical device(s) 6, concurrently. In an illustrative example, patient 4 may have multiple IMDs implanted within the body of patient 4. In another example, medical device(s) 6 may include a combination of one or more implanted and/or non-implanted medical devices. An example of a non-implanted medical device includes a wearable device (e.g., monitoring watch, wearable defibrillator, etc.) or any other external medical devices configured to obtain physiological data of patient 4.

In some examples, medical device(s) 6 may include diagnostic medical devices. In an example, medical device(s) 6 may include a device that predicts heart failure events or that detects worsening heart failure of patient 4. In a non-limiting and illustrative example, system 100 may be configured to measure impedance fluctuations of patient 4 and process impedance data to accumulate evidence of worsening heart failure. In any case, medical device(s) 6 may be configured to determine a health status relating to patient 4. Medical device(s) 6 may transmit the diagnostic data or health status to computing device(s) 2 as interrogation data, such that computing device(s) 2 may correlate the interrogation data with image data to determine whether an abnormality present with a particular one of medical device(s) 6 (e.g., an IMD) or patient 4 (e.g., infection at an implantation site).

In some examples, medical device(s) 6 may operate as a therapy delivery device. For example, medical device(s) may deliver electrical signals to the heart of patient 4, such as an implantable pacemaker, a cardioverter, and/or defibrillator, a drug delivery device that delivers therapeutic substances to patient 4 via one or more catheters, or as a combination therapy device that delivers both electrical signals and therapeutic substances. As described herein, computing device(s) 2 may determine various interactive session programs or at least aspects of an interactive session program (e.g., imaging programs, UI programs, etc.), based the type of medical device implanted in patient 4 or based on identifying information of patient 4.

It should be noted that, while certain example medical device(s) 6 are described as being configured to monitor cardiovascular health, the techniques of this disclosure are not so limited, and persons skilled in the art will understand that the techniques of this disclosure may be implemented in other contexts (e.g., neurological, orthopedic, etc.). In some examples, one or more of medical device(s) 6 may be configured to perform deep brain stimulation (DBS), spinal cord stimulation (SCS), pelvic stimulation, peripheral nerve stimulation, muscle stimulation, etc.

In addition, while certain example medical device(s) 6 are described as being insertable or implantable devices, the techniques of this disclosure are not so limited, and persons skilled in the art will understand that the techniques of this disclosure may be implemented with medical device(s) 6 that are not configured to be insertable or implantable, such as wearable devices or other external medical devices. In a non-limiting example, medical device(s) 6 may include wearable devices (e.g., smart watches, headsets, etc.) configured to obtain physiological data (e.g., activity data, heart rate, etc.) and transfer such data to computing device(s) 2, network 10, edge device(s) 12, etc. for subsequent utilization, in accordance with one or more of the various techniques of this disclosure.

Moreover, while certain example medical device(s) 6 are described as being electrical devices or electrically-active devices, the techniques of this disclosure are not so limited, and person skilled in the art will understand that, in some examples, medical device(s) 6 may include non-electrical or non-electrically-active devices (e.g., orthopedic implants, etc.). In any case, medical device(s) 6 may be configured to communicate medical data to computing device(s) 2, such as via a telemetry protocol, Radio-Frequency Identification (RFID) transmission, etc. As such, any medical device and/or computing device configured to communicate medical data may be configured to implement the techniques of this disclosure.

In some examples, medical device(s) 6 may be implanted subcutaneously in patient 4. Furthermore, in some examples, computing device(s) 2 may monitor subcutaneous impedance values obtained from medical device(s) 6. In some examples, at least one of medical device(s) 6 takes the form of the Reveal LINQ™ Insertable Cardiac Monitor (ICM), or another ICM similar to, e.g., a version or modification of, the LINQ™ ICM, developed by Medtronic, Inc., of Minneapolis, MN. In such examples, medical device(s) 6 may facilitate relatively longer-term monitoring of patients during normal daily activities.

In a non-limiting example, medical device(s) 6 may include an IMD that is configured to operate as a pacemaker, a cardioverter, and/or defibrillator, or otherwise monitor the electrical activity of the heart of patient 4. In some examples, medical device(s) 6 can provide pacing pulses to the heart of patient 4 based on the electrical signals sensed within the heart of patient 4.

In some examples, medical device(s) 6 may also provide defibrillation therapy and/or cardioversion therapy via electrodes located on at least one lead and/or a housing electrode. Medical device(s) 6 may detect arrhythmia of the heart of patient 4, such as fibrillation of ventricles, and deliver defibrillation therapy to the heart of patient 4 in the form of electrical pulses. In some examples, medical device(s) 6 may be configured to deliver a progression of therapies, e.g., pulses with increasing energy levels, until a fibrillation of the heart of patient 4 is stopped. In such examples, medical device(s) 6 detects fibrillation employing one or more fibrillation detection techniques known in the art.

In some examples, system 100 may be implemented in a setting that includes network 10 and/or edge device(s) 12. That is, in some examples, system 100 may operate in the context of network 10 and/or include one or more edge device(s) 12. In some instances, network 10 may include edge device(s) 12. Similarly, computing device(s) 2 may include functionality of edge device(s) 12 and thus, may also serve as one of edge device(s) 12.

In some examples, edge device(s) 12 include modems, routers, Internet of Things (IoT) devices or systems, smart speakers, screen-enhanced smart speakers, personal assistant devices, etc. In addition, edge device(s) 12 may include user-facing or client devices, such as smartphones, tablet computers, personal digital assistants (PDAs), and other mobile computing devices.

In examples involving network 10 and/or edge device(s) 12, system 100 may be implemented in a home setting, a hospital setting, or in any setting comprising network 10 and/or edge device(s) 12. The example techniques may be used with medical device(s) 6, which may be in wireless communication with one or more edge device(s) 12 and other devices not pictured in FIG. 1 (e.g., network servers).

In some examples, computing device(s) 2 may be configured to communicate with one or more of medical device(s) 6, edge device(s) 12, or network 10 operating a network service such as the Medtronic CareLink® Network developed by Medtronic, Inc., of Minneapolis, MN. In some examples, medical device(s) 6 may communicate, via Bluetooth®, with computing device(s) 2. In some instances, network 10 may include one or more of edge device(s) 12. Network 10 may be and/or include any appropriate network, including a private network, a personal area network, an intranet, a local area network (LAN), a wide area network, a cable network, a satellite network, a cellular network, a peer-to-peer network, a global network (e.g., the Internet), a cloud network, an edge network, a network of Bluetooth® devices, etc., or a combination thereof, some or all of which may or may not have access to and/or from the Internet. That is, in some examples, network 10 comprises the Internet. In an illustrative example, computing device(s) 2 may periodically transmit and/or receive various data items, via network 10, to and/or from one of medical device(s) 6, and/or edge device(s) 12.

In addition, computing device(s) 2 may be configured to connect to cellular base station transceivers (e.g., for 3G, 4G, LTE, and/or 5G cellular network access), and Wi-Fi™ access points, as those connections are available. In some examples, the cellular base station transceivers may have connections that provide access to network 10. These various cellular and Wi-Fi™ network connections can be managed by different third-party entities, referred to herein as "carriers."

In some examples, system 100 may include one or more databases (e.g., storage device 96) that store various medical data records, cohort data, image data. In such examples, server(s) 94 (e.g., one or more databases) may be managed or controlled by one or more separate entities (e.g., internet service providers (ISPs), etc.).

Computing device(s) 2 and/or edge device(s) 12 may be used to configure operational parameters for medical device(s) 6. In some examples, the user may use computing device(s) 2 as a programmer to program measurement parameters, stimulation programs, etc. Computing device(s) 2 may also be configured to program a therapy progression, select electrodes to deliver defibrillation pulses, select waveforms for a defibrillation pulse or stimulation pulse train, select or configure a fibrillation detection algorithm, etc. The user may also use computing device(s) 2 to program aspects of other therapies that may be provided by medical device(s) 6, such as cardioversion or pacing therapies. In some examples, the user may activate certain features of medical device(s) 6 by entering a single command via UI 22 of computing device(s) 2, such as depression of a single key or combination of keys of a keypad or a single point-and-select action with a pointing device. In addition, computing device(s) 2 may operate the interactive session of this disclosure, where the interactive session is loaded with the programming parameters. Computing device(s) 2 may utilize such data for determining physiological parameters and/or interrogation data that deviates from an expected value as expected from the programming parameters. Computing device(s) 2 may utilize an AI engine and/or ML model in order to determine such deviations (e.g., abnormalities), where AI engine and/or ML model may be trained on programming parameters and on abnormality data in order to determine correlations between such data items.

In some examples, computing device(s) 2 may be configured to retrieve data from medical device(s) 6. The retrieved data may include values of physiological parameters measured by medical device(s) 6, indications of episodes of arrhythmia or other maladies detected by medical device(s) 6, and physiological signals obtained by medical device(s) 6. In some examples, computing device(s) 2 may retrieve cardiac EGM segments recorded by computing device(s) 2, e.g., due to computing device(s) 2 determining that an episode of arrhythmia or another malady occurred during the segment, or in response to a request, from patient 4 or another user, to record the segment.

In some examples, the user may also use computing device(s) 2 to retrieve information from medical device(s) 6 regarding other sensed physiological parameters of patient 4, such as activity or posture. In some examples, edge device(s) 12 may interact with medical device(s) 6 in a manner similar to computing device(s) 2, e.g., to program medical device(s) 6 and/or retrieve data from medical device(s) 6.

Processing circuitry of system 100, e.g., of medical device(s) 6, computing device(s) 2, edge device(s) 12, and/or of one or more other computing devices (e.g., remote servers), may be configured to perform the example techniques of this disclosure for determining an abnormality status of patient 4 and/or of components of IMD 6. The processing circuitry, may be referred to herein in some instances as a system of processors or a system of processing circuitry. In some examples, the system of processing circuitry of system 100 obtains physiological parameters, images, medical device diagnostics, etc. to determine whether to provide an alert to patient 4 and/or a HCP.

In some examples, processing circuitry of system 100, e.g., of computing device(s) 2, may determine a projection of alteration characteristics of the particular location of the body projected over time based on one or more images, including but not limited to images before and/or after an implantation or explant procedure. The processing circuitry may compare a second set of alteration characteristics to the projection determined from a second set of images in order to identify a potential abnormality (e.g., infection, discharge, device migration, erosion, etc.) at the particular location of the body.

In some instances, processing circuitry of system 100, e.g., of computing device(s) 2, provides an alert to patient 4 and/or other users when combination of patient health data (e.g., implantation site images, ECG parameters, etc.), medical device diagnostic data, and indicates the onset of an abnormality. The alert may be an audible alert generated by medical device(s) 6 and/or computing device(s) 2, a visual alert generated by computing device(s) 2, such as a text prompt or flashing buttons or screen, or a tactile alert generated by medical device(s) 6 and/or computing device(s) 2 such as a vibration or vibrational pattern. Furthermore, the alert may be provided to other devices, e.g., via network 10. Several different levels of alerts may be used based on a severity of a potential infection detected in accordance with one or more of the various techniques disclosed herein.

In some instances, processing circuitry of system 100, e.g., of computing device(s) 2, provides an alert to patient 4 and/or other users when a combination of patient health data (e.g., implantation site images, ECG parameters, etc.), medical device diagnostic data, and indicates the onset of an abnormality. The process for determining when to alert patient 4 involves measuring an abnormality (e.g., severity or probability levels) against one or more threshold values and is described in greater detail below. The alert may be an audible alert generated by medical device(s) 6 and/or computing device(s) 2, a visual alert generated by computing device(s) 2, such as a text prompt or flashing buttons or screen, or a tactile alert generated by medical device(s) 6 and/or computing device(s) 2 such as a vibration or vibrational pattern. Furthermore, the alert may be provided to other devices, e.g., via network 10. Several different levels of alerts may be used based on a severity of a potential abnormality detected through the techniques disclosed herein.

Figure 2:
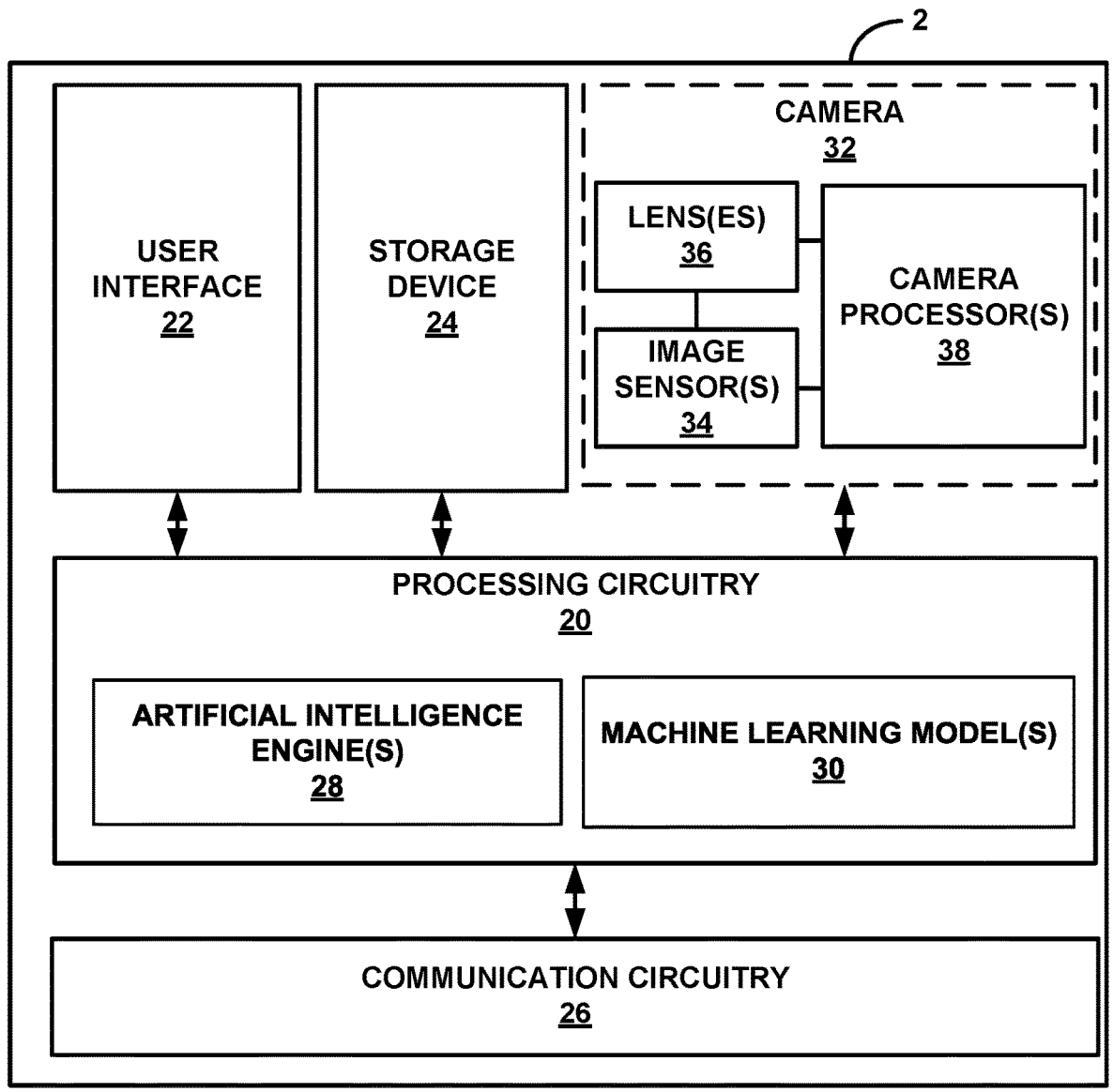
FIG. 2 is a functional block diagram illustrating an example configuration of an example computing device of FIG. 1, in accordance with one or more techniques disclosed herein.

FIG. 2 is a block diagram illustrating an example configuration of components of at least one computing device 2 of computing device(s) 2. In the example of FIG. 2, the at least one computing device 2 includes processing circuitry 20, communication circuitry 26, storage device 24, and UI 22.

Processing circuitry 20 may include one or more processors that are configured to implement functionality and/or process instructions for execution within computing device(s) 2. For example, processing circuitry 20 may be capable of processing instructions stored in storage device 24. Processing circuitry 20 may include, for example, microprocessors, a digital signal processors (DSPs), an application specific integrated circuits (ASICs), field-programmable gate arrays (FPGAs), complex programmable logic devices (CPLDs), or equivalent integrated or discrete logic circuitry, or a combination of any of the foregoing devices or circuitry. Accordingly, processing circuitry 20 may include any suitable structure, whether in hardware, software, firmware, or any combination thereof, to perform the functions ascribed herein to processing circuitry 20.

A trained ML model 30 and/or AI engine 28 may be configured to process and analyze the user input (e.g., images of the implantation site, patient status data, etc.), device parameters (e.g., accelerometer data), historical data of medical device (e.g., medical device 6), and/or physiological parameters, in accordance with certain examples of this disclosure where ML models are considered advantageous (e.g., predictive modeling, inference detection, contextual matching, natural language processing, etc.). Examples of ML models and/or AI engines that may be so configured to perform aspects of this disclosure include classifiers and non-classification ML models, artificial neural networks ("NNs"), linear regression models, logistic regression models, decision trees, support vector machines ("SVM"), Naïve or a non-Naïve Bayes network, k-nearest neighbors ("KNN") models, deep learning (DL) models, k-means models, clustering models, random forest models, or any combination thereof. Depending on the implementation, the ML models may be supervised, unsupervised or in some instances, a hybrid combination (e.g., semi-supervised). These models may be trained based on data indicating how users (e.g., patient 4) interact with computing device(s) 2. For example, certain aspects of the disclosure will be described using events or behaviors (such as clicking, viewing, or watching) with respect to items (e.g., wound images, cameras, videos, physiological parameters, etc.), for purposes of illustration only. In another example, these models and engines may be trained to synthesize data in order to identify abnormalities of patient 4 or medical device(s) 17 and to identify abnormalities of patient 4 or medical device(s) 17 from individual data items.

In a non-limiting example, patient 4 may exhibit difficulty with capturing images of the implantation site from various angles. This helpful data may be shared across a health monitoring or computing network so that optimal results may be presented to more than one user based on similar queries and user reactions to those queries. For brevity, these aspects may not be described with respect to events or behaviors regarding objects (e.g., data objects, such as search strings). In some examples, processing circuitry 40 may use ML algorithms (e.g., DL algorithms) to, for example, monitor a progression of a wound that is healing or predict that a potential infection is occurring, for example, with respect to an implant site of one of medical device(s) 17. In an illustrative and non-limiting example, AI engine(s) 28 and/or ML model(s) 30 may utilize a deep-neural network to localize an implantation site in an image and classify an abnormality status. In another example, AI engine(s) 28 and/or ML model(s) 30 may utilize Naïve Bayes and/or decision trees to synthesize (e.g., combine) data items and the analysis thereof (e.g., image analysis and ECG analysis) in order to obtain a comprehensive abnormality determination for patient 4 and include such comprehensive determinations in a report, such as for patient 4.

In another example, AI engine(s) 28 and/or ML model(s) 30 may be loaded with and trained on cohort parameters (e.g., age cohorts, IMD type cohorts, skin pigmentation cohorts, etc.) and combinations of cohort parameters. In such examples, AI engine(s) 28 and/or ML model(s) 30 may utilize historical reference interrogations for comparison when determining deviations from baseline parameters.

In addition, computing device(s) 2 may utilize different image processing algorithms and/or data synthesis algorithms, such as AI, ML, DL, digital signal processing, neural networks, and/or other techniques, depending on various different contexts and other various different resource constraints (e.g., processing power, network access, battery life, etc.).

In some examples, AI engine(s) 28 may be trained to analyze the gait of a patient with an orthopedic implant in place (e.g., by comparing video data representing the patient against cohort gait information). In such examples, computing device(s) 2 may deploy AI engine(s) 28 and/or ML model(s) 30 to analyze patient activity in order to determine the presence of a potential abnormality with patient 4 and/or medical device(s) 17 (e.g., IMD 6), such as when the gait of the patient appears abnormal to AI engine(s) 28 and/or ML model(s) 30 and/or when the gait of the patient changes over time so as to represent a developing or sudden abnormality of patient 4.

In addition, trained AI engine(s) 28 may be used to learn about patient 4 over time and learn about an implantation site of a patient 4. In this way, AI engine(s) 28 may provide a personalized detection algorithm for detected abnormalities for a particular implantation site. In such examples, AI engine(s) 28 may be loaded with and trained on cohort parameters, using historical reference interrogations or images for comparison. In this way, computing device(s) 2 may provide a solution using different algorithm approaches (e.g., AI, ML, DL, digital signal processing, neural networks, and/or other techniques) in order to personalize the site-check process for patient 4.

A user, such as a clinician or patient 4, may interact with one or more of computing device(s) 2 through UI 22. UI 22 includes a display (not shown), such as a liquid crystal display (LCD) or a light emitting diode (LED) display or other type of screen, with which processing circuitry 20 may present health- or device-related information, e.g., cardiac EGMs, indications of detections of impedance changes, temperature changes, etc. In addition, UI 22 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through UI 22 presented by processing circuitry 20 of computing device(s) 2 and provide input. In one examples, UI 22 may allow a user to rotate images and adjust zoom levels using a touch screen of computing device 2 (e.g., pinch-to-zoom, gestures, gaze tracking, etc.). In addition, UI 22 may allow the user to control camera parameters, such as to select a forward or rear facing camera, lighting, zoom levels, focus levels, contrast, etc., such that the user may capture images according to the camera parameters. In another example, computing device(s) 2 may automatically adjust such parameters, with or without initial input from the user.

In some examples, computing device(s) 2 may include an imaging device. In an illustrative example, computing device(s) 2 may include a camera 32 or multiple cameras 32 (e.g., digital cameras), as example imaging device(s). As shown in FIG. 2, camera 32 may refer to a collective device including one or more image sensor(s) 34, one or more lens(es) 36, and one or more camera processor(s) 38. In some examples, processing circuitry 20 may include camera processor(s) 38.

In some examples, computing device(s) 2 may include an imaging device, such as a camera 32. Camera 32 may be a digital camera built into computing device(s) 2. In some examples, camera 32 may be separate from computing device(s) 2. In such examples, camera 32 may communicate imaging data to computing device(s) 2 and/or other computing device (e.g., edge device(s) 2). In some examples, computing device(s) 2 may include a charge-coupled device (CCD) chip. The CCD chip may be configured to operate in a spectral response analysis mode using flash as an excitation (e.g., white light) light source. In such examples, computing device(s) 2 may employ a CCD chip in order to analyze an image of an implantation site. In one example, computing device(s) 2 may employ a CCD chip to provide separate color filtering analysis in different light wavelength to better detect redness and swelling in different skin tones. That is, computing device(s) 2 may perform a color filtering on the images in order to identify an abnormality from one or more image(s). In another example, computing device(s) 2 may perform a color filtering on an image in order to identify an abnormality from one or more image(s). In an illustrative example, computing device(s) 2 may perform, in accordance with one or more of the various techniques of this disclosure, regional comparison of bodily zones for differentiating an implantation site from another area of the body and for different skin types (e.g., skin tones).

In some examples, computing device(s) 2 may use camera 32 to image an implantation site of patient 4. In such examples, a storage device 24 of computing device 2 may store image data (e.g., still-images, etc.). In such instances, processing circuitry, such as processing circuitry 20 of computing device 2 and/or processing circuitry 64 (FIG. 3) of edge device(s) 12, may be in communication with storage device 24.

In some examples, processing circuitry, e.g., processing circuitry 20, in some instances, may determine a projection of alteration characteristics of the particular location of the body of patient 4 projected over time based on one or more images, including but not limited to images before and/or after an implantation or explant procedure. Processing circuitry 20 may compare a second set of alteration characteristics to the projection determined from a second set of images in order to identify a potential abnormality (e.g., infection, discharge, device migration, erosion, etc.) at the particular location of the body of patient 4. The images may be captured by one or more cameras 32, where cameras 32 may or may not be separate from computing device 32. Processing circuitry 20 may, in some instances, include one or more of camera processor(s) 38 (e.g., image signal processor). In another example, camera processor(s) 38 may be separate from processing circuitry 20 and/or included in a separate computing device 2, server(s) 94, edge device(s) 12, etc.

In some examples, multiple cameras 32 may be included with a single one of computing device(s) 2 (e.g., a mobile phone having one or more front facing cameras and one or more rear facing cameras). In some examples, computing device(s) 2 may include a first camera 32 having one or more image sensors 34 and one or more lenses 36, and a second camera 32 having one or more image sensors 34 and one or more lenses 36, etc. It should be noted that while some example techniques herein may be discussed in reference to frames received from a single camera (e.g., from a single image sensor), the techniques of this disclosure are not so limited, and a person of skill in the art will appreciate that the techniques of this disclosure may be implemented for any type of camera 32 and combination of cameras 32, such as a combination of cameras 32 that may be included with computing device(s) 2 or otherwise, communicatively coupled to computing device(s) 2. In some examples, image sensor(s) 34 represent one or more image sensors 34 that may include image-sensor processing circuitry. In some examples, image sensor(s) 34 include an array of pixel sensors (e.g., pixels) for capturing representations of light.

While shown as being optionally included with computing device(s) 2 (e.g., via dashed lines), the techniques of this disclosure are not so limited, and in some instances, camera 32 may be separate from computing device(s) 2, such as a stand-alone camera device or separate camera system. In any case, camera 32 may be configured to capture an image of an implantation site and transfer the image data to processing circuitry 20 via camera processor(s) 38. In some examples, camera 32 may be configured to achieve various zoom levels. In one example, camera 32 may be configured to perform cropping and/or scaling techniques to achieve a particular zoom level. In some examples, camera 32 may be configured to manipulate an output from image sensor(s) 34 and/or manipulate lens(es) 36 in order to achieve the particular zoom level.

In some examples, computing device(s) 2 may include audio circuitry (not shown) for providing audible notifications, instructions or other sounds to the user, receiving voice commands from the user, or both. In some examples, computing device(s) 2 may provide audible notifications indicating to a user a direction to proceed through UI 22 and/or to the virtual check-in process. In addition, computing device(s) 2 may provide audible notifications that indicate when a task is complete, such as when an authentication task (e.g., successful login), when an ECG measurement task is complete, or when any other task is complete. In another example, computing device(s) 2 may provide different audible notifications depending on particular outcomes. In one example, computing device(s) 2 may provide a quiet notification when the outcome of the interactive session is such that no follow-up appointment is warranted (e.g., no potential infection, device operating correctly, good physiological parameters, etc.), whereas computing device(s) 2 may provide a louder notification when the outcome of the interactive session indicates that a follow-up appointment is advised. In one example, computing device(s) 2 may provide an audible notification when the possibility of one or more abnormalities is identified. In another example, computing device(s) 2 may provide an audible notification upon identifying a collective abnormality (e.g., following a synthesis of data). In an illustrative example, computing device(s) 2 may determine a collective abnormality based on an identified potential abnormality at the implantation site and based on an abnormality of a physiological parameter (e.g., an ECG abnormality). In some instances, computing device(s) 2 may nevertheless determine the presence of a potentially health-threatening abnormality when no abnormality is identified in one subsession (e.g., an implantation site abnormality) but that an abnormality is identified in another subsession (e.g., an IMD abnormality), such that an analysis of the at least two subsession indicates that there is or is not an abnormality that warrants a follow-up appointment advisement. In addition, computing device(s) 2 may provide different audible notifications following each subsession and then again, following the completion of all proscribed subsessions (e.g., two subsessions, three subsessions, etc.).

Communication circuitry 26 may include any suitable hardware, firmware, software or any combination thereof for communicating with another device, such as medical device(s) 6. Under the control of processing circuitry 20, communication circuitry 26 may receive downlink telemetry from, as well as send uplink telemetry to, medical device(s) 6, or another device. Communication circuitry 26 may be configured to transmit or receive signals via inductive coupling, electromagnetic coupling, NFC, RF communication, Bluetooth®, Wi-Fi™, or other proprietary or non-proprietary wireless communication schemes. Communication circuitry 26 may also be configured to communicate with devices other than medical device(s) 6 via any of a variety of forms of wired and/or wireless communication and/or network protocols. In some examples, computing device(s) 2 may perform telemetry selection through a sweep (e.g., TelC, TelB, TelM, Bluetooth®, etc.).

Storage device 24 may be configured to store information within computing device(s) 2 during operation. Storage device 24 may include a computer-readable storage medium or computer-readable storage device. In some examples, storage device 24 includes one or more of a short-term memory or a long-term memory. Storage device 24 may include, for example, read-only memory (ROM), random access memory (RAM), non-volatile RAM (NVRAM), Dynamic RAM (DRAM), Static RAM (SRAM), magnetic discs, optical discs, flash memory, forms of electrically-erasable programmable ROM (EEPROM) or erasable programmable ROM (EPROM), or any other digital media.

In some examples, storage device 24 is used to store data indicative of instructions for execution by processing circuitry 20. In addition, storage device 24 may store image data and/or supplemental image data. In some examples, storage device 24 may store frames of image data. That is, storage device 24 may store one or more images. In some examples, storage device 24 may store one or more images of a body of patient 4 (e.g., implantation site images, skin images for skin color analytics, skin surfaces proximate lead routings, etc.), physiological parameter images (e.g., ECG images), etc. Storage device 24 may be used by software or applications running on computing device(s) 2 to temporarily store information during program execution. Storage device 24 may also store historical medical device data, historical patient data, timing information (e.g., number of days since implantation of an IMD, number of days since a particular physiological parameter has been above a certain threshold, etc.), AI and/or ML training sets, image data, etc.

Data exchanged between computing device(s) 2, edge device(s) 12, network 10, and medical device(s) 6 may include operational parameters of medical device(s) 6. Computing device(s) 2 may transmit data, including computer-readable instructions, to medical device(s) 6. Medical device(s) 6 may receive and implement the computer-readable instructions. In some examples, the computer-readable instructions, when implemented by medical device(s) 6, may control medical device(s) 6 to change one or more operational parameters, export collected data, etc. In an illustrative example, processing circuitry 20 may transmit an instruction to medical device(s) 6 which requests medical device(s) 6 to export collected data (e.g., ECGs, impedance values, etc.) to computing device(s) 2, edge device(s) 12, and/or network 10. In turn, computing device(s) 2, edge device(s) 12, and/or network 10 may receive the collected data from medical device(s) 6 and store the collected data, for example, in storage device 24. In addition, processing circuitry 20 may transmit an interrogation instruction to medical device(s) 6 which requests medical device(s) 6 to export operational parameters (e.g., battery, impedance, pulse width, pacing %, etc.).

In some examples, computing device(s) 2 may be coupled to external electrodes, or to implanted electrodes via percutaneous leads. In such examples, computing device(s) 2 may receive, from medical device(s) 6, and monitor physiological parameters, ECGs, etc., according to one or more techniques disclosed herein.

In the example illustrated in FIG. 2, processing circuitry 20 is configured to perform the various techniques described herein, such as the techniques described with reference to FIGS. 5-22. To avoid confusion, processing circuitry 20 is described as performing the various processing techniques proscribed to computing device(s) 2, but it should be understood that at least some of these techniques may also be performed by other processing circuitry (e.g., processing circuitry 40 of medical device(s) 17 (FIG. 4), processing circuitry 98 of server(s) 94, processing circuitry 64 of edge device(s) 12, etc.). In an illustrative example, processing circuitry 20 may capture image(s) of an implantation site, obtain other data items, output images and/or other data items, for infection detection, to an analysis platform, determine, based on the images and other data items, presence of potential abnormality (e.g., an infection), output a summary of an implantation status including potential abnormality information, and in some instances, transmit the summary of the implantation status including the potential infection information to another device. In this example, the analysis platform may be a separate program that processing circuitry 20 executes. In another example, the analysis platform may be a separate program that other processing circuitry from the system of processors executes instead.

Figure 3:
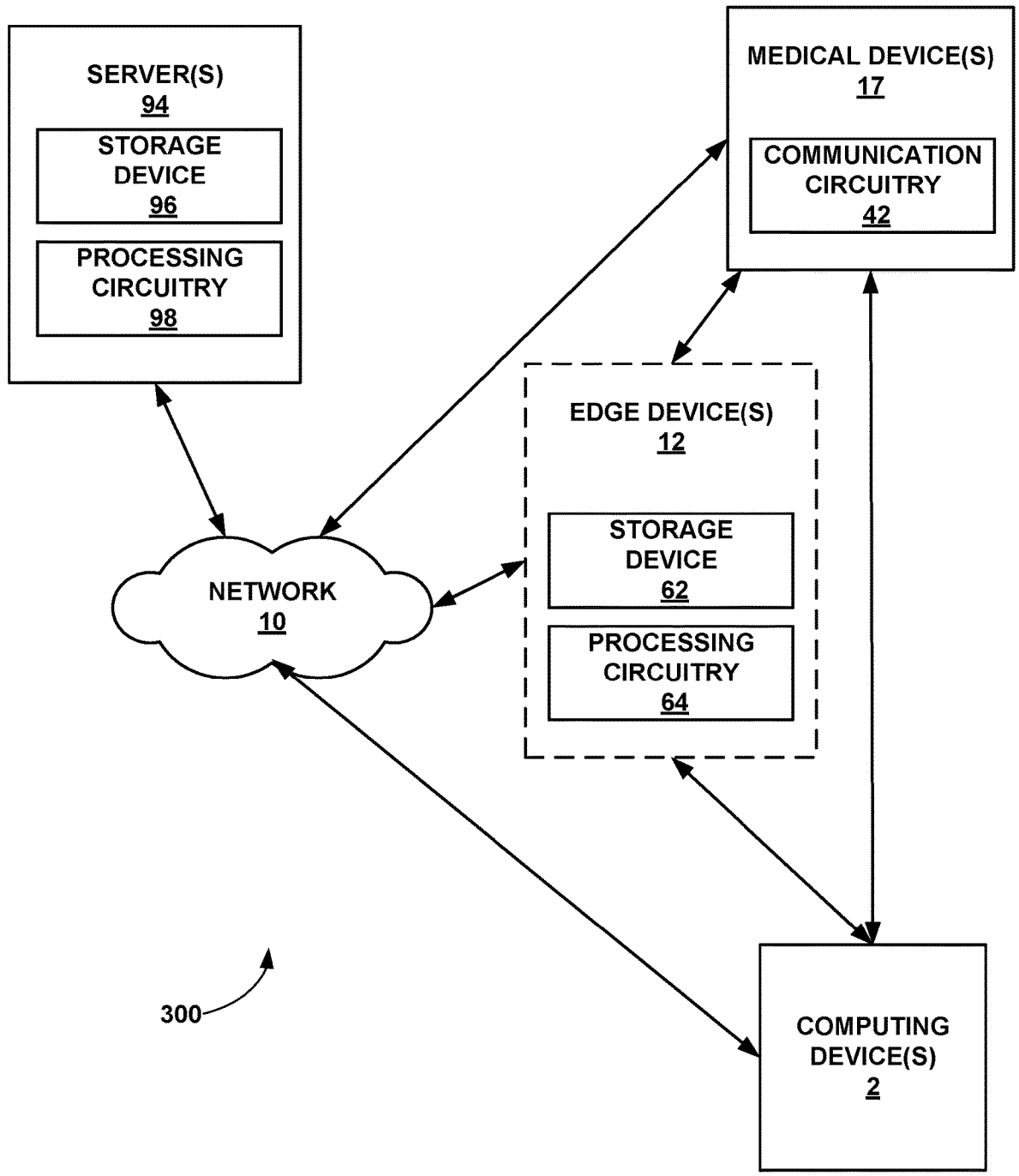
FIG. 3 is a block diagram illustrating an example network system that includes example computing device(s) of FIG. 1 or 2, a network, edge device(s), and server(s), in accordance with one or more techniques disclosed herein.

FIG. 3 is a block diagram illustrating an example system 300 that includes one or more example computing device(s) 2, one or more medical device(s) 17, network 10, one or more edge device(s) 12, and one or more server(s) 94, in accordance with one or more techniques disclosed herein. In some examples, system 300 is an example of system 100 described with reference to FIG. 1. In another example, system 300 illustrates an example network system that hosts monitoring system 100. In some examples, medical device(s) 17 may be an example of medical device(s) 6 of FIG. 1. That is, medical device(s) 17 may include an IMD, CIED, etc., similar to that as described with reference to FIG. 1. In addition, medical device(s) 17 may include non-implantable medical devices, including wearable medical devices (e.g., smart watches, wearable defibrillators, etc.).

Medical device(s) 17 may be configured to transmit data, such as sensed, measured, and/or determined values of physiological parameters (e.g., heart rates, impedance measurements, fluid indices, respiratory rate, activity data, cardiac electrograms (EGMs), historical physiological data, blood pressure values, etc.), to edge device(s) 12, computing device(s) 2 and/or an access point (e.g., gateway). In some examples, medical device(s) 17 may be configured to determine multiple physiological parameters. For example, medical device(s) 17 may include medical device(s) 6 (e.g., an IMD) configured to determine respiration rate values, subcutaneous tissue impedance values, EGM values, etc. Edge device(s) 12 and/or an access point device may then communicate, via network 10, the retrieved data to server(s) 94.

In some examples, medical device(s) 17 may transmit data over a wired or wireless connection to server(s) 94, edge device(s) 12, or computing device(s) 2. For example, server(s) 94 may receive data from medical device(s) 17 (e.g., IMD(s) 6, wearable devices, etc.) or from edge device(s) 12. In another example, edge device(s) 12 may receive, via network 10, data from server(s) 94. In some examples, edge device(s) 12 may receive, via network 10 or via a wired or wireless connection, data from medical device(s) 17. In such examples, edge device(s) 12 may determine the data received from server(s) 94, medical device(s) 17, or computing device(s) 2. In some examples, edge device(s) 12 may store the data to a storage device 62 internal to edge device(s) 12. Processing circuitry 64 of edge device(s) 12 may also include AI engines and/or ML models, such as the AI engines and ML models described with reference to FIG. 2.

In this example, medical device(s) 17 may use communication circuitry 42 to communicate with one of edge device(s) 12 via a first wireless connection. In some examples, medical device(s) 17 may use communication circuitry 42 to communicate with an access point via a second wireless connection. The access point may include a device that connects to network 10 via any of a variety of connections, such as telephone dial-up, digital subscriber line (DSL), or cable modem connections. In some examples, an access point may be coupled to network 10 through different forms of connections, including wired or wireless connections. In some examples, one of computing device(s) 2 may serve as an access point for network 10. For example, a user device, such as a tablet or smartphone, may be co-located with patient 4 and may be configured to serve as an access point. In any case, computing device(s) 2, edge device(s) 12, and server(s) 94 are interconnected and may communicate with each other through network 10.

Medical device(s) 17, edge device(s) 12, and/or computing device(s) 2 may be configured to communicate, via various connections, over network 10 with remote computing resources (e.g., server(s) 94). The data network (e.g., network 10) may be implemented by server(s) 94 (e.g., data servers, remove servers, analytic servers, etc.). In an example, server(s) 94 may include a data server configured to store data and/or perform computations based on the data. In another example, server(s) 94 may include a data server configured to store data (e.g., a database) and send data to another one of server(s) 94 for data analytics, image processing, or other data computations, in accordance with one or more of the various techniques of this disclosure. In some examples, server(s) 94 may be implemented on one or more host devices, such as blade servers, midrange computing devices, mainframe computers, desktop computers, or any other computing device configured to provide computing services and resources. Protocols and components for communicating via the Internet or any of the other aforementioned types of communication networks are known to those skilled in the art of computer communications and thus, need not be described in more detail herein.

In some examples, one or more of medical device(s) 17 may serve as or include server(s) 94. That is, medical device(s) 17 may include enough storage capacity or processing power to perform the techniques disclosed herein on a single one of medical device(s) 17 or on a network of medical device(s) 17 coordinating tasks via network 10 (e.g., over a private or closed network). In some examples, one of medical device(s) 17 may include at least one of server(s) 94. For example, a portable/bedside patient monitor may be configured to serve as one of server(s) 94, as well as serving as one of medical device(s) 17 configured to obtain physiological parameter values from patient 4.

In some examples, server(s) 94 may communicate with each of medical device(s) 17, via a wired or wireless connection, to receive physiological parameter values from medical device(s) 17 and/or device interrogation data from medical device(s) 17. In a non-limiting example, physiological parameter values and/or device interrogation data may be transferred from medical device(s) 17 to server(s) 94 and/or to edge device(s) 12. Server(s) 94 and/or edge device(s) 12 may perform analysis on the data to determine the presence of an abnormality at an implantation site (e.g., at a location of the body of patient 4 in which one or more IMD components coincide). Server(s) 94 and/or edge device(s) 12 may transmit, via communication circuitry, a result of the analysis to computing device(s) 2 for display and/or further processing.

In some examples, server(s) 94 may be configured to provide a secure storage site for data that has been collected from medical device(s) 17, edge device(s) 12, and/or computing device(s) 2. In some instances, server(s) 94 may comprise a database that stores medical- and health-related data. For example, server(s) 94 may comprise a cloud server or other remote server that stores data collected from medical device(s) 17, edge device(s) 12, and/or computing device(s) 2. In some cases, server(s) 94 may assemble data in web pages or other documents for viewing by trained professionals, such as clinicians, via computing device(s) 2. In the example illustrated by FIG. 3, server(s) 94 includes a storage device 96 (e.g., to store data retrieved from medical device(s) 17) and processing circuitry 98. As described with reference to FIG. 2, computing device(s) 2 may similarly include a storage device and processing circuitry.

Processing circuitry 98 may include one or more processors that are configured to implement functionality and/or process instructions for execution within server(s) 94. For example, processing circuitry 98 may be capable of processing instructions stored by storage device 96. Processing circuitry 98 may include, for example, microprocessors, DSPs, ASICs, FPGAs, or equivalent integrated or discrete logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server(s) 94 and/or the processing circuitry of computing device(s) 2 may implement any of the techniques described herein to analyze physiological parameters received from medical device(s) 17, e.g., to determine a healing progression of patient 4 or a health of medical device(s) 17.

Storage device 96 may include a computer-readable storage medium or computer-readable storage device. In some examples, storage device 96 includes one or more of a short-term memory or a long-term memory. Storage device 96 may include, for example, ROM, RAM, NVRAM, DRAM, SRAM, magnetic discs, optical discs, flash memory, forms of EEPROM or EPROM, or any other digital media. In some examples, storage device 96 is used to store data indicative of instructions for execution by processing circuitry 98.

In some examples, one or more of computing device(s) 2 may be a tablet or other smart device located with a clinician (or other HCP), by which the clinician may program, receive alerts from, and/or interrogate medical device(s) 17. For example, the clinician may access data collected by medical device(s) 17 through computing device 2, such as when patient 4 is in between clinician visits to check on a status of a medical condition. In some examples, computing device(s) 2 may transmit data regarding images, infection or other abnormality indications, training sets, ML models, IMD information, patient identification data, authentication data, etc. to one or more other computing device(s) 2, to edge device(s) 12, and/or to server(s) 94. Likewise, computing device(s) 2 may receive similar information.

In further examples, computing device 2 may generate an alert to patient 4 (or relay an alert determined by medical device(s) 17, edge device(s) 12, or server(s) 94) based on an abnormality determined from a combination of data items, which may enable patient 4 proactively to seek medical attention prior to receiving instructions for a medical intervention. In the example illustrated by FIG. 3, server(s) 94 includes a storage device 96 (e.g., to store data retrieved from medical device(s) 17) and processing circuitry 98. As described with reference to FIG. 2, computing device(s) 2 may similarly include a storage device and processing circuitry.

In some examples, the clinician may enter instructions for a medical intervention for patient 4 into an application executed by computing device 2, such as based on a status of a patient condition determined by another one of computing device(s) 2, medical device(s) 17, edge device(s) 12, server(s) 94, or any combination thereof, or based on other patient data known to the clinician. The patient condition may include an implant status, such as a potential infection at an implantation site of the implant. Computing device 2 of a user may receive the instructions, via network 10. In return, computing device 2 may display a message on a display device indicating the medical intervention message.

In some examples, one of computing device(s) 2 may transmit instructions for medical intervention to another one of computing device(s) 2 located with patient 4 or a caregiver of patient 4. For example, such instructions for medical intervention may include an instruction to change a drug dosage, timing, or selection, to schedule a visit with the clinician, or to seek medical attention. In this manner, patient 4 may be empowered to take action, as needed, to address his or her medical status, which may help improve clinical outcomes for patient 4.

Figure 4:
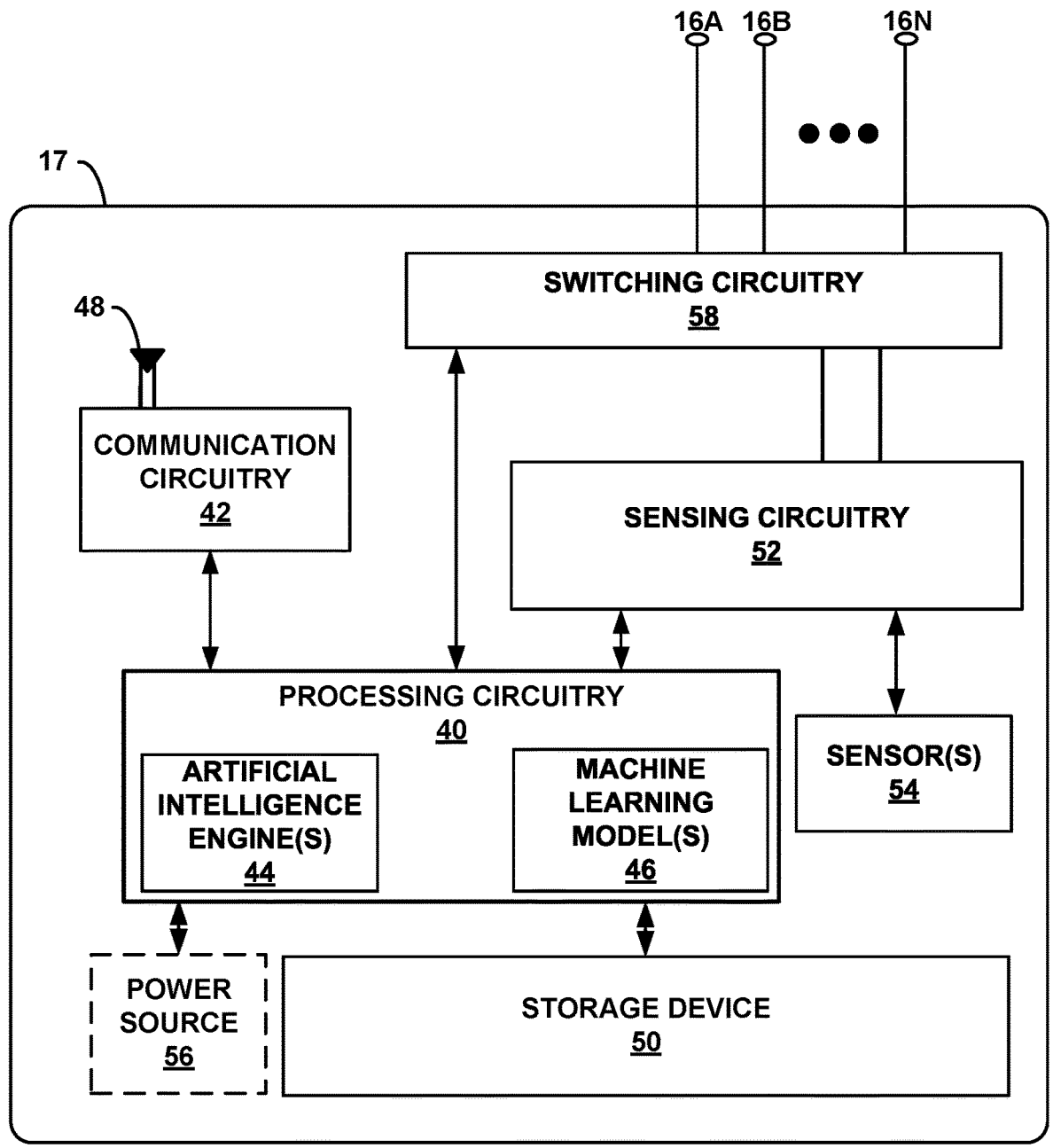
FIG. 4 is a functional block diagram illustrating an example configuration of a medical device of FIGS. 1 and/or 3, in accordance with one or more techniques disclosed herein.

FIG. 4 is a functional block diagram illustrating an example configuration of one or more of medical device(s) 17, in accordance with one or more techniques disclosed herein. In the illustrated example, medical device(s) 17 include processing circuitry 40, a storage device 50, and communication circuitry 42. Additionally, medical device(s) 17 may, in some examples, include one or more electrodes 16, antenna(e) 48, sensing circuitry 52, switching circuitry 58, sensor(s) 62, and power source 56. As previously stated, medical device(s) 17 may be an example of one of medical device(s) 6 of FIG. 1. That is, medical device(s) 17 may include an IMD, CIED, etc., similar to medical device(s) 6 shown and described with reference to FIG. 1. In another example, medical device(s) 17 may include a non-implanted medical device, such as a wearable medical device, a medical workstation cart, etc.

In some examples, one of medical device(s) 17 may be a medical device implanted in patient 4, whereas another one of medical device(s) 17 may include camera 32, and as such, may perform one or more of the various techniques of this disclosure. That is, one of medical device(s) 17 may, via camera 32, capture images of a body of patient 4 (e.g., an implantation site of patient 4), in accordance with one or more of the various techniques of this disclosure.

Processing circuitry 40 may include fixed function circuitry and/or programmable processing circuitry. Processing circuitry 40 may include any one or more of microprocessors, a controllers, DSPs, ASICs, FPGAs, or equivalent discrete or analog logic circuitry. In some examples, processing circuitry 40 may include multiple components, such as any combination of one or more microprocessors, one or more controllers, one or more DSPs, one or more ASICs, or one or more FPGAs, as well as other integrated or discrete integrated logic circuitry. The functions attributed to processing circuitry 40 herein may be embodied as software, firmware, hardware or any combination thereof.

In some examples, processing circuitry 40 may include AI engine(s) 44 and/or ML model(s) 46. AI engine(s) 44 and ML model(s) 46 may be similar to those AI engine(s) and ML model(s) described with reference to FIG. 2. In one example, ML model(s) 46 may include one or more DL models that are trained, for example, on various physiological parameter data, such as ECG data.

In the illustrated and non-limiting example of FIG. 4, medical device(s) 17 includes a plurality of electrodes 16A-16N (collectively, "electrodes 16"). Electrode(s) 16 may be referred to in some instances herein as a plurality of "electrode(s) 16," while in other instances may be referred to simply as "electrode 16," where appropriate. Electrodes 16 may be disposed within one bodily layer of patient 4, whereas at least one other electrode 16 may be disposed within another bodily layer of patient 4. In some examples, medical device(s) 17 may sense, via electrodes 16, electrical signals attendant to the depolarization and repolarization of the heart of patient 4.

In some examples, electrodes 16 may be configured for implantation outside of a thorax of patient 4. In some examples, the housing of medical device(s) 17 may be used as an electrode in combination with electrodes located on leads. In some examples, medical device(s) 17 may be configured to measure impedance changes within the interstitial fluid of patient 4, ECG morphology changes, etc. For example, medical device(s) 17 may be configured to receive one or more signals indicative of a subcutaneous tissue impedance. In some examples, computing device(s) 2 may utilize such information to determine an abnormality of IMD 6, such as a device migration abnormality, that computing device(s) 2 may use to determine a likelihood of an abnormality (e.g., an infection) at an implantation site based on images obtained of the implantation site.

One or more of electrodes 16 may be coupled to at least one lead. In some examples, medical device(s) 17 may employ electrodes 16 in order to provide sensing and/or pacing functionalities. The configurations of electrodes 16 may be unipolar or bipolar. Sensing circuitry 52 may be selectively coupled to electrodes 16 via switching circuitry 58, e.g., to select the electrodes 16 and polarity, referred to as the sensing vector, used to sense impedance and/or cardiac signals, as controlled by processing circuitry 40. Sensing circuitry 52 may sense signals from electrodes 16, e.g., to produce a cardiac EGM or subcutaneous ECG, in order to facilitate monitoring the post-implant status of IMD 6. Sensing circuitry 52 also may monitor signals from sensors 54, which may include one or more accelerometers, pressure sensors, temperature sensors, and/or optical sensors, as examples. In some examples, sensing circuitry 52 may include one or more filters and amplifiers for filtering and amplifying signals received from electrodes 16 and/or sensors 54. In an illustrative example, computing device 2 may obtain temperature sensor data from IMD 6 to determine the likelihood of a device pocket infection in view of images obtained of an implantation site of IMD 6 because a temperature sensor increase at the IMD 6 that occurs prior to a temperature increase at other locations of patient 4 may indicate a device pocket infection. In some examples, computing device 2 may obtain a thermal image of the implantation site and/or areas adjacent the implantation site in order to compare the thermal image to the temperature data and determine the presence of an abnormality at an implantation site, such as where a temperature increase at the IMD 6 leads a temperature increase at other exterior locations of patient 4.

In some examples, processing circuitry 40 may use switching circuitry 58 to select, e.g., via a data/address bus, which of the available electrodes are to be used to obtain various measurements. Switching circuitry 58 may include a switch array, switch matrix, multiplexer, transistor array, microelectromechanical switches, or any other type of switching device suitable to selectively couple sensing circuitry 58 to selected electrodes. In some examples, sensing circuitry 52 includes one or more sensing channels, each of which may comprise an amplifier. In response to the signals from processing circuitry 40, switching circuitry 58 may couple the outputs from the selected electrodes to one of the sensing channels.

In some examples, one or more channels of sensing circuitry 52 may include R-wave amplifiers that receive signals from electrodes 16. In some examples, the R-wave amplifiers may take the form of an automatic gain-controlled amplifier that provides an adjustable sensing threshold as a function of the measured R-wave amplitude. In addition, in some examples, one or more channels of sensing circuitry 52 may include a P-wave amplifier that receives signals from electrodes 16. Sensing circuitry 52 may use the received signals for pacing and sensing in the heart of patient 4. In some examples, the P-wave amplifier may take the form of an automatic gain-controlled amplifier that provides an adjustable sensing threshold as a function of the measured P-wave amplitude. Other amplifiers may also be used. In some examples, sensing circuitry 52 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter (ADC) for storage in storage device 50. Processing circuitry 40 may employ digital signal analysis techniques to characterize the digitized signals stored in storage device 50. In some examples, processing circuitry 40 may detect and classify cardiac arrhythmias from the digitized electrical signals. In some examples, computing device(s) 2 may obtain, via a physiological parameter subsession, physiological parameters (e.g., cardiac arrhythmia data) as part of a set of data items. In addition, computing device(s) 2 may obtain, via a device-check subsession, device performance parameters, such as amplifier performance, ADC performance, etc. as part of a set of data items comprising interrogation data items. In accordance with one or more of the various techniques of this disclosure, computing device(s) 2 may utilize such data items to elucidate and/or inform an analysis of images of an implantation site.

In some examples, medical device(s) 17 may include measurement circuitry having an amplifier design configured to switch in real-time and continuously between multiple and distinct measurement parameters. In addition, medical device(s) 17 may enable sensing circuitry 52 and/or switching circuitry 58 for short periods of time in order to conserve power. In one example, medical device(s) 17 may use an amplifier circuit, such as a chopper amplifier, according to certain techniques described in U.S. application Ser. No. 12/872,552 by Denison et al., entitled "CHOPPER-STABILIZED INSTRUMENTATION AMPLIFIER FOR IMPEDANCE MEASUREMENT," filed on Aug. 31, 2010, incorporated herein by reference in its entirety.

In some examples, medical device(s) 17 may operate as a therapy delivery device. In such examples, medical device(s) 17 may include leads. The leads may extend to any location within or proximate to a heart or in the chest of patient 4. In an illustrative and non-limiting example, one of medical device(s) 17 may include a single lead that extends from one of medical device(s) 17 into a right atrium or right ventricle, or two leads that extend into a respective one of a right atrium and a right ventricle.

In some examples, one of medical device(s) 17 may be configured to include sensing circuitry, such as sensing circuitry 52, and one or more sensor(s), such as sensor(s) 54. In addition, in some examples, one of computing device(s) 2 may be configured to also include sensing circuitry, such as sensing circuitry 52, and one or more sensor(s), such as sensor(s) 54. In one example, one of computing device(s) 2 and/or one of medical device(s) 17 may include a heart rate sensor, pulse sensor, photoplethysmogram (PPG) sensor, blood oxygen saturation (SpO$_2$) sensor, etc.

Sensing circuitry 52 may be implemented in one or more processors, such as in one or more processors of processing circuitry 40 of medical device(s) 17 or processing circuitry 20 of computing device(s) 2. Sensing circuitry 52 is, in the example of FIG. 4, shown in conjunction with sensor(s) 54. Similar to processing circuitry 20, 98, 40, 64 and other circuitry described herein, sensing circuitry 52 may be embodied as one or more hardware modules, software modules, firmware modules, or any combination thereof.

In some examples, at least one of medical device(s) 17 may include a sensor device, such as an activity sensor, heart rate sensor, a wearable device worn by patient 4, a temperature sensor, a chemical sensor, an impedance sensor, etc. The one or more other medical device(s) 17 may, in some examples, be an external device that is external to patient 4 relative to a body of patient 4 or relative to medical device(s) 17 implanted in patient 4. In any case, medical device(s) 17 may interface with one another via communication circuitry 42, and may, in some examples, interface, in a similar fashion, with computing device(s) 2, edge device(s) 12, etc.

In an illustrative and non-limiting example, computing device(s) 2 may obtain temperature sensor data obtained from temperature sensors on-board IMD 6 and may correlate such data with image data in order to predict a potential abnormality. In an example, computing device(s) 2 may correlate images with increase body temperature, either of patient 4 or IMD 6 in order to determine the presence of, for example, an infection at the implantation site. In another example, computing device(s) 2 may obtain chemistry data from the chemical sensor that may be indicative of lactate build and pH changes, which are leading indicators for abnormalities, such as infections, at an implantation site of IMD 6. Computing device(s) 2 may correlate such data in view of baseline values obtained, for example, prior to implantation of IMD 6. In an example, impedance monitoring may be useful in detecting device migration changes, but a number of days, such as 10 days may be useful to wait so as to allow the impedance to settle following an implantation event. In some examples, computing device(s) 2 may determine the impedance has settled to a baseline value prior to relying on impedance data to determine the presence of a potential abnormality.

In one example, computing device(s) 2 may utilize orientation information of the medical device(s) 17, as indicated by the accelerometer data, in order to adjust image processing parameters, for example, of computing device(s) 2. In one example, shadows may be formed based on the orientation of the medical device(s) 17 that affect the image processing techniques of this disclosure, such that the image processing algorithms may adjust the processing techniques based on information about where medical device(s) 17 is situated within patient 4. In such instances, computing device(s) 2 may receive information from medical device(s) 2, such as temperature data and/or orientation data, and utilize such information during an analysis of image data. That is, computing device(s) 2 may analyze the image data received via camera(s) 32 in view of information received from medical device(s) 2 in order accurately characterize a potential abnormality. In a non-limiting and illustrative example, computing device(s) 2 may be analyzing the image data in view of a set of reference images of an implantation site uploaded immediately following implantation, where the set of reference images may no longer align with a positional state of medical device(s) 2 due to movement of medical device(s) 2, and thus, computing device(s) 2 may adjust the image processing techniques in order to maintain a degree of accuracy while, computing device(s) 2 or another device, ultimately performs the abnormality analysis.

In one example, computing device 2 may determine, from physiological parameters obtained via a second subsession, an ECG change that indicates device migration and as such, increases the likelihood that a potential abnormality is being detected from the image data. In such instances, computing device 2 may analyze the image data using a bias toward detecting an abnormality or may include, in a post-implant report, a heightened likelihood (e.g., probability, confidence interval) that is based on the likelihood of a potential abnormality determined from the first and second set data items.

In another example, computing device 2 may determine an ECG signal and utilize the ECG signal to map to an orientation of IMD 6. In some examples, computing device 2 may utilize ECG morphology data to map to an orientation of IMD 6 by identifying deflections in an ECG (e.g., PQRST data) or by comparing the ECG morphology data against a population-wide or cohort database. When an ECG morphology indicates a shift from a baseline ECG of patient 4, then computing device(s) 2 may indicate a device migration abnormality. A device migration abnormality may be indicative of a potential infection abnormality. In such instances, when computing device(s) 2 is uncertain whether a potential infection from a set of images, computing device(s) 2 may bias the determination toward an identification of an abnormality in view of the ECG morphology data. In another example, computing device 2 may obtain, from one or more of medical device(s) 17 (e.g., IMD 6), lead impedance information. Similar to the above, computing device 2 may utilize IMD information (e.g., lead impedance information) as an additional input for abnormality detection and/or prediction.

Communication circuitry 42 may include any suitable hardware, firmware, software or any combination thereof for communicating with another device, such as edge device(s) 12, network computing device (e.g., server(s)), other medical device(s) 17 or sensors, and/or computing device(s) 2. Under the control of processing circuitry 40, communication circuitry 42 may receive downlink telemetry from, as well as send uplink telemetry to, edge device(s) 12 or another device with the aid of an internal or external antenna, e.g., antenna 48. In addition, processing circuitry 40 may communicate with a network computing device via network 10, such as the Medtronic CareLink® Network. Antenna 48 and communication circuitry 42 may be configured to transmit and/or receive signals via inductive coupling, electromagnetic coupling, NFC, RF communication, Bluetooth®, Wi-Fi™, or other proprietary or non-proprietary wireless communication schemes. In one example, processing circuitry 40 may provide data to be uplinked, via communication circuitry 42, to edge device(s) 12, computing device(s) 2, and/or other devices, via network 10. In an illustrative example, computing device(s) 2 may receive a signal (e.g., uplink data) from a particular one of medical device(s) 17 (e.g., IMD 6). In such examples, computing device(s) 2 may determine, from the signal, information relevant to patient 4 and/or the particular one of medical device(s) 17 (e.g., IMD 6). In one example, the information may include device information (e.g., IMD information) that corresponds to the particular one of medical device(s) 17 or that corresponds to a set of medical device(s) 17, where the set may include, in addition to one of IMD(s) 6, other paired medical device(s) 17 (e.g., wearable devices, etc.). In such examples, computing device(s) 2 may initiate a device interrogation session in which computing device(s) 2 receive signals from the particular one of medical device(s) 17 (e.g., IMD 6) indicative of device interrogation data (e.g., battery health, operating parameters, etc.).

In some examples, processing circuitry 40 may provide control signals using an address/data bus. In some examples, communication circuitry 42 may provide, via a multiplexer, data to processing circuitry 40, where the data is received externally via antenna 48. In some examples, medical device(s) 17 may transmit data to another device using a wired connection, such as a universal serial bus (USB) connection, ethernet connection over network 10 (e.g., a LAN), etc.

In some examples, processing circuitry 40 may send temperature data or other device interrogation data to edge device(s) 12 via communication circuitry 42. For example, medical device(s) 17 may send internal temperature measurements to edge device(s) 12, which are then analyzed by edge device(s) 12. In such examples, edge device(s) 12 performs the described processing techniques. Alternatively, medical device(s) 17 may perform the processing techniques and transmit the abnormality results to edge device(s) 12 for reporting purposes, e.g., for providing an alert to patient 4 or another user.

In some examples, storage device 50 includes computer-readable instructions that, when executed by processing circuitry 40, cause medical device(s) 17, including processing circuitry 40, to perform various functions attributed to medical device(s) 17 and processing circuitry 40 herein. Storage device 50 may include any volatile, non-volatile, magnetic, optical, or electrical media. For example, storage device 50 may include ROM, RAM, NVRAM, DRAM, SRAM, magnetic discs, optical discs, flash memory, forms of EEPROM or EPROM, or any other digital media. Storage device 50 may store, as examples, programmed values for one or more operational parameters of medical device(s) 17 and/or data collected by medical device(s) 17 for transmission to another device using communication circuitry 42. Data stored by storage device 50 and transmitted by communication circuitry 42 to one or more other devices may include electrocardiograms, cardiac EGMs (e.g., digitized EGMs), and/or impedance values, as examples.

The various components of medical device(s) 17 are coupled to power source 56, which may include a rechargeable or non-rechargeable battery. A non-rechargeable battery may be capable of holding a charge for several years, while a rechargeable battery may be charged from an outlet or other external charging device (e.g., inductive charging). In examples involving a rechargeable battery, the rechargeable battery may be charged on a daily, weekly, or annual basis, for example. In some examples, power source 56 may be separate from medical device(s) 17 and implanted in a separate implantation site of patient 4 that may be monitored for abnormalities, in accordance with one or more of the various techniques of this disclosure.

As described herein, medical device(s) 17 may include medical device 6 (e.g., IMD 6). In such examples, medical device(s) 17 may have a geometry and size designed for ease of implant and patient comfort. Examples of medical device(s) 17 described in this disclosure may have a volume of 3 cubic centimeters ($cm^3$) or less, 1.5 $cm^3$ or less, or any volume therebetween. In addition, medical device(s) 17 may include a proximal end and a distal end that are rounded to reduce discomfort and irritation to surrounding tissue once implanted under the skin of patient 4. An example configuration of a medical device 17 is described, as an example, in U.S. Patent Publication No. 2016/0310031, incorporated herein by reference in its entirety. Computing device(s) 2 may receive IMD information that include such configuration details of medical device 17 (e.g., IMD size, whether ends are rounded, length of elongated leads, if any, etc.). As described herein, computing device(s) 2 may utilize IMD information, such as IMD configuration, to train AI engine(s) 28 and/or ML models(s) 30 to provide an IMD-tailored abnormality assessment, in accordance with one or more of the various techniques of this disclosure.

Figure 5:
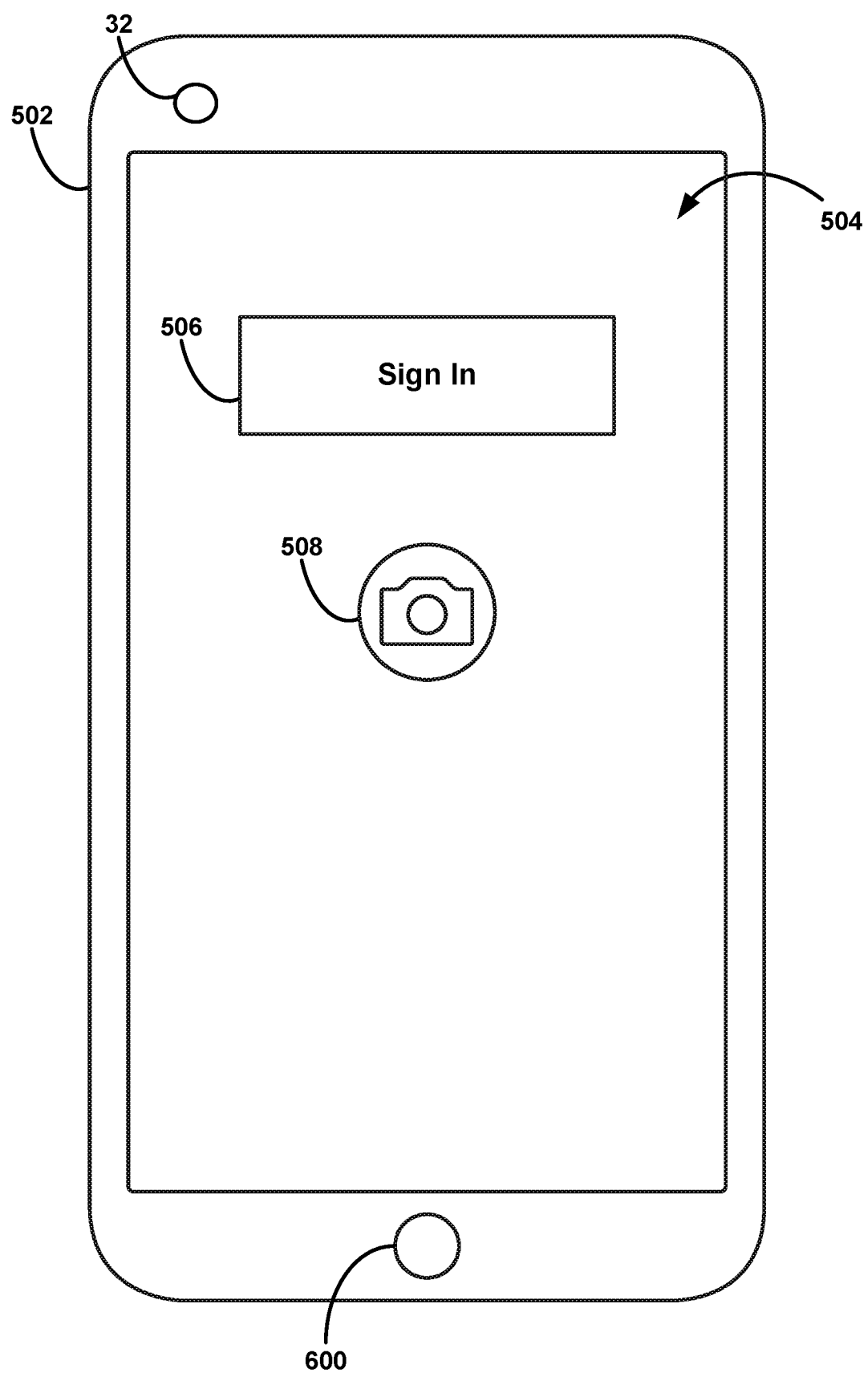
FIG. 5 is an example user interface (UI) visualization of an example computing device of FIG. 1, 2, or 3, in accordance with one or more techniques of this disclosure.

FIG. 5 is an example UI visualization of an example computing device 502, in accordance with one or more techniques of this disclosure. Computing device 502 may be an example of one of computing device(s) 2 described with reference to FIG. 1, 2, or 3. Computing device 502 may include one or more cameras 32, in accordance with one or more various techniques of this disclosure. As described herein, the one or more cameras 32 may be separate from computing device 502 in some examples. In the illustrative and non-limiting example of FIG. 5 and others illustrating computing device 502, computing device 502 may include a mobile handheld device (e.g., a tablet, smartphone, etc.). While illustrated as a mobile handheld device, the techniques of this disclosure are not so limited. It will be understood that the UI visualization elements may be employed using various other devices and in various other settings, such as in a virtual reality, augmented reality, or mixed reality setting. That is, a user may use cameras 32 of augmented reality headsets in order to image an implantation site of patient 4, as well as navigate one or more of the UIs of this disclosure.

In some examples, a UI visualization or interface, as described herein, may include a UI page or screen of the relevant UI (e.g., UI 22). In some examples, a user may use navigation buttons (e.g., back, next, scroll buttons, etc.) to navigate laterally (e.g., forward, backward, etc.) through various UI pages or screens. In some instances, the UI visualization may include a virtual reality and/or augmented reality visualization, such as when computing device 502 includes a VR, AR, or MR headset. That is, the UI visualization may be presented as an immersive UI program that a user may interact with in a virtual and/or augmented reality space. A person of skilled in the art will appreciate that, although shown as different pages of a UI, computing device 502 may similarly present, instead of UI pages on a screen of a handheld mobile device, VR UI elements that a user may, nevertheless, navigate in order to conduct an interactive session in accordance with the one or more of the various techniques of this disclosure or at least not inconsistent with the one or more of the various techniques of this disclosure.

In some examples, computing device 502 may present an interface 504 (e.g., via UI 22) that includes various sign-in options. In one example, interface 504 may include a sign in tile 506 or other sign in elements (e.g., camera icon 508). Computing device 502 may receive user input, as the user input relates to sign in tile 506, in order to invoke and/or initiate a virtual check-in interactive session, in accordance with one or more techniques of this disclosure.

In an illustrative example, interface 504 may include a camera icon that first initializes camera 32 for sign in purposes. Computing device 502 may receive images from camera 32 and authenticate the user from the received images. In some examples, computing device 502 may perform facial recognition or implantation site (e.g., wound) characteristics recognition. In some examples, patient 4 may tap computing device 502 to the implantation site for NFC or RFID authentication. That is, computing device 502 may receive NFC or RFID indications. Computing device 502 may use such indications to identify and/or authenticate the particular user. In any case, computing device 502 may load, from storage device 24, the interactive session through or based on a reading or scan of a barcode (e.g., a one-dimensional barcode, a two-dimensional barcode, Quick Response (QR) Code™, matrix barcode, etc.). In some instances, the barcode may be included with a flyer given to patient 4 at implant time or shortly before/after the implantation procedure.

In some examples, computing device 502 may use one of medical device(s) 17 to authenticate user. Medical device(s) 17, in this instance, may include a wearable device that is able to authenticate the user (e.g., patient 4, HCP, etc.). The wearable device may, in some instances, include a wristband that includes a barcode, RFID chip, etc. In such instances, the user could tap medical device 17 to computing device 502 or computing device 502 may otherwise scan medical device 17. In some instances, the tap could be a contactless tap, such as an air tap that maintains a small air gap between devices. In any case, in a non-limiting example, computing device 502 may receive the authenticating information from medical device 17 and authenticate the user, such as by allowing the user to proceed to a next interface of the interactive session.

In some examples, UI 22 may include a button 600 (e.g., a soft key, hard key, etc.) that serves as a sign-in element. That is, button 600 may include a multi-function button that provides various sign-in options. In one example, button 600 may include a fingerprint or other biometric scanner. Button 600 may be on the front, back, or on any other portion of computing device 502.

In some examples, computing device 502 may not present interface 504, such as following a first sign in from a user. In such examples, a user may select a "remember this device," "remember me," and/or "I am the only relevant user for this device." Computing device 502 may receive the user input and forego a sign-in interface for future sign-in events, accordingly. In some instances, a user may want to re-authenticate for each sign in, such as in cases where multiple IMD patients use the same computing device 502 for implantation site or other IMD monitoring.

Figure 6:
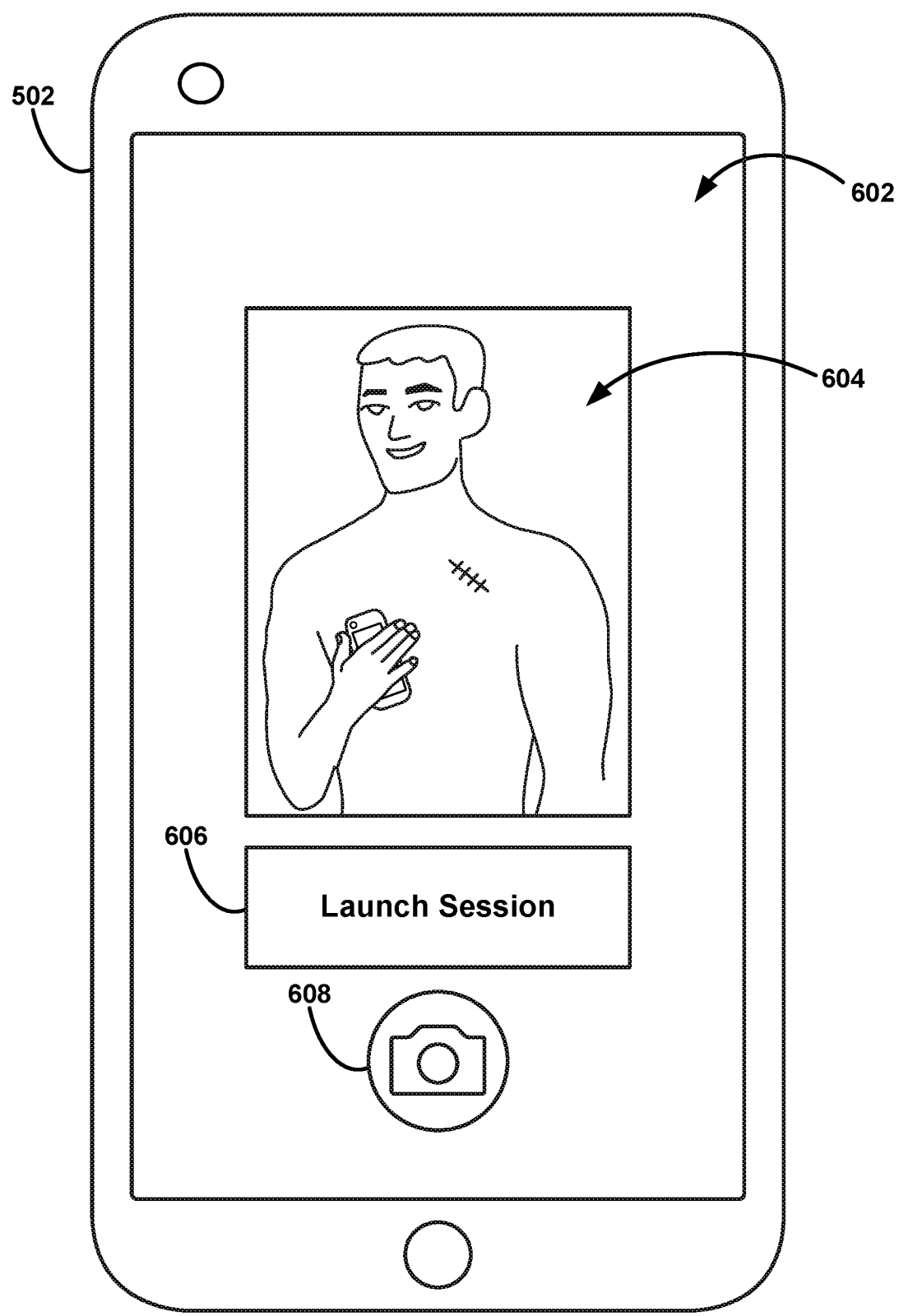
FIG. 6 is an UI visualization of an example launch-interactive-session interface, in accordance with one or more techniques of this disclosure.

FIG. 6 is an UI visualization of a launch session interface 602, in accordance with one or more techniques of this disclosure. In some instances, the launch session interface 602 may include a launch session icon 606 and/or a camera icon 608. Camera icon 608 may be similar to camera icon 508 except that, once already authenticated, camera icon 608 may function as a shortcut to launch a site-check subsession or other subsession of the virtual check-in process (e.g., the interactive reporting and/or check-in supersession). In such examples, computing device 502 may receive user input of camera icon 608, and in turn, computing device 502 may initialize an imaging device (e.g., camera 32) and launch a site-check subsession (e.g., a wound check subsession), as described with reference to FIGS. 15-19.

In some instances, launch session interface 602 may include a profile interface 604. Profile interface 604, in some examples, may include an image of patient 4, an image of one or more relevant implantation sites of patient 4, or both. In this way, patient 4 may enjoy an even more personalized experience with using the virtual check-in UI. In such examples, computing device 502 may access the images from storage device 24 or from another storage device, such as via network 10. In some examples, the images may be images from a previous site-check subsession.

In some examples, the virtual check in interactive session may be pushed to a device of patient 4, such as through cloud solutions. In such instances, computing device 502 may receive a push notification from edge device 12 or from another device (e.g., server(s) 94 via network 10). The push notification may, in some instances, originate from computing device 2 of another user, such as from computing device 2 of a HCP. In some instances, computing device 502 may receive a notification prompting a virtual check-in session based on a predetermined scheduling reminder. In such instances, an HCP may program a calendar timer that, when expired, causes computing device 502 to provide a push notification and/or automatically launch the virtual check-in session (e.g., an interactive reporting session). In some examples, computing device 502 may, upon determining a schedule trigger or a push notification (e.g., a HCP push), provide an instruction to a user to open (e.g., launch) a virtual check-in interactive session. In some instances, computing device 502 may automatically launch a virtual check-in interactive session upon determining the schedule trigger or the push notification. That is, computing device 502 may automatically present interface 504 of FIG. 5, interface 602 of FIG. 6, or in some cases, may, as a default, present interfaces similar to those described with reference to FIGS. 7-21. In some instances, computing device 502 may determine whether the user requires authentication first or not before presenting various other interfaces.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may be configured to determine identification data for patient 4. In an example, processing circuitry 20 may determine the identification data for patient 4. The identification data may include one or more of: biometric data, RFID data, NFC data, telemetry protocol data, user login information, authentication data, patient name or user name data, etc. In any case, a user may input identification data via computing device(s) 2 and/or via camera 32. In one example, computing device(s) 2 may include computing device 502 serving as a user check-in device. In such instances, computing device(s) 2 may determine identification data for patient 4 via input received via elements of interface 504 (e.g., via button 600, where button 600 includes a biometric scanner).

In some examples, patient 4 may provide authenticating data in order to gain access to perform the interactive session. The patient 4 may provide biometric data in some examples (e.g., facial data, fingerprint data, iris data, voice data, characteristic implantation site data, etc.). In one example, computing device(s) 2 may include a biometric scanner (e.g., camera 32, fingerprint scanner, etc.) that patient 4 or another user may use to provide authentication/biometric data. In some cases, camera 32 may image the implantation site to identify patient 4, where processing circuitry 20 includes AI engine(s) 28 and/or ML model(s) 30 trained to identify patient 4, to a certain degree of certainty, based on one or more initial images of the implantation site. Processing circuitry 20 may identify patient 4 from unique characteristics of the implantation site of patient 4. In another example, processing circuitry 20 may authenticate user based on wireless communication with IMD 6 of patient 4 (e.g., NFC data, telemetry protocol data, RFID data, etc.).

In some examples, patient 4 may or may not be the main user of computing device(s) 2 for purposes of engaging and/or navigating the interactive session. In an illustrative example, a user, separate from patient 4, may be the user of computing device(s) 2 for purposes of engaging and/or navigating the interactive session. That is, the user may coordinate with patient 4 while navigating the interactive session on behalf of patient 4. In an illustrative, a user, separate from patient 4, may login to access the interactive session. In such instances, the user, upon being authenticated to access the interactive session, may then identify patient 4. In some examples, the user may identify the patient by taking a photo of the patient, entering the patients name, scanning a barcode of the patient, imaging the wound site, etc. In an illustrative example, the user may take a photo of the face of patient 4 or of the implantation site. In any case, computing device(s) 2 may perform facial detection or wound characteristic detection in order to determine patient 4.

Processing circuitry, e.g., processing circuitry 20 of computing device(s) 2, processing circuitry 64 of edge device(s) 12, processing circuitry 98 of server(s) 94, or processing circuitry 40 of medical device(s) 17, may deploy image processing tools (e.g., AI engine(s) 28 and/or ML model(s) 30) in order to perform the authentication process. In an example, processing circuitry 20 may train the image processing tools on patient data, implantation site data, etc. In one example, the imaging processing tools may learn, when scanning an implantation site, for example, how the implantation site is healing over time (e.g., a healing trend). Generally speaking, characteristics of an implantation site may change over time and thus, processing circuitry 20 may, over time, adjust relevant portions of the identification algorithm accordingly. This is especially useful in instances where the identification algorithm of processing circuitry 20 utilizes, for example, image(s) of the implantation site to identify and/or authenticate a user. In such instances, processing circuitry 20 may still be able to accurately identify patient 4, even if an amount of time has passed between check-in sessions.

In some instances, while attempting to identify patient 4 via camera 32, processing circuitry 20 may detect a potential abnormality at this stage. Computing device(s) 2, in such instances, may request additional identification data in order to correctly and/or accurately identify the patient 4. In some instances, processing circuitry 20 may store authentication data (e.g., two-step authentication data) to storage device 24 so as to streamline the authentication and identification process for patient 4 in subsequent sessions. In another example, processing circuitry 20 may query a database (e.g., storage device 96 of remote server(s) 94), via network 10, that maintains patient data (e.g., usernames, passwords, implantation site characteristic data, implantation site images, etc.). In such instances, processing circuitry 20 may identify, from the patient data, patient 4 upon receiving search results from the database. In an illustrative example, processing circuitry 20 may receive user input, via UI 22, indicating a patient name of patient 4. Processing circuitry 20 may query the database and based on a result of the query, identify patient 4 as a known patient of system 100 (e.g., system 300).

Processing circuitry 20 may reference patient data (e.g., patient identifiers) such that the same computing device(s) 2 (or the same algorithm base) can be shared across multiple patients (e.g., in a clinic). As described herein, computing device(s) 2 may adjust, based on patient data, the base of the site-check algorithm in order to tailor the process and UI visualizations in order to accommodate each respective patient. In another example, a common site-check algorithm may be deployed to accommodate all patients of a certain class (e.g., nursing home patients, patients of a particular nursing home, etc.). In this way, the site-check algorithms may maintain and provide a particular level of uniformity for the various users of the interactive session, where those users may be part of a common class.

In some examples, a plurality of computing device(s) 2, while concurrently operating the interactive session, may both capture images of the implantation site of a single patient 4 and determine other data items (e.g., interrogation data), as well. That is, a computing device 2 of patient 4 may, while operating the imaging program, perform the techniques of this operation, as well as a computing device 2 of a caregiver. In such examples, computing device(s) 2 may synchronize data and/or analysis results in real-time or in some instances, at a later point in time, such as by waiting until a wireless connection between computing device(s) 2 is available or a network connection becomes available (e.g., a connection via network 10). In some instances, until computing device(s) 2 determines to perform a data synchronization process, computing device(s) 2 may store data locally, such as to storage device 24, or in some instances to storage device 62 of an edge device 12.

In some examples, following the receipt of authentication data identifying a user of the imaging program, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the identification data for patient 4. In such examples, the user of the interactive session may include a HCP, a family member of patient 4, patient 4, etc. To illustrate, processing circuitry 20 may authenticate and authorize the user to access the interactive session. Subsequently, processing circuitry 20 may receive, via UI 22, input data, such as user input, that effectively identifies patient 4. In one example, the input data includes barcode scanning data, selection of patient 4 from a dropdown menu (e.g., via a keyword search), manually entered patient information, etc. In any event, computing device(s) 2 may then determine, from the input, identification data for patient 4, such as by determining the name or ID of patient 4.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine IMD information that corresponds to one of medical device(s) 17 (e.g., IMD 6) of patient 4. In an example, processing circuitry 20 may identify, based at least in part on the identification data, IMD information that corresponds to a particular one of medical device(s) 17. In some examples, the IMD information may include IMD implantation site information, such as where the implantation site is located on the body of patient 4, a size and shape of the implantation site, and other information regarding the implantation site. In another example, IMD information may include historical data relating to the implantation site of the IMD and/or historical data relating to the IMD. In some examples, the historical data may include images of the implantation site following the implantation procedure, wound characteristics, shape and size of the implantation site (e.g., the wound size), incision information, history of any complications during surgery, date of the implant, etc. In some examples, IMD information may further include IMD type information, IMD communication protocol information, an estimated orientation of medical device(s) 17 (e.g., IMD 6), data regarding one or more HCPs (e.g., surgeons, clinicians) responsible for implanting (e.g., inserting) medical device(s) 17 (e.g., IMD 6), information relating to one or more methods employed by the one or more HCPs when sealing the implantation site, images of the implantation site over time, etc. Example implantation methods and instruments are described, for example, in U.S. Patent Publication No. 2014/0276928, incorporated herein by reference in its entirety. In any case, computing device(s) 2 may determine the presence of a potential abnormality at the implantation site (e.g., a likelihood that the potential abnormality is an actual abnormality) based on the implantation methods and instruments used during the implantation surgery. In one example, computing device(s) 2 may compare image data of the implantation site against reference image data from a library of reference images, where the library may have tagged the reference images with various details such as implantation methods and instruments (e.g., library metadata). Computing device(s) 2 may determine an abnormality at the implantation site by, at least in part, referencing corresponding images from the reference library that include similar implantation method and instrument attributes to that of the implantation site computing device(s) 2 is imaging.

In a non-limiting and illustrative example, computing device 502 may launch the interactive session (e.g., a virtual check-in) when prompted by patient 4, when scheduled on a specific date post implant, and/or when pushed a request during or around a clinic check. In some examples, computing device 502 may cause an interactive session program for a user (e.g., patient 4) to expire after a given time. In another example, the interactive session may not include an explicit expiration date (e.g., a so-called "evergreen" application).

In an illustrative example, computing device 502, when providing an interactive session, may identify a follow-up schedule for the patient. In an example, computing device 502 may receive the follow-up schedule, for example, from one of computing device(s) 2 of an HCP or may access the follow-schedule from a database via network 10. The follow-up schedule may define one or more time periods in which computing device 502 is configured to prompt the user to conduct the interactive session. In some examples, the one or more time periods may include at least one time period that corresponds to a predetermined amount of time from a date of implantation of IMD 6. That is, a first time period or at least one time period of the one or more time periods may be a predetermined time from the date of implantation of the IMD (e.g., a number of days since implantation of IMD 6).

In an illustrative example, the follow-up schedule may include a first time period for computing device 502 to provide a prompt, e.g., 15 days after implantation, or after removal, of medical device 17 (e.g., IMD 6). In another example, computing device 502 may include a variable time period that an AI engine(s) 28 and/or ML model(s) 30 may determine for patient 4, such that different check-in schedules may exist for different patients based on various different criteria. In such examples, computing device 502 may provide the interactive session in accordance with the follow-up schedule. In another example, computing device 502 may provide a prompt, for example, to a mobile device user, to capture the image data using computing device 502 a predetermined time after an implantation resulting in the implant-related wound. In some examples, computing device 502 identifies the follow-up schedule by receiving, via communication circuitry 26, a push notification from another device, and determining, based on the push notification, a first time period for the follow-up schedule. In such examples, the push notification may include a HCP push that is received from one of computing device(s) 2 of an HCP, such as an HCP that corresponds to patient 4. In some examples, computing device 502 may identify the follow-up schedule by receiving a physiological parameter that indicates an abnormality (e.g., an ECG abnormality) and determining a first time period for the follow-up schedule based on the physiological parameter abnormality. That is, computing device(s) 2 may determine a triggering event for identifying a follow-up schedule that includes a trigger based on an amount of time that has passed, a particular signal received from one of medical device(s) 17 (e.g., IMD 6), such as an activity level, an ECG, etc., or based on a trigger received via network 10 (e.g., a computing device 2 of an HCP).

Figure 7:
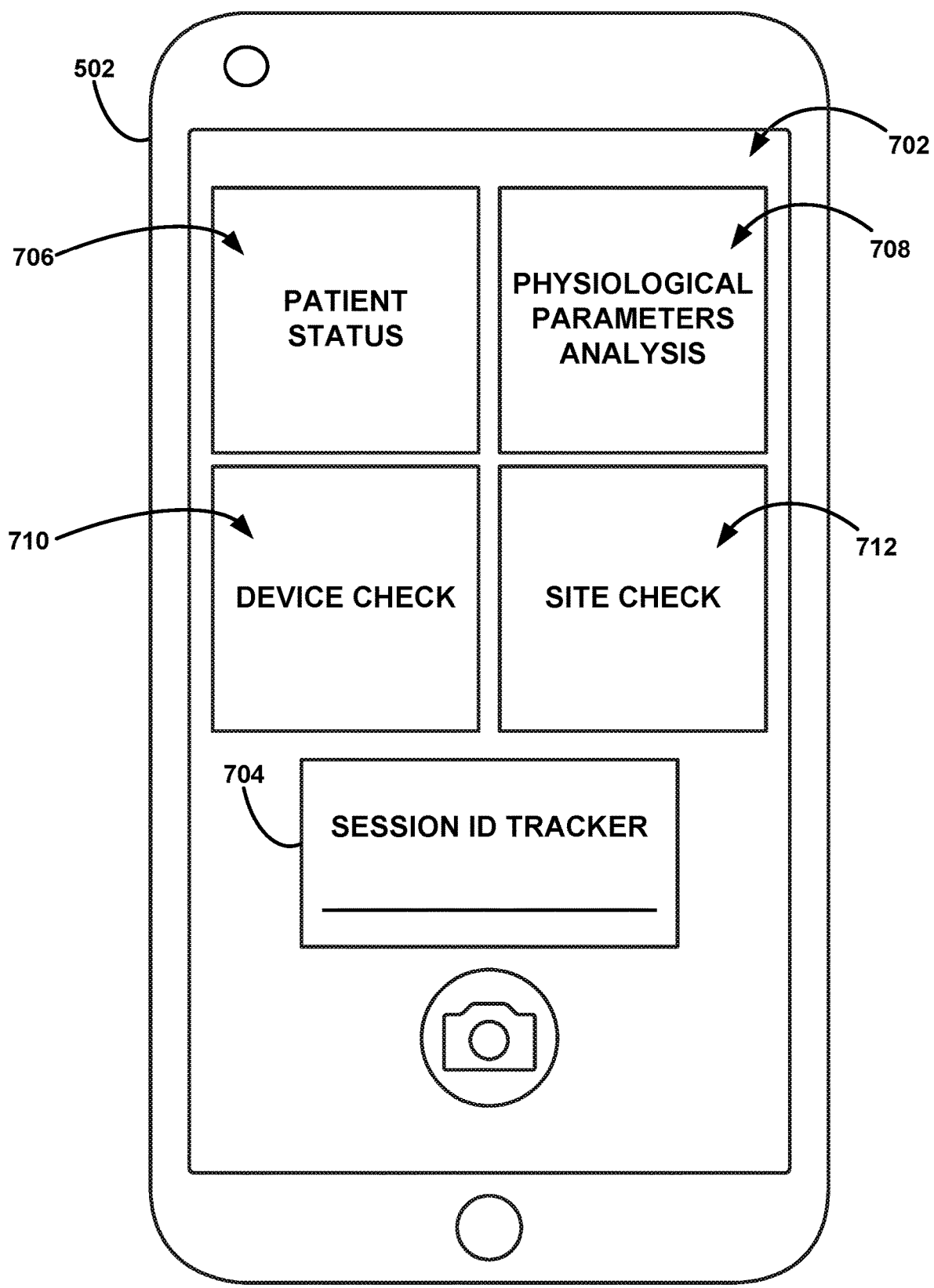
FIG. 7 is an UI visualization of an example menu interface, in accordance with one or more techniques of this disclosure.

FIG. 7 is an UI visualization of a menu interface 702, in accordance with one or more techniques of this disclosure.

Upon initiation of the interactive session, computing device 502 may output, via UI 22, an interactive UI, according to the virtual check-in interactive session. In some examples, computing device 502 may provide a top-level interface that includes at least one first interface tile. The first interface tile may correspond to the first subsession. In such instances, the first subsession may include a first subinterface level that is at a lower level relative to a level of the top-level interface. The top-level UI interface may present several tiles from which the user can choose. In the example, of FIG. 7, the app of this disclosure outputs a UI program that includes one or more graphical UI visualization elements (collectively, UI elements or "tiles").

While described as being provided as part of a hierarchal structure with tiered-levels, it will be understood that the techniques of this disclosure are not so limited, and that the subsession interfaces may be separate from a first interactive session interface in terms of what a user may see as a default when initialing receiving the session interfaces. In an example involving a mixed reality context, computing device 502 may present all interfaces at a single level, where a user may access each individual subsession interface, for example, by panning the head of patient 4 around a virtual reality user interface. In an illustrative and non-limiting example, a user may access and/or initiate a subsession from the virtual reality user interface, where the virtual reality interface may, in some instances, convert to an augmented reality interface, such as when computing device 502 detects selection of the first subsession (e.g., a site-check subsession). In such instances, computing device 502 may transition to an augmented reality mode in which the user may, for example, image an implantation site of patient 4 via camera 32 (e.g., a head-worn camera or another camera communicatively coupled to computing device 502), in accordance with one or more of the various techniques of this disclosure. Once the first subsession is complete, computing device 502 may revert to a separate user interface (e.g., the top-level, menu interface or a second subsession interface) that is again, in some instances, presented in a virtual reality context. While several examples may be described herein for user interaction with the interactive subsession of this disclosure, it will be understood that the interactive subsession and subsession may be provided in various contexts not necessarily described herein for sake of brevity.

As shown in the illustrative example of FIG. 7, the UI elements of interface 702 may include a patient status tile 706, a physiological parameters analysis tile 708, a device check tile 710, and/or a site check tile 712. The user (e.g., patient 4, caregiver, physician) can select any of these tiles (e.g., via a touch input) to leverage the functionalities associated with the description of each such tile. In some examples, the UI elements may comprise interactive graphical units that may be presented to a user via UI 22. In some examples, selection of the camera icon may cause computing device 502 to automatically launch a site-check subsession so as to provide a shortcut to site-check page accessible via site-check tile 712.

In addition, any one of the interfaces described herein may include a session ID tracker tile 704. Session ID tracker tile 704 may provide session and/or subsession tracking information, such as date stamps, timestamps, session ID stamps and/or subsession ID stamps, user information, etc. The session ID tracker may further include historical data regarding a previous session (e.g., historical data regarding one or more previous subsessions), such as a summary of the results of a previous report (e.g., a session report, reports detailing abnormality results for one or more subsessions, etc.). In any case, computing device 502 may include such session tracking information when generating a new report for each particular interactive session, each particular subsession (e.g., sub-reports for subsessions), etc. A top-level interface 702 may include multiple session ID tracker tiles 704, such as one for each subsession tile.

In addition, individual interfaces for one or more subsessions may include tracker tiles, that when computing device 502 detects selection of a particular tracker tile, computing device 502 may retrieve historical information about each subsession and previous subsession results (e.g., reports, etc.). Computing device 502 may provide a pop-up interface that provides such information via UI 22 or in some instances, may automatically navigate a user, via UI 22, to a report and/or history interface for further review. In addition, computing device 502 may export such data (e.g., reports, history, etc.) out of the interactive session interface to another interface and/or to another device altogether (e.g., one of computing device(s) 2 of a HCP, one of server(s) 94, edge device(s) 12, etc.). In one example, computing device 502 may export reports in response to detected selection of an export report button (e.g., a soft key), in response to detecting a user selection of one of subsession tracker tiles or interactive session tracker tile 704. The exported reports may include multiple reports (e.g., subsession reports) or compilation reports (e.g., interactive session report) detailing an analysis of a plurality of data items from a plurality of subsessions. In an illustrative example, computing device 502 may detect selection of a subsession tracker tile, via a subsession interface, and in response, may generate and/or export a report corresponding to the particular subsession of a particular interface of the interactive session.

In another example, computing device 502 may detect selection of an interactive-session tracker tile (e.g., tracker tile 704) and in response, may generate and/or export a report corresponding to the interactive session, a report corresponding to the particular subsessions that have been executed thus far, if not all subsessions, and/or a comprehensive report corresponding to an entire interactive session, as well as any summary reports for individual subsessions. In another example, computing device 502 may generate historical reports that include an aggregation of any one or more of the reports, such that in response to detecting a selection of an interactive-session tracker tile or other tracker tile, computing device 502 may retrieve historical reports and compile and/or summarize reports from the past in order to produce a single post-implant historical report for export and/or display (e.g., via a pop-up interface). In such instances, computing device(s) 2 of an HCP may receive the post-implant report, via network 10, such that the HCP may review the historical record and/or a summary of the historical record for patient 4 (e.g., for medical device(s) 17 corresponding to patient 4).

Figure 8:
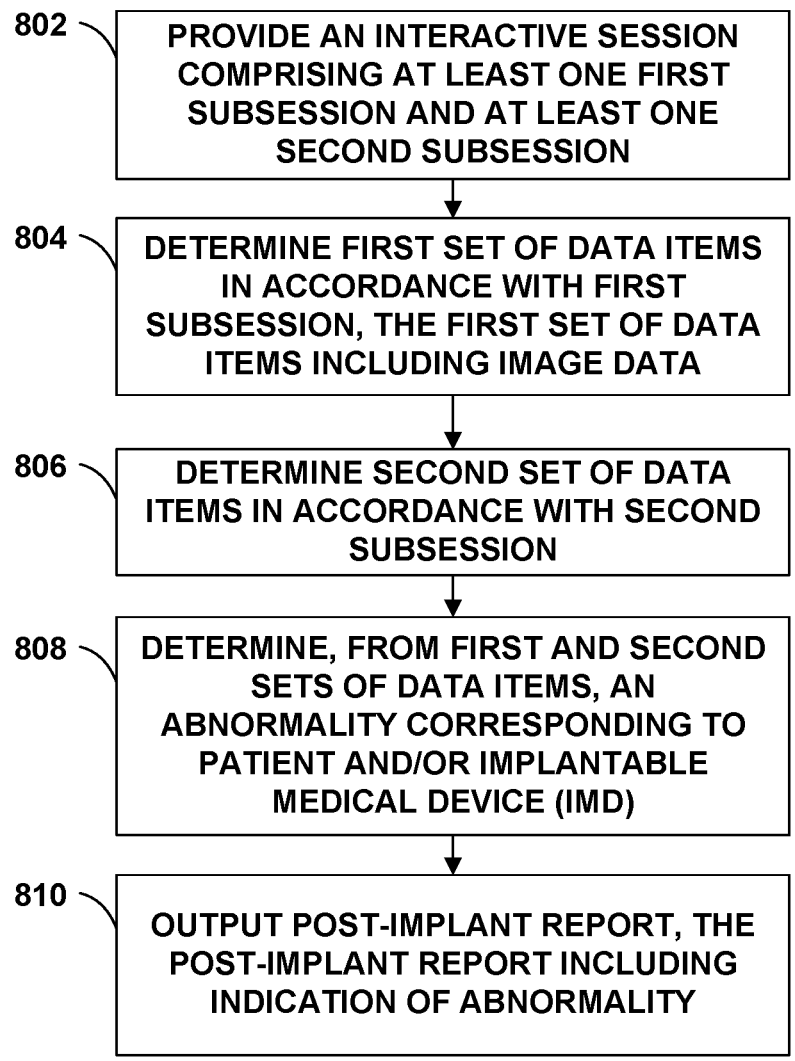
FIG. 8 is a flowchart illustrating an example method of utilizing UI input and data processing, in accordance with one or more techniques of this disclosure.

FIG. 8 is a flowchart illustrating an example method of implementing subsession techniques of a virtual check-in interactive session, in accordance with one or more techniques of this disclosure. The subsession techniques of this disclosure may be used to obtain various data items and comprehensively determine abnormalities at an bodily site of a patient 4 based on a combination of data items.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may obtain image data associated with the body of patient 4, and determine a present status of an implant-related wound on the body of patient 4. In such examples, the image data includes one or more frames that represent images of a body of patient 4. In addition, a portion of the body of patient 4 includes, in some examples, an implantation site of IMD 6, such that the frames represent images of the implantation site. In an illustrative example, processing circuitry 20 may prompt a mobile device user (e.g., patient 4) to capture the image data using the mobile device. In such examples, processing circuitry 20 may prompt the mobile device user a predetermined time after an implantation resulting in the implant-related wound. As described herein, processing circuitry 20 may further obtain data associated with functioning of one of medical device(s) 17 implanted within the body of patient 4. Processing circuitry 20 may further determine performance metrics of medical device(s) 17 based on the obtained data (e.g., interrogation data, diagnostic data). In some examples, processing circuitry 20 may determine performance metrics of the medical device based on the captured image data, such as an image indicative of device migration that may, in turn, affect various performance metrics of, e.g., IMD 6.

In an illustrative example, processing circuitry, e.g., processing circuitry 20 of computing device(s) 2, processing circuitry 64 of edge device(s) 12, processing circuitry 98 of server(s) 94, or processing circuitry 40 of medical device(s) 17, may monitoring patient 4. In an example, processing circuitry 20 may provide an interactive session configured to allow a user to navigate a plurality of subsessions comprising at least a first subsession and a second subsession that is distinct from the first subsession, where the first subsession comprises capturing image data via one or more cameras 32 (802). In some instances, processing circuitry 20 may provide the interactive session in response to being pushed to patient 4 through cloud solutions. In an example, the interactive session may include a mobile app that is pushed to patient through cloud solutions. In another example, processing circuitry 20 may provide the interactive session based on a scanning of a QR code from flyer given at implant time or shortly before/after.

In some instances, processing circuitry, e.g., processing circuitry 20 of computing device(s) 2, processing circuitry 64 of edge device(s) 12, processing circuitry 98 of server(s) 94, or processing circuitry 40 of medical device(s) 17, may provide the interactive session (e.g., a first subsession, a site-check subsession, etc.) by training (e.g., via processing circuitry 20) a session generator on one or more of: cohort parameters or IMD information; deploying, via the computing device, the session generator to generate the interactive session; and providing, via the session generator, the interactive session that, as a result of the training, is at least in part personalized for the user. In addition, the session generator may reference historical interrogation data for comparison when personalizing the interactive session. The session generator may include AI engine(s) 28 and/or ML model(s) 30.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine a first set of data items in accordance with the first subsession of the interactive session (804). In an example, processing circuitry 20 may determine a first set of data items including image data as part of a site-check subsession.

In some examples, processing circuitry 20 may determine a second set of data items in accordance with the second subsession of the interactive session, the second set of data items distinct from the first set of data items and comprising one or more of: data obtained from medical device(s) 17 (e.g., IMD 6), at least one physiological parameter of patient 4, or user-input data (806). In some examples, processing circuitry 20 of computing device(s) 2 or of computing device 502 may perform a pairing session (e.g., a pairing process) with one or more medical device(s) 17 (e.g., IMD 6), with another computing device(s) 2, and/or with edge device(s) 12 (e.g., an IoT device in the home). The pairing session is configured to pair the computing device with the respective device (e.g., IMD 6). In some examples, the pairing session may include an authentication process as described herein. In an illustrative example, a mobile computing device may be initialized to communicate with IMD 6, including authentication (e.g., 2-step authentication) so that only authorized mobile computing devices can interface with IMD 6. In such examples, in a first instance, IMD 6 may transmit a signal to computing device 2 in response to computing device attempting to pair with IMD 6.

The user may then authenticate themselves, and if proper, IMD 6 may then pair with computing device 2 and initiate a bidirectional or unidirectional communication between devices. IMD 6 may then remember a unique ID of the computing device 2 for future authentication (e.g., via a hash key, neural network, etc.). In any case, computing device 2 may receive during the pairing session information about the IMD. In such instances, computing device 2 may receive, via the pairing process, the interrogation data regarding IMD 6 (e.g., from IMD 6). In some examples, computing device 2 may store the interrogation data as historical interrogation data for subsequent reference and/or to use as training sets for AI engine(s) 28 and/or ML model(s) 30. That is, IMD information, in some instances, may include device interrogation data (e.g., historical interrogation data).

In accordance with one or more of the various techniques of this disclosure, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, based at least in part on the first set of data items and the second set of data items, an abnormality corresponding to at least one of patient 4 and/or IMD 6 (808). In an example, processing circuitry 20 may output a post-implant report of the interactive session, wherein the post-implant report includes indication of the abnormality (810). Processing circuitry, e.g., processing circuitry 20 of computing device(s) 2, processing circuitry 64 of edge device(s) 12, processing circuitry 98 of server(s) 94, or processing circuitry 40 of medical device(s) 17, may provide patient 4 with the capability to generate a report (e.g., in PDF format or in various other formats) for their records, to email or FTP to family members or to a doctor, etc. In some examples, the post-implant report may further include indication of an amount of time that has transpired since the date of implantation of IMD 6. In some examples, processing circuitry 20 may determine the post-implant report by determining, from the second set of data items, the abnormality (e.g., an ECG abnormality) and determining, based at least in part on the abnormality and the images, the post-implant report. In any case, processing circuitry 20 may determine a manner in which to provide feedback to patient 4, such as through graphical simplified icons or complex results (e.g., depending on HCP preference). At the completion of the interactive session, processing circuitry, e.g., processing circuitry 20 of computing device(s) 2, processing circuitry 64 of edge device(s) 12, processing circuitry 98 of server(s) 94, or processing circuitry 40 of medical device(s) 17, may, in some instances, mark the results on UI 22 provided via the mobile device app, with date and time stamping.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may output the post-implant report by outputting the post-implant report to a device of a HCP via network 10 (e.g., via a bidirectional communication protocol). In one example, processing circuitry 20 may output, via network 10, the post-implant report to another device of the user of UI 22 and/or the interactive session, where the user may or may not necessarily be patient 4.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine that the interactive session is complete and provide a notification that the interactive session is complete, such as by providing a confirmation receipt or by marking tiles of a UI 22 interface as having a threshold number of subsessions complete. In some examples, processing circuitry 20 may output a result of the post-implant report for display (via a display of computing device(s) 2 or of another device (e.g., one of medical device(s) 17 that includes a display). In an illustrative example, when processing circuitry 20 determines that any one or any combination of subsessions yielded an abnormal result (or abnormal outside an acceptable margin of normal), processing circuitry 20 may use the mobile device app to output a prompt to patient 4. In some examples, the prompt may indicate an abnormality. In other examples, the prompt may include a recommendation or instruction to schedule a follow-up visit with the HCP.

In some examples, the first set of data items may include an image overlay (e.g., an augmented reality overlay). The image overlay may be used to augment a set of preview frames for particular angle and size reference. In such examples, processing circuitry 20 may output the image overlay at the first subinterface level. In addition, when providing the first subsession, processing circuitry 20 may detect selection of a first interface tile, and provide the first subsession of the interactive session. In another example, processing circuitry 20, when determining the first set of data items, may provide a prompt for the user (e.g., patient 4, an HCP, etc.) to utilize the one or more cameras 32 to capture the image data, and determine, subsequent to the prompt, at least a portion of the first set of data items (e.g., the image data or at least a portion of the image data). In any case, processing circuitry 20 may prompt a mobile device user to capture the image data using the mobile device a predetermined time after an implantation resulting in the implant-related wound.

In some examples, processing circuitry 20 may provide, via a second subsession interface, a second subsession of the interactive session, and in turn, may modify the second interface tile to indicate completion of the second subsession (e.g., with a checkmark). In addition, processing circuitry 20 may provide, subsequent to the second subsession, the first subsession of the interactive session in order to obtain image data and may, in turn, modify the first interface tile to indicate completion of the first subsession. In some examples, for a convenience of user navigation, processing circuitry 20 may facilitate navigation from the second subsession interface directly to the first subsession interface without necessarily involving a top-level interface. In any case, processing circuitry 20 may also provide, subsequent to the first subsession or the second subsession, a third subsession of the interactive session, and determine a third set of data items in accordance with the third subsession of the interactive session, where the third set of data items is distinct from the first set of data items. In such examples, determining the third set of data items may include processing circuitry 20 receiving physiological parameter signals and determining, from the physiological parameter signals, the third set of data items. It should be noted that the subsession described in this disclosure may be provided in any order, accessed in any order, and in some instances, processing circuitry 20 may phase out one or more subsessions at particular periods of time, such as a predetermined time from implantation, a predetermined time from a user completing a particular interactive session, a result of a particular interactive session (e.g., such as an implantation site status), etc. In one example, processing circuitry 20 may disable access to an imaging subsession after a predetermined time from implantation or after a predetermined time from a healthy status update (e.g., a wound being continuously projected to heal according to an expected schedule). In such examples, processing circuitry 20 may generate the interactive session to include one of a remaining set of subsession to include with the interactive session at a prospective time. In some examples, processing circuitry 20 may generate the interactive session to include a disabled or phased out subsession (e.g., the site-check subsession) such that the disabled subsession is hidden or otherwise inaccessible to the user. Processing circuitry 20 may provide the interactive session to include the subsessions, even if some are rendered inaccessible to the user.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may identify an abnormality from the various data items. In one examples, processing circuitry 20 may determine the abnormality to include a first abnormality. In such examples, processing circuitry 20 may determine the post-implant report by outputting, via communication circuitry 26, the second set of data items to another one of computing device(s) 2. In turn, processing circuitry 20 may receive, via communication circuitry 26, a result of an analysis of any one or more of the sets of data items (e.g., the second set of data items). The result may indicate that the second set of data items does not indicate the presence of a second abnormality. In such examples, processing circuitry 20 may determine the post-implant report based at least in part on the first abnormality and the second set of data items.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may provide the interactive session, including a third subsession and a fourth subsession. In an example, processing circuitry 20 may provide a third subsession that includes a physiological-parameter subsession and may provide a fourth subsession that includes a device-check subsession. In such instances, processing circuitry 20 may determine the abnormality by determining, in accordance with the third subsession, a third set of data items, where the third set of data items includes at least one physiological parameter of the patient and determining, in accordance with the fourth subsession, a fourth set of data items, where the fourth set of data items includes interrogation data. As such, processing circuitry 20 may further determine the abnormality based at least in part on the third set of data items and/or the fourth set of data items.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may initiate the second subsession subsequent to the first subsession. In an example processing circuitry 20 may determine a first set of data items by receiving, via communication circuitry 26, the first set of data items, and may determine the second set of data items by receiving, via the computing device(s) 2, the second set of data items. In some examples, processing circuitry 20 may determine a second set of data items that comprises information indicative of an abnormality of the at least one physiological parameter of the patient or an abnormality of a device parameter corresponding to one or more medical device(s) 17. In such examples, processing circuitry 20 may when determining an indication of the abnormality, output, to an abnormality determiner for an abnormality analysis, at least one of the first set of data items or the second set of data items, and determine a result of the abnormality analysis, where the result indicates the abnormality. In such instances, the abnormality determiner may include at least one of AI engine(s) 28 and/or ML model(s) 30. In one example, one of computing device(s) 2 may include and deploy the abnormality determiner to determine an abnormality at a bodily site of patient 4. That is, processing circuitry 20 may deploy the abnormality determiner to determine the abnormality, where the abnormality determiner may be trained, as described herein, to identify various abnormalities based on image data and on other data items.

In some examples, processing circuitry 20 may determine, as the potential abnormality, the presence of a potential infection at the implantation site. That is, processing circuitry 20 may, in identifying the abnormality at the implantation site, determine the presence of a potential infection at the implantation site. In some examples processing circuitry 20 may detect the potential abnormality at the implantation site based on an analysis of the at least one frame. In another example, processing circuitry 20 may determine the potential abnormality by transmitting, via communication circuitry 26, an image and other data items to edge device(s) 12. That is, computing device(s) 2 may transmit one or more frames of image data to edge device(s) 12, where the frame(s) include one or more images of the implantation site. In addition, computing device(s) 2 may transmit the image and/or other data items, via network 10, to edge device(s) 12, medical device(s) 17 (e.g., a wearable device, a bedside workstation), and/or server(s) 94.

In some examples, computing device(s) 2 may transmit the image and/or other data items to another device, such as server(s) 94, via network 10, in which case, server(s) 94 may transmit the image and/or other data items to edge device(s) 12 for further analysis. That is, in some examples, computing device(s) 2 may transmit data, such as image or video data, indirectly to edge device(s) 12 and/or server(s) 94, via network 10. In one example, computing device(s) 2 may transmit data to edge device(s) 12, which, in turn, performs processing of the data and/or transmission of the data (e.g., edge-processed data) to server(s) 94 for further analysis. In such instances, edge device(s) 12 and/or server(s) 94 may determine the presence of a potential abnormality based on data (e.g., image data, video data, etc.) received from computing device(s) 2 via communication circuitry 26. In any case, computing device(s) 2 may determine the presence of a potential abnormality at the implantation site upon receiving the potential abnormality information from another device (e.g., edge device(s) 12, server(s) 94, etc.).

In an illustrative example, edge device(s) 12 and/or server(s) 94 may receive the image and/or other data items (e.g., second set of data items, third set of data items, fourth set of data items, etc.) from computing device(s) 2. In some instances, edge device(s) 12 and/or server(s) 94 may perform an image processing analysis prior to transmitting a result of the image processing analysis to computing device(s) 2 and/or edge device(s) 12. In some examples, edge device(s) 12 may identify the presence of the potential abnormality based on an analysis of the image data and/or the other data items of the other subsessions. In some examples, edge device(s) 12 may deploy image processing engine(s) (e.g., via AI engine(s) 28 and/or ML model(s) 30) to determine the presence of the potential abnormality. In another example, edge device(s) 12 may perform some or all of the analysis with assistance from server(s) 94. That is, in some examples, server(s) 94 or edge device(s) 12 may include image processing engines or various analysis tools, configured to assist in the detection of a potential abnormality. Server(s) 94 and/or edge device(s) 12 may include image processing engines, such as AI engine(s) 28 or ML model(s) 30, described with reference to FIG. 2. In one example, server(s) 94 or edge device(s) 12 may include training sets for training one or more imaging processing engine(s). Server(s) 94 and/or edge device(s) 12 may perform the training of the image processing engine(s) or in some instances, may assist computing device(s) 2 with training the image processing engine(s). In another example, server(s) and/or edge device(s) 12 may transmit training sets to computing device(s) 2. In such instances, computing device(s) 2 may train the image processing algorithms (e.g., via AI engine(s) 28 and/or ML models(s) 30). In any case, computing device(s) 2 may determine, from the images, the presence of a potential infection at the implantation site based on an analysis of the images.

In addition, when identifying the abnormality, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the likelihood that the potential abnormality is an actual abnormality (e.g., a severity metric, probability metric, etc.). In one example, processing circuitry 20 may determine the likelihood that the potential abnormality is an actual abnormality based on information that defines the potential abnormality (e.g., class of abnormality, abnormality characteristics, IMD type, etc.). In some instances, processing circuitry 20 may determine the likelihood by receiving, from another device (e.g., edge device(s) 12, server(s) 94, etc.), data indicating a likelihood of the potential abnormality being an actual abnormality or in some instances, data indicating a likelihood that the potential abnormality poses a health risk, whether serious or not. In a non-limiting example, processing circuitry 20 may determine the likelihood that a potential infection determined from a set of images represents an actual infection.

As a person skilled in the art would appreciate, an actual infection (e.g., a real infection) may be evidenced by a confirmed or verified presence of an infectious agent at the implantation site. In other words, a potential infection determination is an unverified determination that an implantation site has become infected with an infectious agent. That is, computing device(s) 2 may determine a potential infection as a possible infection based on data available to computing device(s) 2, but computing device(s) 2 may not diagnose an actual infection without additional input indicating that the infection is, in fact, an actual infection. In any case, computing device(s) 2 may determine, based at least in part on the images and one or more other data items, a likelihood that the potential infection at the implantation site is an actual infection. In addition, an actual abnormality, such as a healing abnormality, may be evidenced by an actual abnormality in the healing process, such as may be confirmed or verified by another source (e.g., an HCP).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may use weighting factors (e.g., a built-in bias, error margins, etc.) when determining the likelihood of the potential abnormality being an actual abnormality. In one example, processing circuitry 20 may train AI engine(s) 28 and/or ML models(s) 30 on a pool of data, including patient data, implantation site data, rate of false positives, error margin information, etc., in order to determine an accurate likelihood of the potential abnormality being an actual abnormality. In one example, a built-in bias may include a bias toward confirming a potential abnormality as being more likely than not an actual abnormality when the IMD is of a particular type or when a particular number of images indicate a potential abnormality.

Figure 9:
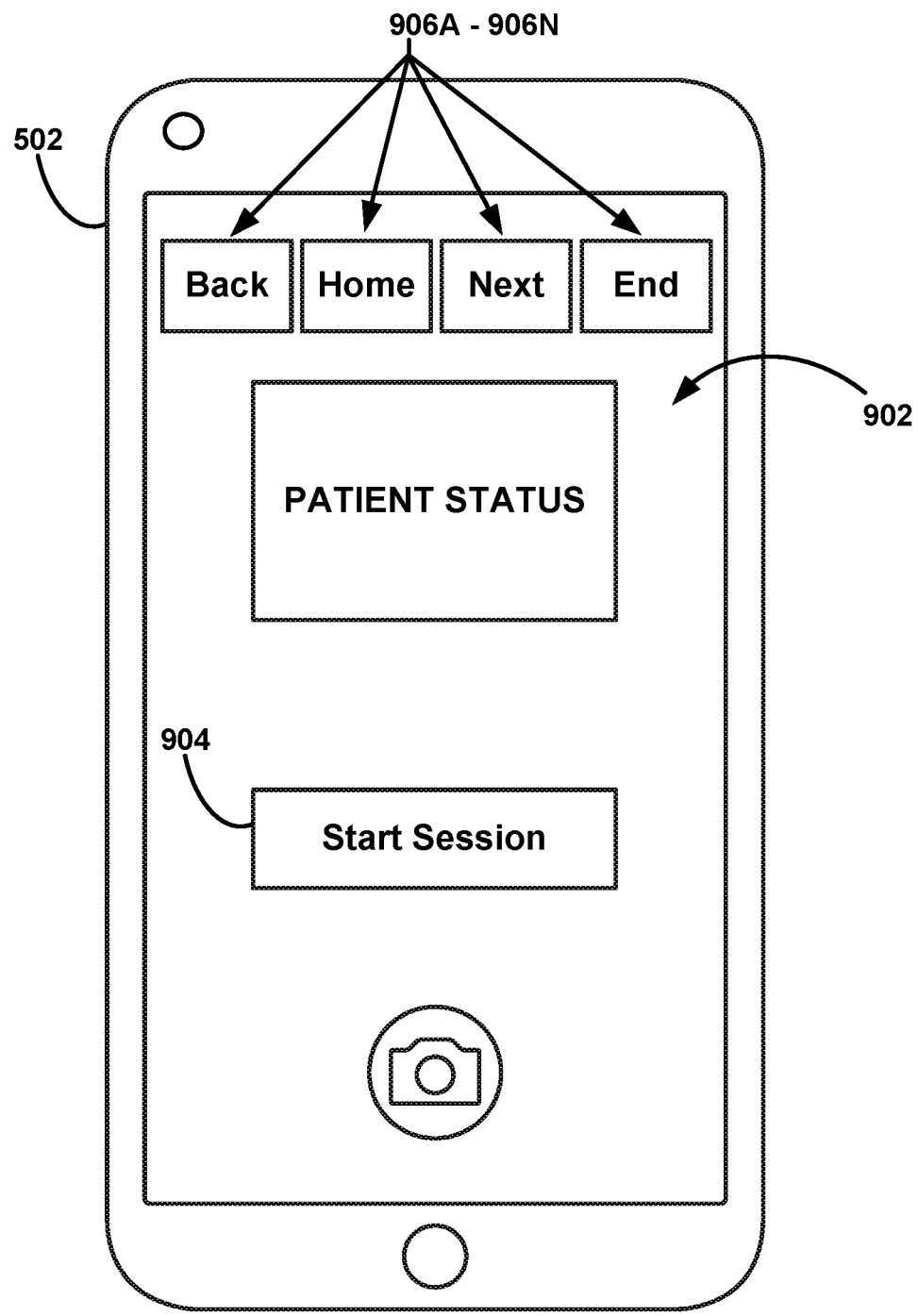
FIG. 9 is an UI visualization of an example patient status interface that presents upon user request of patient status interface illustrated in FIG. 7, in accordance with one or more techniques of this disclosure.

FIG. 9 is an UI visualization of a patient status interface 902 that presents upon user request of patient status interface illustrated in FIG. 7. That is, FIG. 9 illustrates a UI visualization screenshots of invocation and initiation of UIs of the user-facing mobile device app of this disclosure upon the user selection of the patient status tile illustrated in FIG. 1. Various UI visualizations of this disclosure may include navigation buttons 906A-906N. The navigation buttons may include a back button 906A, a home button 906B, a next button 906C, an end button 906N, etc. In some instances, button 600 may function as a home button 906B that returns a user to a home of the computing device 502 or a home page of the application, such as interface 602 or 702. Interface 902 may include a start session tile 904, which when selected, may launch a patient status subsession configured to elicit or solicit patient input. In some examples, patient status interface 902 may serve as a hub for health information for patient 4. In one example, in addition to health information received via computing device 502, computing device 502 may also receive health information from other devices, wearable devices, or other software applications.

Figure 10:
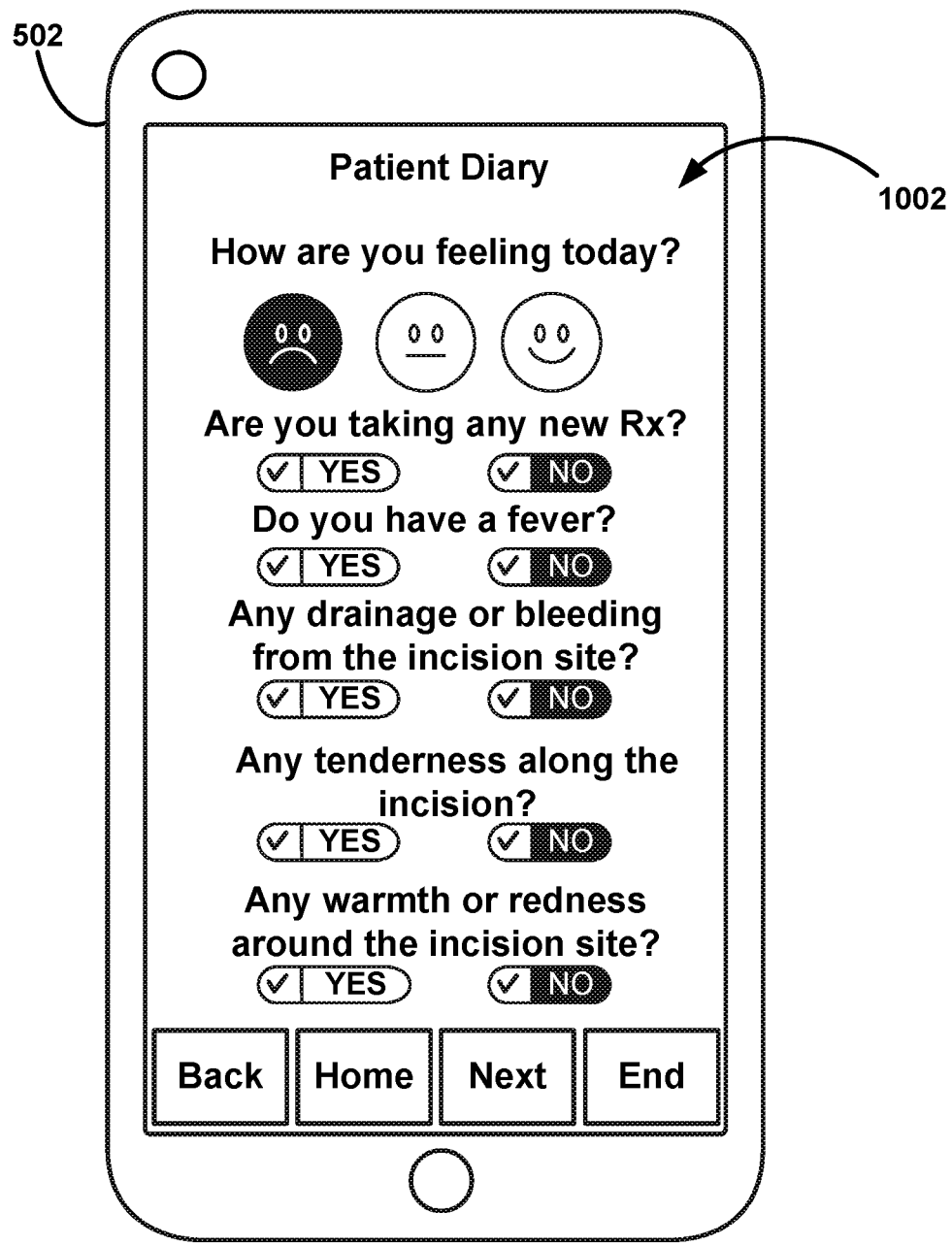
FIG. 10 is a UI visualization of an example patient status interface, in accordance with one or more techniques of this disclosure.

FIG. 10 is a UI visualization of an example patient status interface 1002, in accordance with one or more techniques of this disclosure. FIG. 10 illustrates a non-limiting example of a patient status questionnaire that either the backend system or the mobile device application of this disclosure may generate. The patient status questionnaire may be used to gauge information on a general health picture of patient 4, on implant-recovery-specific symptoms, medications that the patient has taken recently or will take soon, etc. Patient status interface 1002 may be a UI page that allows patient 4 or another user to enter information about patient 4, for example, via free text, dropdown menus, radio buttons, etc. In some examples, computing device(s) 2 may train AI engine(s) 28 and/or ML model(s) 30 on patient health information in order to more accurately determine abnormality information for an implantation site (e.g., severity of abnormality type, etc.). In one example, computing device(s) 2 may receive user input indicating soreness, redness, etc. at the implantation site. In such instances, AI engine(s) 28 and/or ML model(s) 30 may utilize such information when determining a potential abnormality. In some instances, computing device 502 may receive the patient health information as audio data, in which case, computing device 502 may train AI engine(s) 28 and/or ML model(s) 30 on the audio data.

As described herein, in some examples, the second subsession may include the patient-status subsession. In such examples, processing circuitry 20 may, via UI 22, determine a set of data items according to the patient-status subsession. In an example, processing circuitry 20 may receive user-input data in accordance with the second subsession of the interactive session and determine, from the user-input data, a second set of data items.

The user-input data may include one or more of: patient-entered data, medication information, symptom information, physiological metrics, or anatomical metrics. In an illustrative example, the user-input data may include patient pain levels, soreness levels, perceptions of redness at or adjacent the implantation site, etc. Processing circuitry 20 may utilize such information in order to determine, from image data, whether an abnormality is present at or adjacent an implantation site. In one example, processing circuitry 20 may receive an image of a user pointing at particular area of a bodily site of patient 4 and may indicate, via user-input, that the indicated area is sore at a particular soreness level. In some examples, processing circuitry 20 may, in accordance with a site-check subsession, obtain one or more additional images of the bodily site and perform image processing and analysis in view of the user-input and the gesture indication (e.g., pointing) in order to determine with particularity and confidence at a particular confidence interval that a specific area of the bodily site includes a potential abnormality. In some instances, processing circuitry 20 may indicate the potential abnormality at a different area of the bodily site (e.g., above the implantation site), even where the patient indicates another area is sore (e.g., below the implantation site), where processing circuitry 20 identifies from the image data and/or other data items that the potential abnormality is more likely linked to one area (e.g., above the implantation site) over another area (e.g., below the implantation site).

In some examples, processing circuitry 20 may input the user-input data into a risk calculator (e.g., AI engine(s) 28 and/or ML model(s) 30) that is configured to control the frequency at which patient 4 receives subsequent notifications to image a particular bodily site of patient 4. In an example, when a symptom risk score is high, processing circuitry 20 may prompt patient 4 more often to image a bodily site of patient 4.

Figure 11:
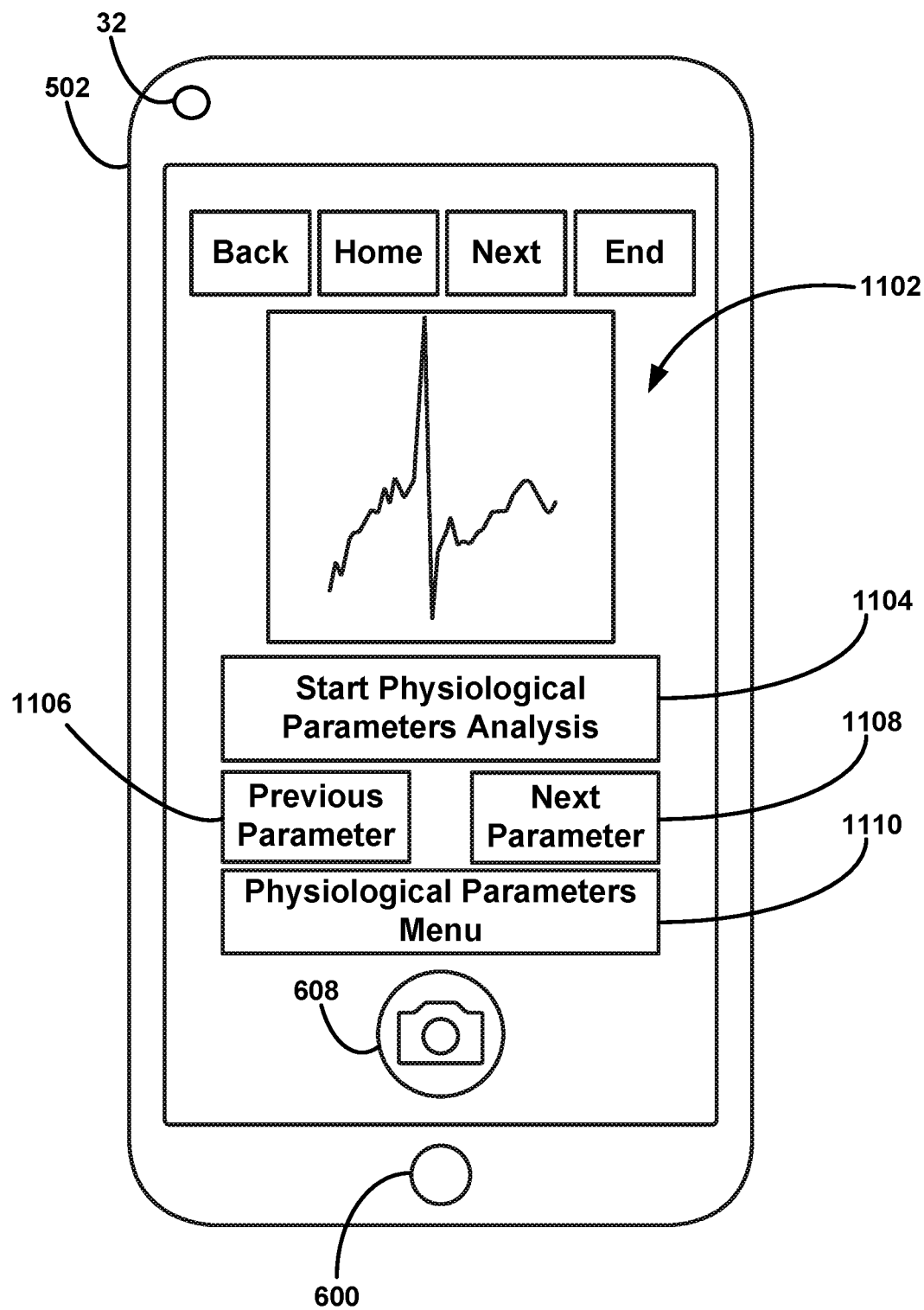
FIG. 11 is a UI visualization of an example physiological parameter check interface, in accordance with one or more techniques of this disclosure.

FIG. 11 is a UI visualization of an example physiological parameter check interface 1102, in accordance with one or more techniques of this disclosure. The physiological parameter check interface 1102 may include buttons including, start physiological parameters analysis 1104, previous parameter 1106, next parameter 1108, and a physiological parameters menu. In some cases, physiological parameter check interface 1102 illustrates the interface that is invoked or initialized upon the user selecting the physiological parameters analysis tile illustrated in FIG. 7 (e.g., tile 708).

Figure 12:
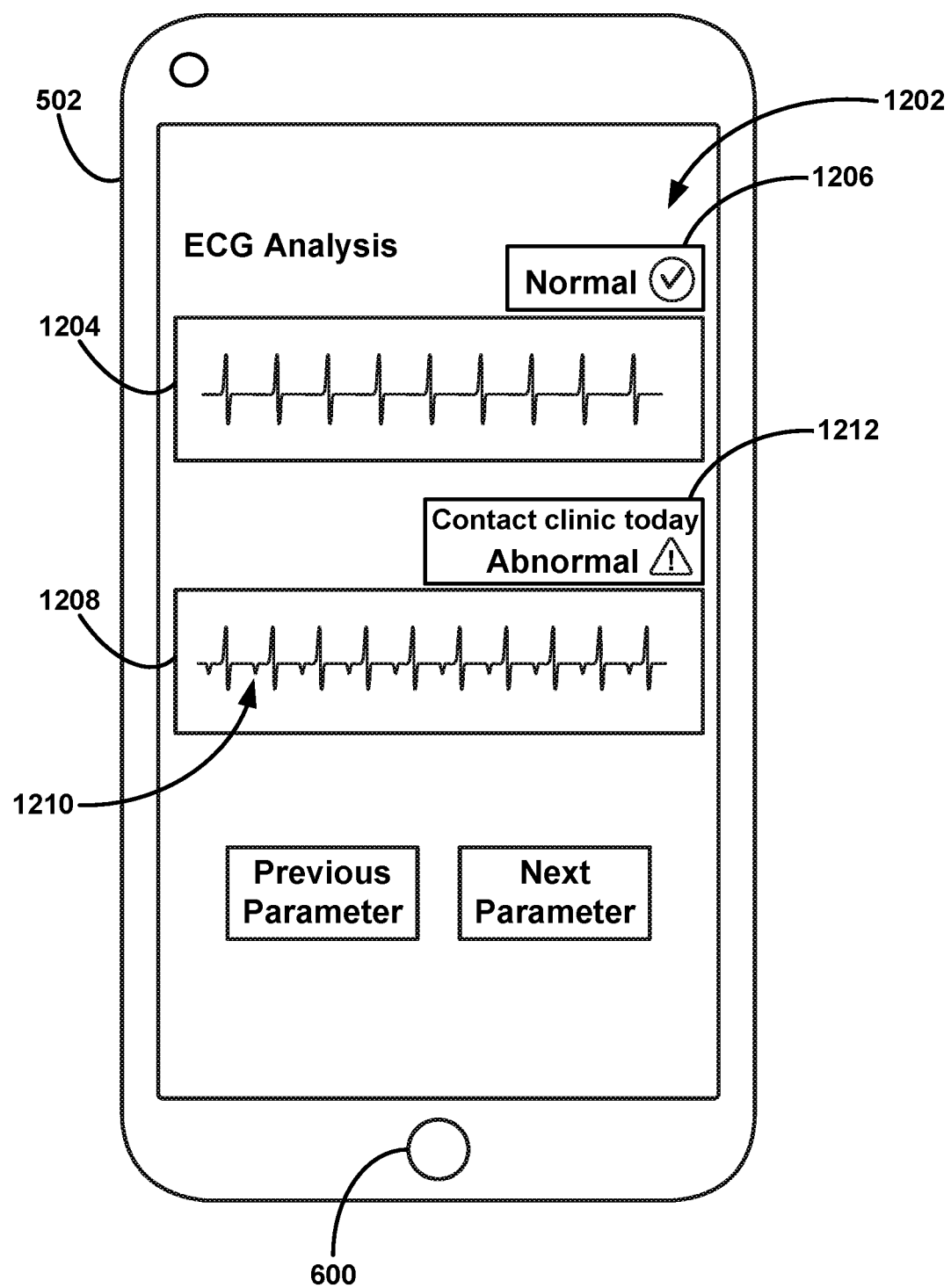
FIG. 12 is a UI visualization of an example physiological parameter check interface, in accordance with one or more techniques of this disclosure.

FIG. 12 is a UI visualization of an example physiological parameter check interface 1202, in accordance with one or more techniques of this disclosure. In an illustrative example, physiological parameter check interface 1202 includes an ECG analysis page. Physiological parameter check interface 1202 illustrates, as a non-limiting example, two outcomes, namely, a normal ECG analysis 1204 and an abnormal ECG analysis 1208 (e.g., as indicated by an abnormality 1210 observed in the ECG). The ECG may be received from one of medical device(s) 6, medical device(s) 17 (e.g., an IMD), or another device such as a watch, fitness tracker, or other wearable device configured to collect ECG data. In any case, computing device(s) 2 may obtain ECG data for analysis. In a non-limiting and illustrative example, the analysis may include a normal result 1206 or abnormal result 1212, in which case an alert to contact a clinic may be warranted.

In some examples, a subsession may include the physiological-parameter subsession. In such examples, processing circuitry 20 may determine a set of data items in accordance with the physiological-parameter subsession. In an example, processing circuitry 20 may receive, in accordance with the second subsession, at least one physiological parameter corresponding to patient 4, and determine, from the at least one physiological parameter, a set of data items. In some examples, processing circuitry 20 may receive, via communication circuitry 26, the at least one physiological parameter from one or more medical device(s) 17, including IMD 6. The at least one physiological parameter comprises at least one of: an electrocardiogram (ECG) parameter, a respiration parameter, an impedance parameter, a core body temperature, a skin surface temperature, an activity parameter, blood pressure, vitals, glucose levels, rhythm data, and/or a pressure parameter. In some examples, the ECG parameter represents an abnormal ECG. In such instances, processing circuitry 20 may determine an abnormality at a bodily site of patient 4 based at least in part on the abnormal ECG, and in some instances, coupled with image data. The physiological parameters may include health signals retrieved from IMD 6 or from one or more other medical device(s) 17, such as another IMD or a wearable device comprising one or more sensors.

Examples of ECG collection aspects include ECG collected directly from one of medical device(s) 17 (e.g., medical device(s) 6). In some examples, medical device(s) 17 may include a wearable device, such as an activity tracker, heart rate monitor, pulse monitor, pulse oximetry monitor, temperature monitor (e.g., core temperature monitor, surface temperature monitor). In addition, computing device(s) 2 may receive ECG that is collected from wearables or other ECG devices (e.g., medical device(s) 17). In some examples, computing device(s) 2 may provide for programmed connectivity (e.g., via a dropdown menu) with medical device(s) 17. Computing device(s) 2 may receive input, via the dropdown menu, from patient 4 or HCP indicating a target programming connection for one or more of medical device(s) 17 (e.g., a wireless connection). In some examples, the virtual check-in application of this disclosure includes a device-aware application. That is, computing device(s) 2 may store information regarding what device computing device(s) 2 is communicating with. In some instances, computing device(s) 2 may determine such information through a pairing process. In another example, computing device(s) 2 may receive such information as a download from a physician. In some examples, computing device(s) 2 may determine such information from user selection from a dropdown menu (e.g., a device dropdown menu).

In some examples, computing device(s) 2 may include device-aware aspects that are based on an interrogation of one of medical device(s) 17. In another example, computing device(s) 2 may receive device parameters and information as pushed from another device, such as from a push notification. In some examples, computing device(s) 2 may receive device information from another one of computing device(s) 2 operated by a HCP, where the HCP may populate the correct information via UI 22.

In some instances, computing device(s) 2 may receive physiological parameters or physiological parameter analysis results directly from another device or indirectly from another device, such as over network 10. In an illustrative example, computing device may receive an ECG or an image of an ECG from another device. That is, a scanner program may scan an ECG and upload the scan in any suitable document format. Likewise, a loader program may upload an image of an ECG for use by computing device(s) 2. In some instances, computing device(s) 2 may include the scanner program and/or the loader program. In such instances, computing device(s) 2 may upload the physiological parameter information to another device or store the parameter information to an internal storage (e.g., storage device 24).

In some examples, circuitry, e.g., processing circuitry 20 of computing device(s) 2, processing circuitry 64 of edge device(s) 12, processing circuitry 98 of data server(s) 94, or processing circuitry 40 of medical device(s) 17 may, prior to providing the second subsession, detect selection of a second interface tile, wherein a first interface tile corresponding to a first subsession and the second interface tile corresponding to a second subsession are distinct from one another. In an example, processing circuitry 20 may provide, in response to selection of the second interface tile, the second subsession of the interactive session.

In some examples, the top-level interface of computing device 502 may include the second interface tile. In another example, an interface for the first subsession may include the second interface tile, such that a user may navigate from the first subsession to the second subsession without necessarily reverting to the top-level interface.

Figure 13:
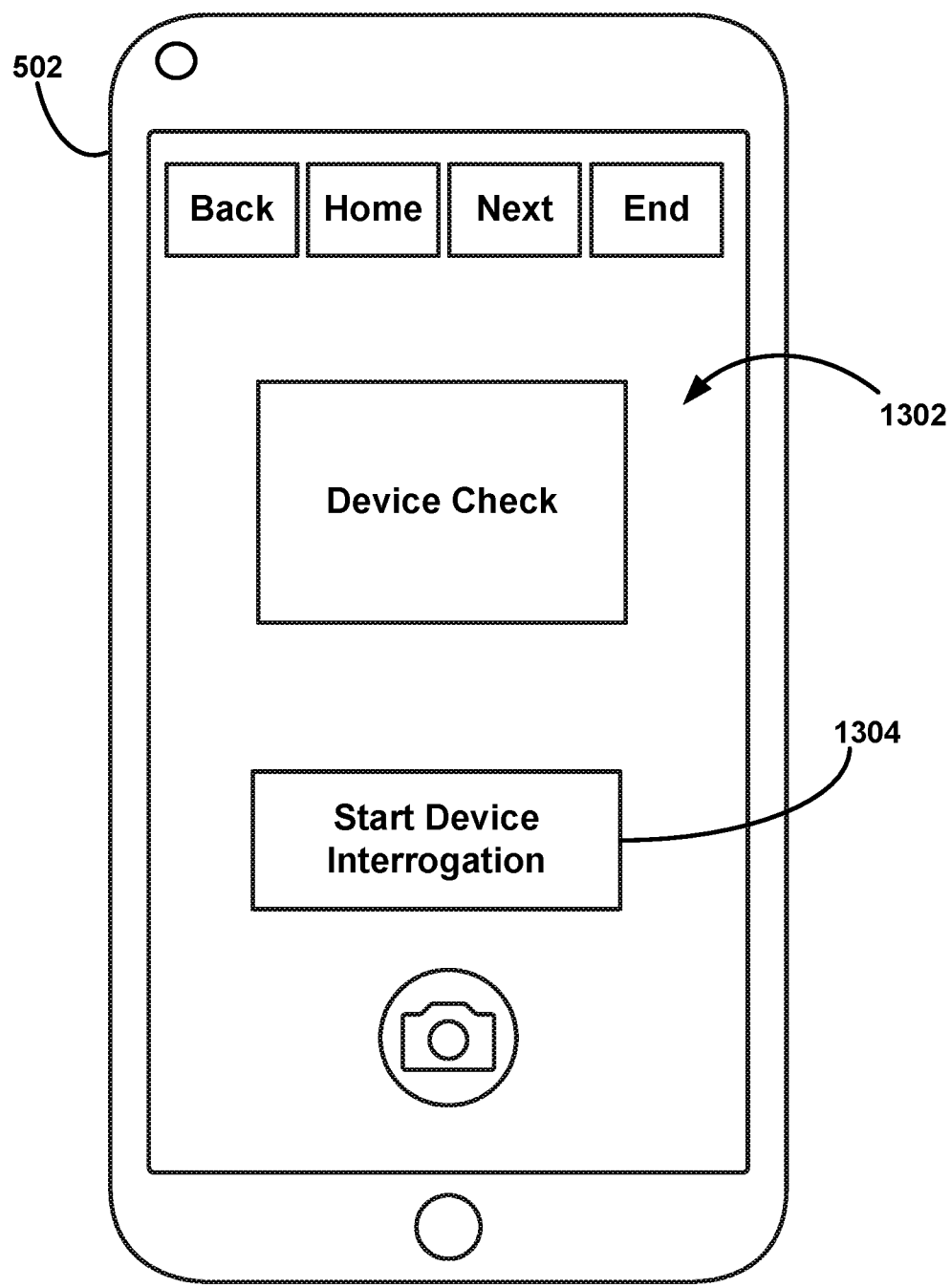
FIG. 13 is a UI visualization of an example device check interface, in accordance with one or more techniques of this disclosure.

FIG. 13 is a UI visualization of an example device check interface 1302, in accordance with one or more techniques of this disclosure. Device check interface 1302 illustrates an example interface that may be invoked or initialized upon user selection of the device check tile illustrated in FIG. 7 (e.g., tile 710).

Figure 14:
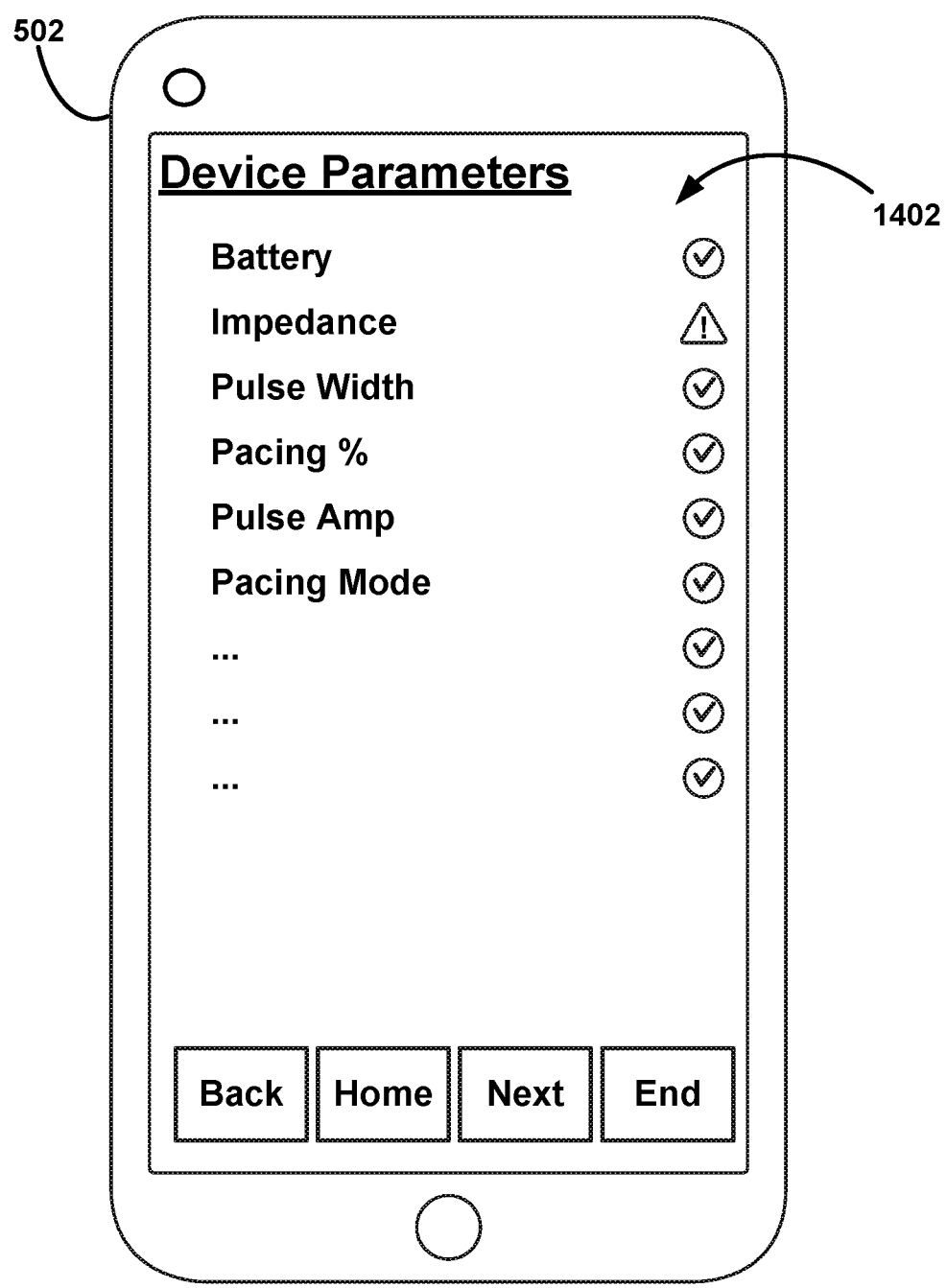
FIG. 14 is a UI visualization of an example device check interface, in accordance with one or more techniques of this disclosure.

FIG. 14 is a UI visualization of an example device check interface 1402, in accordance with one or more techniques of this disclosure. Invocation of device check interface 1402 may cause computing device(s) 2 to interrogate medical device(s) 17 (e.g., IMD 6). In an example, computing device(s) 2 may interrogate medical device(s) 17 via various close-range wireless communication protocols and telemetries. Computing device(s) 2 may populate device check interface 1402 with various parameters for the device check portion, as shown. In various examples, the backend system of a cloud-based implementation may push the interrogation information to the mobile device, or the mobile device app may initiate the interrogation locally at the mobile device. In any case, users may then audit the performance of medical device(s) 17 (e.g., IMD 6), by invoking the app and pinging the statistics as shown in FIG. 14. In the example of FIG. 14, the monitored statistics include, but are not necessarily limited to, battery strength, impedance, pulse width, pacing percentage, pulse amplitude, and pacing mode. In some instances, computing device(s) 2 may automatically schedule a routine device-check or follow-up based on the results of the interrogation.

In such examples, the subsession of interface 1302 and 1402 includes a device-check subsession, where processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the second set of data items. In an example, processing circuitry 20 may perform, via communication circuitry 26, an interrogation of one or more medical device(s) 17 corresponding to the patient. The one or more medical device(s) 17 may include IMD 6, and in some instances, other medical device(s) 17, such as wearable monitoring devices. Processing circuitry 20 may perform the interrogation by establishing a wireless communication connection with the respective medical device(s) 17. That is, processing circuitry 20 may receive, via a computing network, the second set of data items. In some examples, the computing device may receive medical device interrogation data over network 10, directly from the one or more medical device(s) 17, from one or more edge device(s) 12, or any combination thereof. In any case, processing circuitry 20 may determine, from the interrogation, the second set of data items, where the second set of data items include device interrogation data (e.g., battery, impedance, pulse width, etc.). In some examples, processing circuitry 20 may determine the post-implant report upon completion of the device-check subsession. That is, processing circuitry 20 may determine, from the set of data items obtained via the device-check subsession, that medical device(s) 17 satisfy one or more performance thresholds. In one example, processing circuitry 20 may compare interrogation data to what was read during implantation. In such examples, processing circuitry 20 may determine, based at least in part on the data items of the device-check subsession, a post-implant report. Examples of post-implant reports, and generation of such reports, are described herein (e.g., with reference to FIGS. 21-23).

Figure 15:
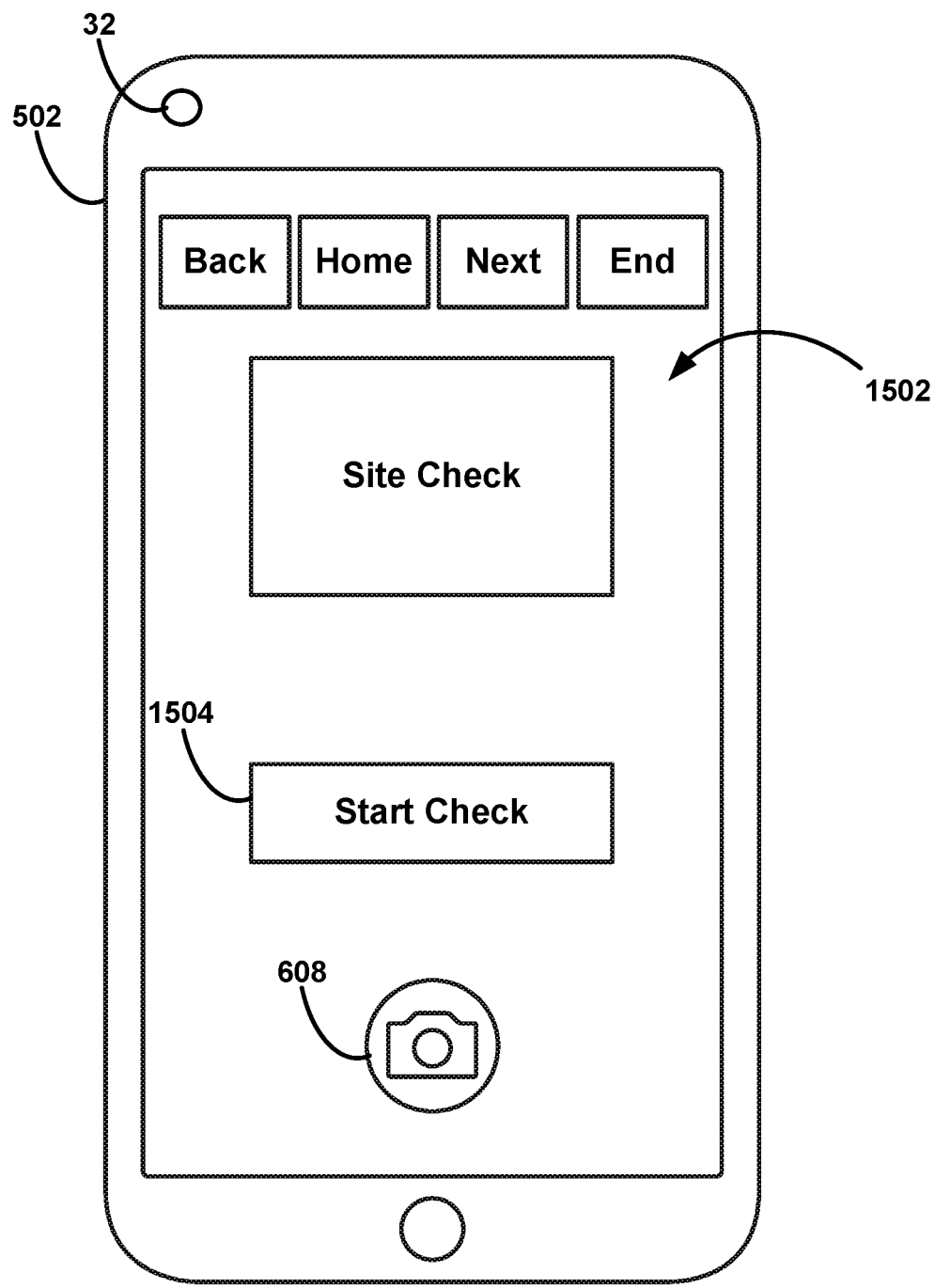
FIG. 15 is a UI visualization of an example site check interface, in accordance with one or more techniques of this disclosure.

FIG. 15 is a UI visualization of an example site check interface 1502, in accordance with one or more techniques of this disclosure. Site check interface 1502 illustrates the invocation or initiation of a site-check subsession upon the user selection of the site check tile illustrated in FIG. 7 (e.g., tile 712).

Site check interface 1502 may include a start check 1504 button and a camera icon 608 button. Camera icon 608 may automatically start a site-check subsession. In some examples, however, a user may wish to adjust camera parameters prior to starting. Although not illustrated, site check interface 1502 may include additional options to adjust various camera parameters. In addition, a user may adjust camera parameters on the fly while using the camera to capture images of the implantation site. In some examples, camera parameters include adjusting between a front-facing camera and another camera, lighting (e.g., infrared, thermal imaging, flash, etc.), zoom levels, focus, contrast, etc. Once ready, processing circuitry 20 may receive user selection, via UI 22, of start check 1504 in order to advance to a next page (e.g., interface) of the site-check subsession (e.g., a next graphical interface of the site-check UIs).

Figure 16:
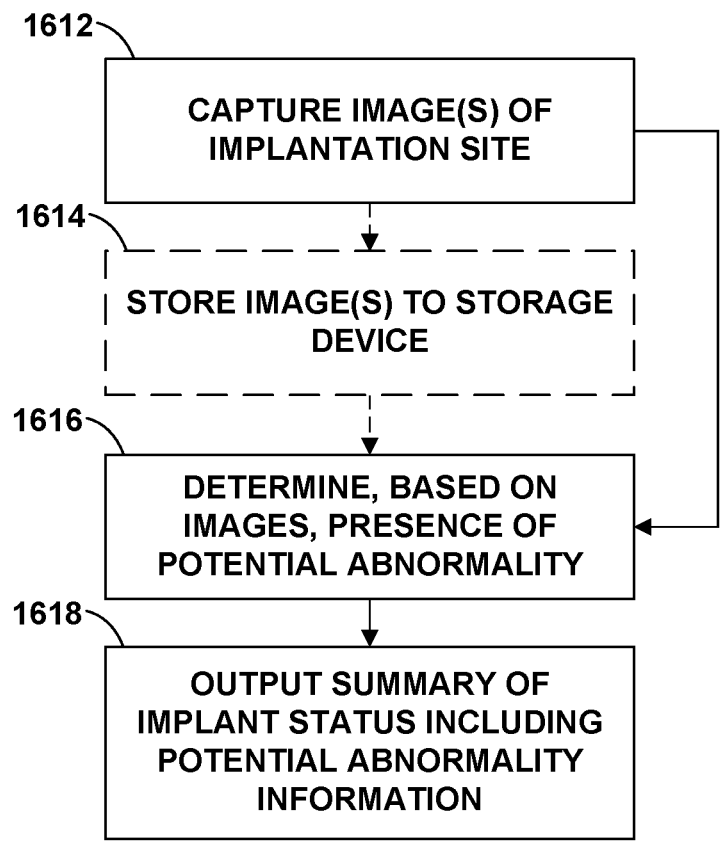
FIG. 16 is a flowchart illustrating an example method of utilizing imaging techniques, in accordance with one or more techniques of this disclosure.

FIG. 16 is a flowchart illustrating an example method of utilizing image acquisition, recognition, and/or image processing techniques, in accordance with one or more techniques of this disclosure. Described with reference to the interfaces of FIGS. 15, 17, and 18, for example, processing circuitry, e.g., processing circuitry 20 of computing device(s) 2, processing circuitry 64 of edge device(s) 12, processing circuitry 98 of server(s) 94, or processing circuitry 40 of medical device(s) 17, may receive a UI command to start the site-check subsession (e.g., a wound check subsession). In one example, processing circuitry 20 may receive indication of user input selecting start check icon 1504.

In an illustrative example, a method for imaging an implantation site is described (e.g., an image capture process). Camera 32 captures image(s) of or adjacent the implantation site of one of medical device(s) 17 (e.g., IMD(s) 6 (1612). Processing circuitry 20 may capture images at a specific point in time following implantation of the medical device 17 (e.g., IMD 6). In some examples, a first one of computing device(s) 2 may store the various images to storage device 24 (1614). In addition, or alternatively, computing device(s) 2 may transmit the various images to a secure backend system. Example backend systems include edge device(s) 12, server(s) 94, and/or other components of network 10 (e.g., Medtronic CareLink® Network). Processing circuitry of the backend system (e.g., processing circuitry 64, processing circuitry 98, etc.) may process the various images and/or route the images to various other devices. Processing circuitry 20 may, in some examples, store image(s) to storage device 50 of medical device(s) 17. Similarly, processing circuitry 20 may store such data to storage device 62 of edge device(s) 12 or to storage device 96 of server(s) 94.

Processing circuitry 20 may guide the user by providing scheduled reminders. The reminders may be pushed to a computing device 2 of the user. In addition, a HCP (e.g., the prescribing physician) can access the interactive session interface(s) (e.g., site-check subsession interface) to follow-up on patient 4 when the implantation site does not show signs of healing over time. That is, processing circuitry 20 may determine an abnormality, such as an implantation site that does not display signs of healing over time, and as such, may transmit a notification to a computing device 2 of the HCP, such that the HCP may access the interactive session interface(s) (e.g., site-check subsession interface), including images, physiological parameters, etc., via UI 22.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may deploy, as part of the site-check subsession, a ML model (e.g., a DL model) and/or AI engine that analyzes, for abnormalities, each captured image from a site-check subsession. In an illustrative and non-limiting example, the site-check subsession may provide three levels of detections: "abnormality present," "abnormality absent," "uncertain." In an example, where processing circuitry 20, via the site-check subsession, detects an abnormality in any of the images with a high likelihood, then processing circuitry 20 may determine an abnormality presence at that time. Where processing circuitry 20 determines there to be no abnormality in all images with a high likelihood, then processing circuitry 20 may determine an abnormality absence at that time. In some examples, processing circuitry 20 may transmit images from the site-check subsession to another one of computing device(s) 2 (e.g., a computing device 2 of a technician or HCP) for human expert review. The "expert" can be a trained professional who can review images of the body of patient 4 and identify some potential abnormalities and/or can capture images of a patient's implantation site with relative clarity. If the human expert detects an abnormality, the patient can be asked to follow-up with the prescribing physician.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine thresholds for abnormality presence or absence. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine parameters of the site-check subsession, including thresholds for abnormality detection, based on based on whether the implantation site hosts a first-time implant or an implant that has been changed out, IMD type (e.g., CIED type), skin tone and age of patient 4 being monitored, etc.

In an illustrative example, processing circuitry 20 may determine a sensitivity level for the site-check subsession (e.g., abnormality detection algorithms, etc.). To determine the sensitivity level, processing circuitry 20 may determine medical device information (e.g., IMD information) with respect to medical device(s) 17, physiological parameters (e.g., ECG), etc. In such examples, processing circuitry 20 may determine the sensitivity level based on the determined medical device information, physiological parameters, etc. In an illustrative and non-limiting example, processing circuitry 20 may determine a prevalence factor that defines the prevalence of abnormalities (e.g., infections) for a particular type of IMD. In another example, processing circuitry 20 may determine an impact factor that defines the impact an abnormality (e.g., device malfunction, infection, etc.) may have with respect to patient 4 and medical device(s) 17 (e.g., IMD 6). Processing circuitry 20 may determine, from such information or other information, a sensitivity level that yields a more conservative algorithm that errs on the side of over detection, rather than under detection, of abnormalities. That is, it may be important to be more conservative and not miss a potential abnormality (e.g., infection, malfunction of an IMD, etc.) because doing so may then provide high-energy life-saving therapy. In one example, IMD 6 may malfunction to a point where it is unable to determine temperature or migration data of IMD 6, such that when a potential abnormality is detected from an image, processing circuitry 20 may determine not to rely on data received from IMD 6 in order to identify, according to an adjusted sensitivity level, a likelihood of the abnormality being an actual abnormality.

In one further example, processing circuitry 20 may determine a higher (e.g., more conservative) sensitivity level relative to other less conservative sensitivity levels, when processing circuitry 20 determines, for example, that a stimulation generator (not shown) and leads (not shown) are from different manufacturers but are being combined into a single IMD 6. That is, the likelihood of a potential abnormality may be higher in such instances where different items are being combined from different manufacturers into a single device, and thus, processing circuitry 20 may adjust the sensitivity level so as to be a higher sensitivity level in such instances. In some examples, processing circuitry 20 may adjust the sensitivity level (e.g., a built-in calculation bias) for identifying particular abnormalities based on a duration of time IMD 6 has been implanted. This is because certain abnormalities (e.g., pocket infections) may be most common during, for example, the first year post-implant, and as such, a higher sensitivity level may be utilized during the particular timeframe (e.g., the first year) and/or a lower sensitivity level may be utilized during another time frame (e.g., after the first year).

In another example, medical device(s) 17 (e.g., IMD 6) may include a LINQ™ ICM. In such instances, processing circuitry 20 may employ a detection algorithm that has a different sensitivity level for the LINQ™ ICM compared to that of a sensitivity level used for other medical device(s) 17 (e.g., a pacemaker implant). That is, the detection algorithm may employ a particular sensitivity level where the medical device information indicates that the medical device was implanted as part of a particular type of procedure (e.g., an out-patient procedure). In addition, processing circuitry 20 may determine from the IMD information that a schedule for virtual check-ins, or other types of check-ins, are scheduled at a particular interval (e.g., regular intervals, irregular intervals, frequent intervals, infrequent intervals, etc.). In another example, processing circuitry 20 may determine a frequency by which the virtual monitoring service is receiving and/or monitoring medical device diagnostics, such as diagnostics from medical device(s) 17 (e.g., IMD 6, wearable heart rate and/or activity monitor, etc.).

In an illustrative and non-limiting example, processing circuitry, e.g., processing circuitry 20 of computing device(s) 2, processing circuitry 64 of edge device(s) 12, processing circuitry 98 of server(s) 94, or processing circuitry 40 of medical device(s) 17, may employ a first sensitivity level when determining an abnormality for a first type of implant (e.g., a pacemaker implant), whereas the processing circuitry may employ a second sensitivity level when determining an abnormality for a second type of implant (e.g., an ICM). In an example, the first sensitivity level may be higher than the second sensitivity level because processing circuitry 20 may have determined that the implant procedure of a second type of implant was out-of-office or out-patient, that there are one or more regularly-scheduled patient follow-ups via system 100 and/or system 300, and that processing circuitry 20 is continuously, or at least semi-continuously, monitoring diagnostic device data of a medical device, such as would results from regular data transmissions from medical device(s) 17 to computing device(s) 2 and/or to other devices (e.g., edge device(s) 12, etc.) of system 300.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine parameters of an imaging program of camera 32, including thresholds for abnormality detection, based on whether the implantation site hosts a first-time implant or an implant that has been changed out, IMD type (e.g., CIED type), skin tone and age of patient 4 being monitored, etc. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine parameters of the imaging program based on information regarding various abnormality control procedures. In an illustrative examples, an abnormality control procedure may include information that a HCP (e.g., a surgeon or implanting clinician) used Medtronic's TYRX™ Absorbable Antibacterial Envelope, or another similar element, during implantation of the medical device. As will be understood, TYRX™ is a mesh envelope that holds an implantable cardiac device, implantable neurostimulator, or other IMD. Processing circuitry 20 may determine a biasing factor for the based on the presence of such control procedures. This is because TYRX™ is designed to stabilize the device after implantation while releasing antimicrobial agents, minocycline and rifampin, over a minimum of seven days, and thus, the likelihood of an abnormality during that time is lower relative to an implant that does not include such control procedures. In other words, patients with a TYRX™ envelope as part of an implant generally tend to have a lower chance of infection than patients without a TYRX™ envelope. In any case, the various abnormality detection algorithms of this disclosure may be configured to be more sensitive and/or less specific (e.g., imaging program parameters) for non-TYRX™ patients as compared to imaging program parameters used with respect to TYRX™ patients.

In some examples, AI engine(s) and/or ML model(s), e.g., AI engine(s) 28 of computing device(s) 2, AI engine(s) 44 of medical device(s) 17, ML model(s) 30 of computing device(s) 2, or ML model(s) 46 of medical device(s) 17, may determine the sensitivity level based on training of the AI engine(s) and/or ML model(s). In an example, in order to determine sensitivity levels, processing circuitry, e.g., processing circuitry 20 of computing device(s) 2, processing circuitry 64 of edge device(s) 12, processing circuitry 98 of server(s) 94, or processing circuitry 40 of medical device(s) 17, may train the AI engine(s) and/or ML model(s) on data sets, including prevalence data (e.g., rate of infection with particular types of medical device(s) 17), severity data, data on likelihood of abnormalities, potential or actual impacts of particular types of abnormality (e.g., device malfunction and infection abnormalities, etc.), IMD information (e.g., device manufacturing information, implantation procedure information), etc. Upon being trained on such data, the AI engine(s) and/or ML model(s) may determine a sensitivity level that corresponds to each individual monitoring event (e.g., device contexts) or class of monitoring events of patient 4.

Advantages of applying such sensitivity levels include allowing monitoring system 100 to efficiently allocate processing, memory, and/or power resources, by scaling the sensitivity level according to individual needs. In addition, the sensitivity level may govern a rate at which computing device(s) 2 receive data from other devices (e.g., transmission rates, etc.). In this way, computing device(s) 2 may receive more data, for example, in situations involving a higher likelihood of an abnormality being present, and receive less data in other situations. This selective use of sensitivity levels may also assist with bandwidth considerations, such as by limiting an amount of communication data that may otherwise consume a large amount of bandwidth of system 100 and/or system 300.

In some examples, the site-check subsession, including AI engine(s) 28 and/or ML models(s) 30 may be trained on several images/videos that have been labeled as corresponding to an abnormality or not (e.g., infection or not). In one example, a video may provide evidence of a gait of patient 4. In such examples, processing circuitry 20 may include a site-check subsession executed by AI engine(s) 28 and/or ML model(s) 30. AI engine(s) 28 and/or ML model(s) 30 may be trained with data that has been labeled based on improvement of an implantation site or deterioration of the implantation site. In an example, AI engine(s) 28 and/or ML model(s) 30 can detect, as an implant status, implantation site "improvement" or implantation site "non-improvement" over time.

In some examples, processing circuitry 20 may acquire images of implantation site from multiple site-check subsessions over time after the implantation. Processing circuitry 20, via the site-check subsession, may chronologically analyze the time-aging of the implantation site with different thresholds to detect improvement or non-improvement of the implantation site. The prescribing physician can use the system to only follow-up on patients whose implantation site does not show signs of healing. In some examples, processing circuitry 20 may operate according to a time-lapse mode. During time-lapse, processing circuitry 20 may, for example, collect images chronologically (e.g., on a daily schedule) and stitch them together over the 2-12 weeks period post implant. This will allow for a time-sequence presentation of the images and time-sequence analysis. In such examples, processing circuitry 20 may train AI engine(s) 28 and/or ML model(s) 30 on a rate of change of implantation site healing (e.g., infection spread or growth). In some examples, rather than assess the implantation site per se, AI engine(s) 28 and/or ML model(s) 30 may instead analyze the progression of the implantation site healing (e.g., a delta between registered and superimposed successive images that track differences between the images over a multiweek period). In some instances, AI engine(s) 28 and/or ML model(s) 30 may track differences between still-images in order to determine a delta at the implantation site over time (e.g., a delta between healing of the implantation site in a time-lapse). Processing circuitry 20 may then determine abnormalities based on an analysis of the delta at the implantation site over time.

In some examples, processing circuitry 20 may determine, based on the images, the presence of a potential abnormality (1616). In one example, the backend system may route the various images to a computing device 2 of an expert technician trained in identifying abnormalities from images of implantation sites. In another example, the backend system may route the various images to a second one of computing device(s) 2 that has a particular configuration of AI engine(s) 28 and/or ML model(s) 46 trained in identifying abnormalities from implantation-site images. In some examples, when identifying the abnormality, processing circuitry 20 may determine, based on an image of the implantation site (e.g., the captured image(s) of the implantation site), a likelihood of the abnormality (e.g., a severity of the abnormality). In some instances, processing circuitry 20 may deploy a probability model to determine the likelihood of the abnormality. In one example, processing circuitry 20 may determine a potential severity of the potential abnormality based on an analysis of the captured image(s).

In some examples, processing circuitry 20 may output a summary of the implant status, including potential abnormality information (1618). In one example, the backend system may transmit a report back to the first one of computing device(s) 2 indicating a result of the image analysis performed by the backend system. In an illustrative example, processing circuitry 20 may generate, based on the likelihood of the abnormality, a summary report identifying the abnormality, where the summary may include information regarding a determined potential infection. In some examples, processing circuitry 20 may store all image data and labels (e.g., expert labels) in a database and computation system to continuously improve and deploy the automated abnormality detection system (e.g., AI engine(s) 28 and/or ML model(s) 30). In any case, processing circuitry 20 may output the summary report. In some examples, the summary report includes the one or more frames of the image data. In such examples, processing circuitry 20 may generate a summary report (e.g., a post-implant report) including the one or more frames of the image data, where that image data was received prior to the abnormality determination and used at least in part to determine the abnormality determination. In some instances, the report includes the frames that correspond to one or more camera angle(s) in which the potential abnormality was identified (e.g., left lateral vs. right lateral). In some examples, when an abnormality is detected, processing circuitry 20 may output one or more various image(s) of the implantation site from that subsession for human expert review.

In some examples, computing device(s) 2 may determine, from the interactive session, whether to configure the interactive session to include a pass-thru mode, where patient 4 does not need to come in for a consultation (e.g., for a post-implantation infection consultation). In such examples, computing device(s) 2 may provide the HCP with access to the various images (e.g., still-images). As such, the HCP may, in some examples, decide whether the implantation site is healing as expected or whether an in-person follow-up is warranted.

In some examples, a HCP may have programmed and transmitted the interactive session program to an application database (e.g., a program datastore). In another example, a HCP may have uploaded the interactive session program directly to computing device(s) 2. That is, computing device(s) 2 may access the interactive session program from an application database. In an example, the interactive session program may include an imaging program for conducting a site-check subsession. That is, the imaging program may be part of the interactive session program, whereas in some instances, the imaging program that executes the site-check subsession may be separate from the interactive session program. In addition, some aspects of the site-check subsession program may be controlled by a separate programming application, such as a camera application native to the operating software of one of computing device(s) 2 (e.g., an OEM camera application), while other aspects may be controlled by the interactive session programming application, such as augmented overlays, camera parameter control (e.g., zoom, contrast, focus, etc.), such that the interactive session software may work in tandem with other software applications (e.g., camera applications, augmented reality applications, etc.) or devices running such software applications thereon (e.g., augmented reality headsets, etc.).

The HCP may configure the interactive session to function in the pass-thru mode where the patient may forego the post-implant consultation entirely until execution of the interactive session results in an identified potential abnormality, such as one that satisfies a predefined threshold. In such examples, the HCP may, in any case, access the images in order to determine whether an abnormality is present, regardless of whether processing circuitry 20 determines the presence of a potential abnormality. In this way, the HCP (e.g., a physician, nurse, etc.) may independently adjudicate the image(s) independent of an automated image analysis of the site-check subsession, in order to independently determine a status of the implant, including an implantation site healing status.

Figure 17:
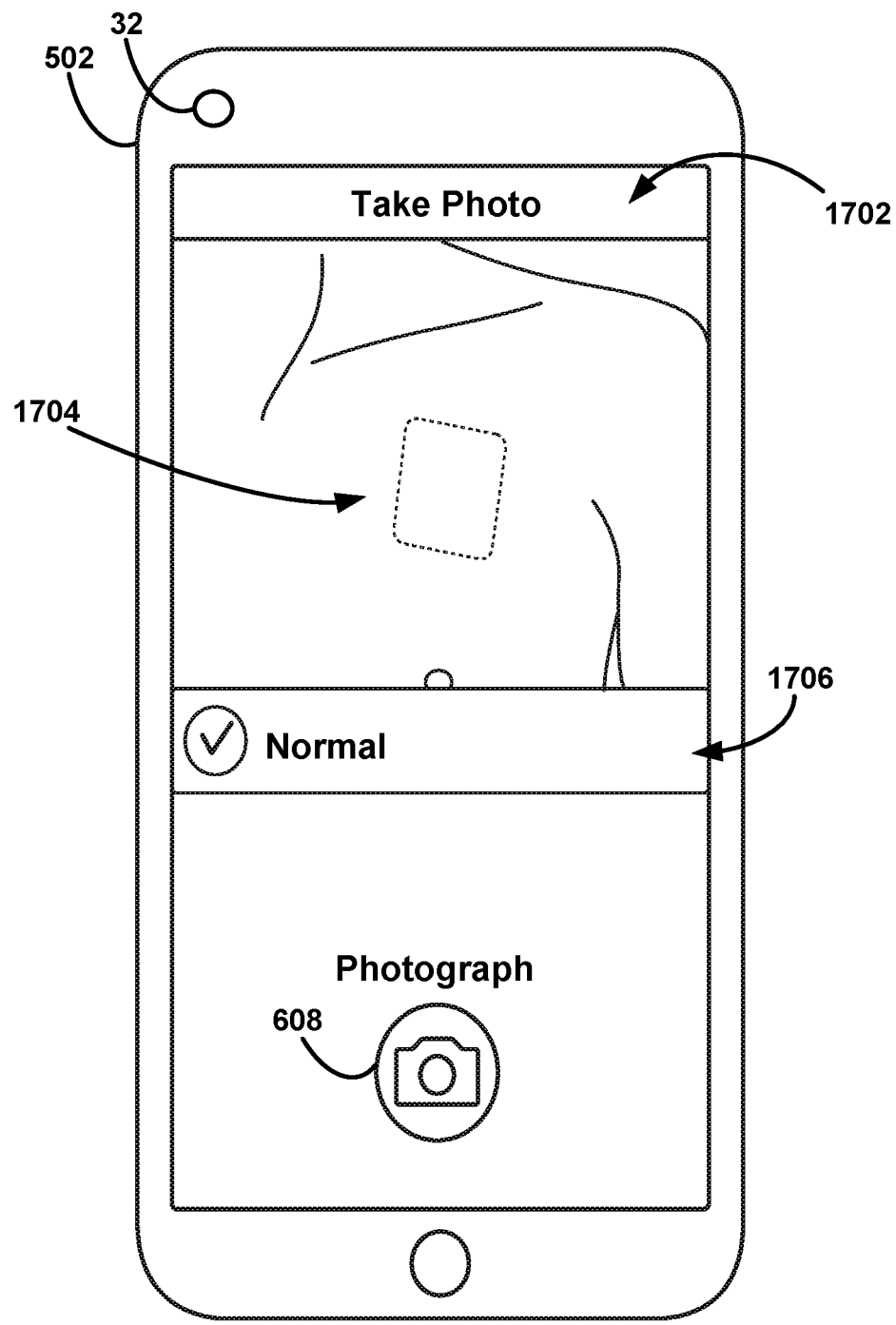
FIG. 17 is a UI visualization of an example site check interface, in accordance with one or more techniques of this disclosure.

FIG. 17 is a UI visualization of an example site check interface 1702, in accordance with one or more techniques of this disclosure. Site check interface 1702 includes a photographs icon 608 configured to cause camera 32 to capture images of implantation site 1704.

In some instances, a user may point the camera at implantation site 1704, in which case, processing circuitry 20 may automatically perform an abnormality detection, with or without already receiving a command to capture an image. In addition, processing circuitry 20 may cause camera 32 to automatically capture an image of the implantation site when processing circuitry 20 detects an abnormality. Once a photo has been captured, an implant status indicator 1706 may appear indicating a status of the implant, including the implantation site 1704. In the example of FIG. 17, the implantation site is indicated as being "Normal". In some examples, processing circuitry 20 may perform such a detection by comparing a first image (automatically or manually captured) with one or more baseline images (e.g., a first set of images captured during a predetermined period of time as measured from implantation or as measured from when the first image is taken). In one example, processing circuitry 20 may apply a sliding window to a set of historical images taken over time to filter images (e.g., older images) from the one or more baseline images and compare the first image with the one or more filtered baseline images. In addition, processing circuitry 20 may determine a projection from the one or more filtered baseline images and determine, at a prospective time, a reference (e.g., reference alteration characteristics) that the first image may be compared against to determine the presence of an abnormality at the imaged site.

In some examples, processing circuitry 20 may implement regional comparison zones for differential diagnostics (e.g., Dx). Processing circuitry 20 may perform a gradient analysis of implantation site 1704 and, for example, sternum areas for different skin tones, to determine a differential diagnostic. Processing circuitry 20 may reference the differential diagnostic to determine whether a potential abnormality is present at implantation site 1704. AI engine(s) 28 and/or ML model(s) 30 also use various measurements in the user-provided picture to determine whether the implantation site is within a threshold of the "normal" state. In some instances, processing circuitry 20 may overlay a ruler or other augment or overlay on the image to assist the user with capturing an image useful for measurements. That is, processing circuitry 20 may provide an augment or another frame that the user can use to get the correct distance and/or perspective of the implantation site. In an illustrative example, processing circuitry 20 may guide a user to image the implantation site where camera 32 is a target distance from the implantation site and in some instances, from a second target distance from the implantation site. Processing circuitry 20 may further guide a user to image the implantation site at a target angle relative to the implantation site or relative to a reference plane of camera 32 (e.g., a starting position of computing device(s) 2). In such examples, processing circuitry 20 may use overlays, augmented rulers, etc., such as in an augmented reality implementation, in order to capture image(s) at particular angles (e.g., a particular view of the implantation site), with the implantation site at a particular relative size in a frame of image data, etc.

In some examples, processing circuitry 20 may train AI engine(s) 28 and/or ML model(s) 30 to discern relative measurements with respect to color and marks. In this way, processing circuitry 20 may compensate for different appearances of a wound on different skin colors, across different patient demographic cohorts, etc. In some examples, the image processing AI may use regional comparisons within the same picture to distinguish the implantation site from areas of the skin of patient 4 that are unaffected by the implantation (e.g., to derive relative or delta information). The image processing AI may also be trained to compensate for differences between systemic infections and implant site-originated infections, such as at the pocket or incision. In some examples, processing circuitry 20 may deploy AI engine(s) 28 and/or ML model(s) 30 to determine, from a captured image, Red, Green, and Blue (RGB) image details, Pantone®, and other color schemes. In addition, AI engine(s) 28 and/or ML model(s) 30 to determine, from a captured image, shape of an implantation site wound closure, whether the image comprises glossiness, etc. Processing circuitry 20 may, based on the various image processing techniques, determine whether an image of an implantation site includes a potential abnormality or if the implantation site otherwise satisfies the predefined threshold of the "normal" state.

Figure 18:
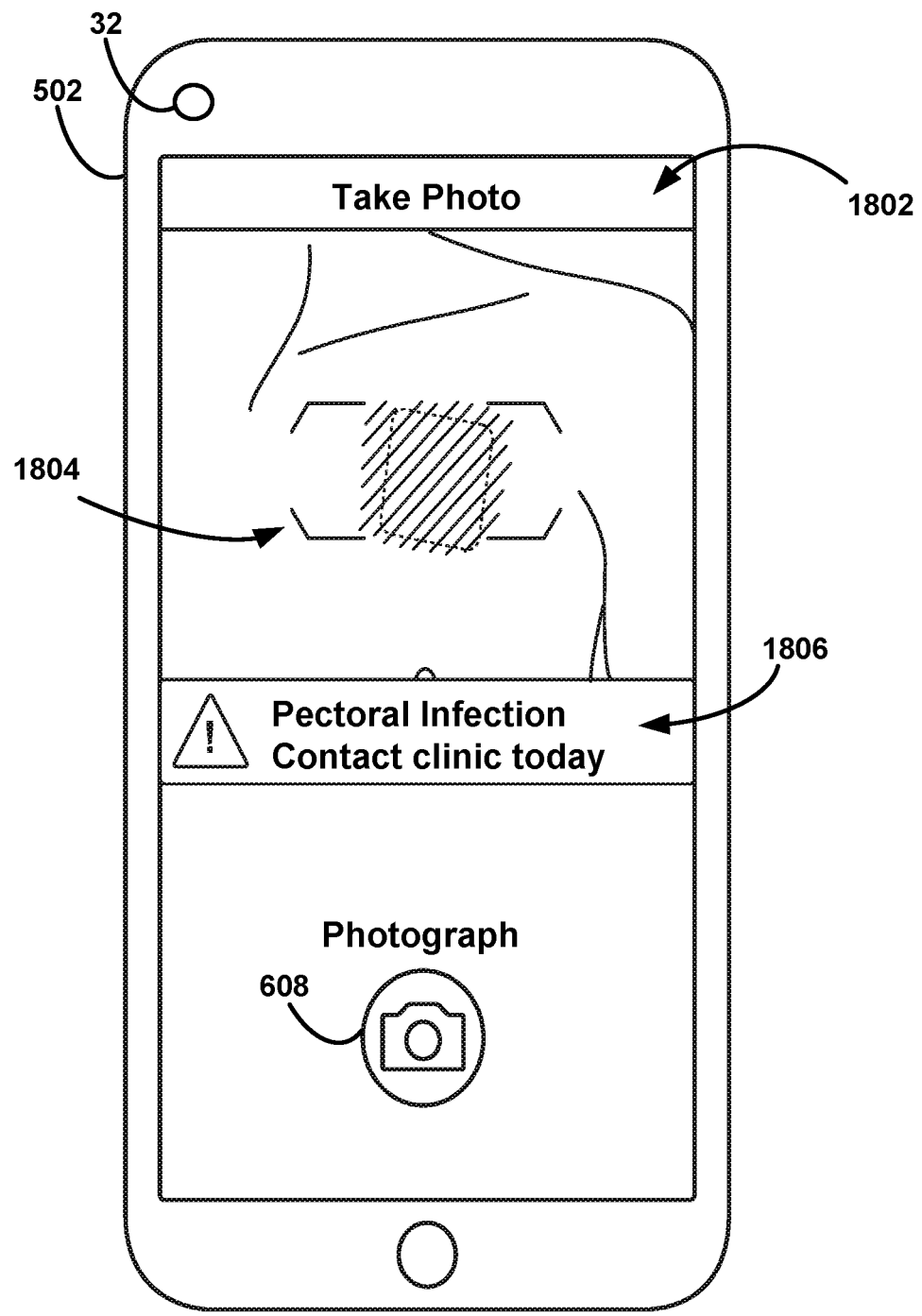
FIG. 18 is a UI visualization of an example site check interface, in accordance with one or more techniques of this disclosure.

FIG. 18 is a UI visualization of an example site check interface 1802, in accordance with one or more techniques of this disclosure. The example site check interface 1802 of FIG. 18 illustrates an abnormal implantation site outcome. When detecting an abnormality processing circuitry 20 may provide a visual alert 1806. Processing circuitry may include in visual alert 1806 descriptive information regarding the potential abnormality. In some examples, processing circuitry may include with visual alert 1806 a medical intervention instruction for the user to perform some action (e.g., contact clinic, etc.).

In some examples, processing circuitry 20 may provide augmented reality overlay 1804 on interface 1802 (e.g., an image overlay). Processing circuitry 20 may do so in order to assist a user in capturing an image of the implantation site at a particular angle, with a size reference, etc. In addition, AI engine(s) 28 and/or ML model(s) 30 may provide adjustments for a respective algorithm based on a tendency that, as an alteration of the implantation site occurs (e.g., a gradual healing, a gradual decline in healing, etc.), the post-op images will change as well. In some examples, processing circuitry 20 may train AI engine(s) 28 and/or ML model(s) 30 to detect deviations from the "healthy" state, in some examples. The healthy state may include characteristics of the implantation site from a previous site-check subsession in which no abnormality was detected.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may identify an image overlay to augment a set of preview frames and guide a user in capturing images in a particular manner. In one example, processing circuitry 20 may determine patient data corresponding to the patient. The processing circuitry 20 may, in turn, determine the image overlay data based at least in part on the patient data. As discussed herein, patient data includes various information about the IMD patient including any one or more of: image data of an implantation site (e.g., an explant site), implantation site characteristics, patient identification data (e.g., patient name, authentication data, login information, etc.), patient-input data (e.g., input via UI 22), or other information regarding IMD 6, including date of implant or explant, IMD component details (e.g., leads, wiring routes, etc.). The image data may include a current image or a previously taken image, such as one taken shortly after implantation or before an implantation procedure. In such examples, the image overlay data may correspond to the IMD and/or other components of the IMD. As used herein, preview frames generally refer to the frames of image data displayed to a user prior to image capture and/or during an image capture. The preview frames represent what a user observes on a display screen of, for example, computing device(s) 2. In any case, the image overlay data defines an image overlay configured to augment the set of preview frames. In some instances, the image overlay may include a wireframe that resembles an outline of a body of a subject, such as patient 4 or a generic silhouette.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may obtain images of the body of the patient, wherein the images correspond to the image overlay and represent one or more locations of the body in which one or more components of the IMD coincide (e.g., IMD 6, leads of IMD 6). In one example, the images may represent a right or left pectoral region of the body, where IMD 6 comprises an implant configured to be implanted in a pectoral region of the body. In another example, the images may represent a portion of the neck of patient 4, where the user is tasked with imaging portions of the neck where leads of IMD 6 coincide, such as leads routed from IMD 6 to a region of the brain of patient 4. From the images, processing circuitry 20 may determine an abnormality (e.g., an infection, discharge, etc.) at the one or more locations of the body in which one or more components of the IMD coincide.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the image overlay data to include a hollow outline of a body with an outline of a region of interest (e.g., an implantation site), such that the user may align the image properly to capture the region of interest at particular angles, sizes, orientations, etc. In an example, processing circuitry 20 may determine the image overlay data to include a first portion comprising an outline of at least one portion of the body of patient 4, where the portion of the body corresponds to an implantation site of the one or more IMD components, and determine a second portion of the image overlay data, where the second portion comprises an inner overlay that is inside of the outline and that represents the region of interest (e.g., an implantation site).

In an illustrative and non-limiting example, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, based at least in part on the patient data, that the IMD coincides with a particular lateral side of a pectoral region of the body. In an example, processing circuitry 20 may determine the first portion of the image overlay data so as to represent the particular lateral side of the pectoral region of the body. In some examples, processing circuitry 20 may determine the second portion of the image overlay. In such examples, processing circuitry 20 may determine, based at least in part on the patient data, that implantation site 1704 comprises a particular incision angle relative to the outline of the at least one portion of the body of patient 4. That is, the image overlay data may be dynamic and based on the particular context of the imaging of patient 4, such as based on the type of medical device 17, location of medical device 17, etc. In any case, processing circuitry 20 may determine the second portion so as to represent the implantation site comprising the particular incision angle.

In addition, processing circuitry, e.g., processing circuitry 20 of computing device(s) 2, processing circuitry 64 of edge device(s) 12, processing circuitry 98 of server(s) 94, or processing circuitry 40 of medical device(s) 17, may obtain one or more images of the body in accordance with the image overlay. In an example, processing circuitry 20 may obtain the images of the body by determining, from a set of preview frames, that the second portion of the image overlay coincides with the implantation site of the one or more IMD components. In response to determining the overlay, processing circuitry 20 initiate an automatic capture of the images of the body of patient 4. As used herein, "automatically" or "automatic" generally means without user intervention or control.

In another example, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the image overlay data from a library of image overlays. In an example, processing circuitry 20 may determine a static image overlay configured to provide a border for aligning the implantation site within the static image overlay. In an illustrative example, the border may include a broken-lined box shape, similar to overlay 1804 shown in FIG. 18. In such examples, processing circuitry 20 may retrieve the static image overlay from an overlay library that includes the at least one image overlay. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, based at least in part on patient data, IMD information, and/or a template overlay (e.g., a static image overlay), a custom image overlay as the image overlay that is customized for patient 4. In an illustrative example, processing circuitry 20 may obtain the images of the body by detecting movement of computing device 2 (e.g., via accelerometer data), and compensating for the movement by maintaining a particular orientation of the image overlay relative to the set of preview frames and the one or more locations of the body of patient 4.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the image overlay data by receiving, via camera processor(s) 38, a subset of the preview frames, and determining the image overlay data based on the subset of the preview frames. In such examples, AI engine(s) 28 and/or ML model(s) 30 may determine an initial estimation as to what the scar/implantation site looks like and what patient's body looks like (shoulder frame, build, etc.) based on patient data, IMD information, etc. Then, as camera 32 is pointing at the implantation site, AI engine(s) 28 and/or ML model(s) 30 may fine-tune, or morph in real-time, the image overlay to better frame the wound site with reference to other characteristics of the body of patient 4. In this way, the user may be guided by the image overlay to accurately align the implantation site within the overlay outline in such a way that is then useful for computing device 2 to analyze image captures of the implantation site and know how the wound site is angled on the body, size of the wound site, etc., in accordance with one or more of the various techniques of this disclosure. In addition, the image overlay data may be used to train the AI to determine image overlays for future imaging sessions. In another example, processing circuitry 20 may use a template overlay as an initial guess, or may use an already-modified template, and then the template may be modified in real-time once actual image data is being received by camera processor 38. In such examples, processing circuitry 20 may customize the image overlay to fit or mold to the build/frame of the body of patient 4 in addition to representing other characteristics that may be present in the image of the implantation site (e.g., collar bone for chest implant, hairline for DBS implants, etc.).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the image overlay data based on a determination as to a particular camera configuration of camera 32. In such examples, processing circuitry 20 may determine whether a front-facing or rear-facing camera of a mobile computing device is being used to capture images of the body of patient 4 or whether camera 32 is a standalone camera unit that a user may stand near such that camera 32 may capture images of the body of patient 4. In an illustrative example, processing circuitry 20 may require respective mirror images for the image overlay when the camera being used is a rear facing camera of a mobile computing device, as opposed to a front facing camera of the mobile computing device. In addition, camera configurations may include number of cameras (e.g., dual camera, triple camera) and types of lenses (wide angle, 360° lens, etc.), which would require different image overlays depending on the camera being used. In such examples, processing circuitry 20 may determine the image overlay data based at least in part on the camera configuration. Processing circuitry 20 may automatically capture an image of the implantation site when the image overlay defined by the image overlay data overlaps with the implantation site or other bodily site of patient 4 that is of interest. As used herein, an "overlap" may not include a perfect overlap, but may involve at least a substantial overlap, such that a particular percentage of the bodily site overlaps with the image overlay. In an example, when 80-90% of an implantation site is within the boundary of a particular portion of an image overlay, processing circuitry 20 may determine that an overlap exists, such that the image overlay portion substantially overlaps with the bodily site.

In such examples, the image overlay data may be configured to guide an image capture of the body of patient 4 relative to particular distances from the one or more computing devices to a surface of the body. In some examples, processing circuitry 20 may determine the image overlay data by creating, via an overlay generator (e.g., AI engine(s) 28 and/or ML model(s) 30, a wireframe (e.g., a custom wireframe, a template wireframe, etc.), where the overlay generator is trained to generate wireframes based on patient data. A wireframe generally refers to an augment that includes an outline, such as a hollow outline, that is used to align an object in a scene being captured within the wireframe. The user may adequately perceive the object in the scene through a wireframe in the foreground and perceive the wireframe in the foreground, as well, so as to augment a frame of image data as would be appreciated in the art. In some examples, obtaining the images of the body of patient 4, may include receiving, via communication circuitry 26, one or more frames of image data, wherein the one or more frames include the images of the body of patient 4. In another example, obtaining the images of the body of patient 4 includes capturing video data of the one or more locations of the body of the patient (e.g., with assistance from the image overlay). In such instances, processing circuitry 20 may determine the abnormality comprises identifying the abnormality from the video data and determine a post-implant report based on identification of the abnormality.

As described herein, processing circuitry 20 may use an image overlay (e.g., a box, a wireframe, etc.) to determine only a first set of reference images. Processing circuitry 20 may then align subsequent images with the reference images. In one example, processing circuitry 20 may perform an implantation site detection algorithm to detect an implantation site in a subsequent image, isolate an image of the implantation site from a remainder of the image (e.g. define coordinates or regions of a frame including the implantation site), and adjust the image, including the detected implantation site, to align with an alignment of the reference set of images. In addition, processing circuitry 20 may operate a detection algorithm (e.g., AI engine(s) 28 and/or ML model(s) 30) trained, e.g., on the first set of reference images, to determine what the region of interest looks like based on what was captured within the image overlay. In some instances, the image overlay for the reference set may need to be adjusted (e.g., by the user or automatically) to capture the site of interest within the frame, such as in a central region of the frame, or at least a threshold amount of the image in the region of the frame corresponding to the image overlay.

Figure 19:
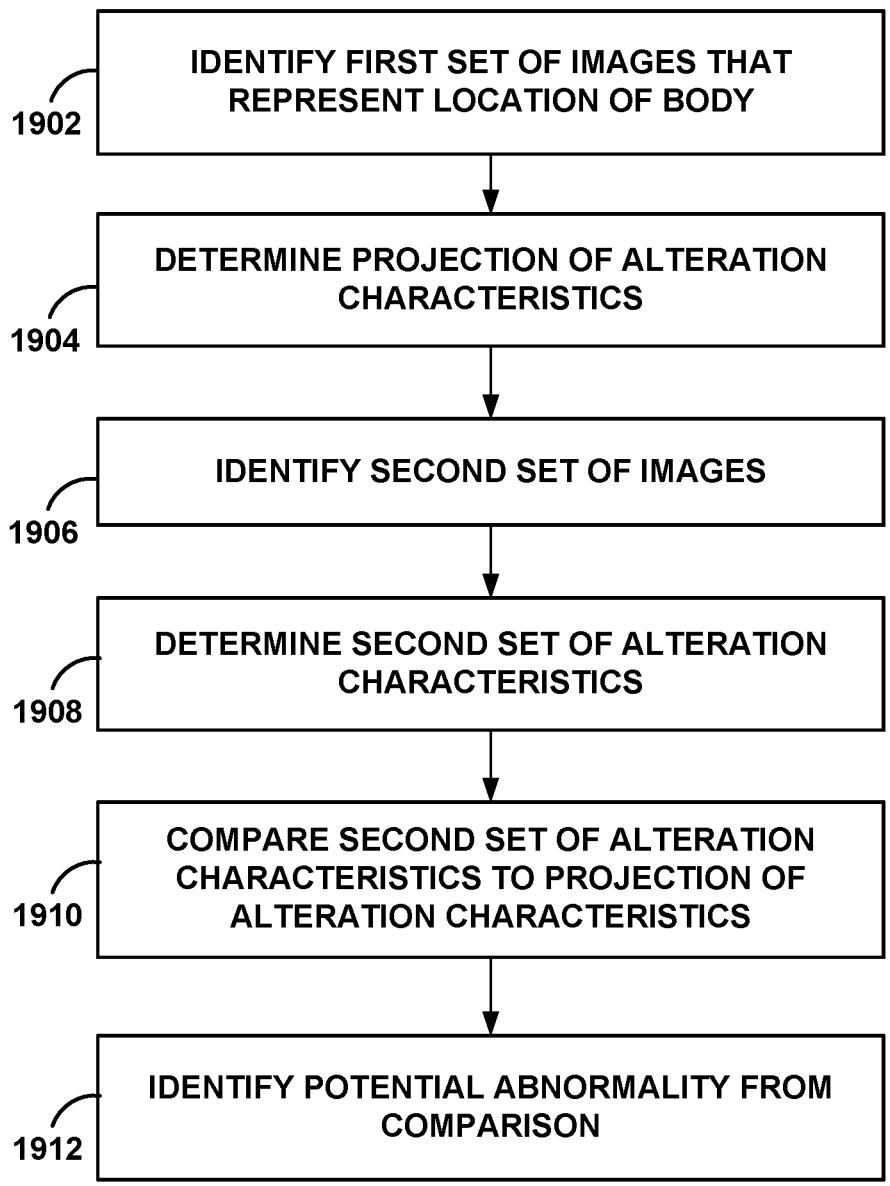
FIG. 19 is a flowchart illustrating an example method of capturing an image of a body over time, in accordance with one or more techniques of this disclosure.

FIG. 19 is a flowchart illustrating an example method of capturing an image of a body, in accordance with one or more techniques of this disclosure. In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may create a personalized baseline for patient 4 and allow AI engine(s) 28 (e.g., inference engines) and/or ML model(s) 30 to provide trend-based analysis. In an example, processing circuitry 20 may deploy AI engine(s) 28 (e.g., inference engines) and/or ML model(s) 30 configured to evaluate images based on historical frames of image data to fit a trend line, rather than evaluating images based on a snapshot (e.g., single still-image) or even based on successive snapshots evaluating against one another rather than being evaluated against baseline characteristics of patient 4. In any case, such an evaluation may inform patient 4 and/or an HCP about how an implantation site (e.g., an explant site) is altering (e.g., progressing) over time towards healing or an abnormality situation (e.g., a rapidly worsening infection or a slowly developing infection). In an example, processing circuitry 20 may enable a preprocessing algorithm to automatically adjust captured images to scale and orientation, so that users reviewing a time lapse of images get a consistent view while reviewing successive images over time. In addition, processing circuitry 20 may enable higher prediction confidence in the image analysis due to the presence of contextual data available at the point of inference, such as with an inference AI engine reviewing images of a particular site-check sub-session, in addition to reviewing other data items of the interactive session, to determine a comprehensive post-implant report.

In some examples, AI engine(s) 28 and/or ML models(s) 30 may be trained on several images that have been labeled as corresponding to an abnormality or not (e.g., infection or not). In such examples, AI engine(s) 28 and/or ML model(s) 30 may be trained with data that has been labeled based on improvement of an implantation site. In an example, AI engine(s) 28 and/or ML model(s) 30 can detect, as an implant status, implantation site "improvement" or implantation site "non-improvement" over time.

In some examples, processing circuitry 20 may acquire images of implantation site from multiple interactive sessions over time. Processing circuitry 20 may maintain a chronology of images to detect improvement or non-improvement of the implantation site. In one example, processing circuitry 20 may collect images on a predetermined schedule and align the images over a period of time post-implant. In such examples, processing circuitry 20 may train AI engine(s) 28 and/or ML model(s) 30 on how much the implantation site characteristics alter over time. In some examples, AI engine(s) 28 and/or ML model(s) 30 may determine a post-implant report based on changes between successive images that identifies differences between the images over time.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may identify a first set of images that represent a particular location of the body of patient 4 (1902). In an example, processing circuitry 20 may identify a first set of images that represent a particular location of the body in which at least one component of IMD 6 coincides (e.g., IMD 6, lead wires, etc.). In some examples, the first set of images may include a single image, while in other examples, the first set of images may include multiple images.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may determine a projection of alteration characteristics, such as healing characteristics (1904). In an example, processing circuitry 20 may determine a trend line or model that represents the projection of alteration characteristics over time. That is, the projection generally represents alteration characteristics of the particular location of the body of patient 4 projected over time. The particular location of the body may include the implantation site of IMD 6 or may include other bodily sites of patient 4 that coincide with other components of IMD 6. In some examples, processing circuitry 20 may determine the projection of alteration characteristics based on images of other IMD recipients, such as recipients that align with a particular cohort of patient 4.

In an illustrative example, processing circuitry 20 may determine the projection of alteration characteristics from the first set of images. In such examples, processing circuitry 20 may determine a common alignment reference for aligning the first set of images in a time-lapse representation of the first set of images. In some examples, processing circuitry 20 may align, according to the common alignment reference, a plurality of images from the first set of images to determine the time-lapse representation. In some examples, processing circuitry 20 may determine, from the plurality of aligned images, the projection of alteration characteristics. In some examples, each image of the first set of images may be validated to determine whether the image should be included in the plurality of images. In one example, processing circuitry 20 may validate images for quality (e.g., blurriness), orientation (e.g., portrait only), and may discard images that fail the validation test.

As described herein, the particular location of the body may, in various examples, include an implantation site of the at least one component of IMD 6. In such examples, the common alignment reference includes an alignment truth that utilizes one or more of: a relative angle of the implantation site, a relative size of the implantation site, to determine and implement the alignment truth to, for example, align the images in a time lapse configuration. In some examples, the common alignment reference may further include: image lighting characteristics, skin pigmentation characteristics, a relative orientation of the implantation site, or a relative location of the implantation site in respective frames of image data representing the first set of images.

In an illustrative example, processing circuitry 20 may align the plurality of images from the first set of images. In an example, processing circuitry 20 may provide, during image capture, an image overlay configured to augment a set of preview frames. Processing circuitry 20 may determine that an image of the particular location of the body from the set of preview frames overlaps with the image overlay. Processing circuitry 20 may obtain, based at least in part on the overlap, a first image of the first set of images, where the first image represents the particular location of the body in accordance with the common alignment reference. Processing circuitry 20 may align, via the plurality of images, images of the implantation site with the common alignment reference. In an example, processing circuitry 20 may automatically capture at least one first image of the first set of images upon detecting that the implantation site aligns with the image overlay. In this way, processing circuitry 20 may obtain a first image that satisfies alignment criteria, such that the at least one first image of the first set of images represents a particular view of the implantation site defined by the image overlay. Subsequent images from the first set of images may then be aligned based on an alignment of the at least one first set of images in order to determine a time-series that captured a plurality of images over time with common features (e.g., zoom, angles, sizes, colors, lighting, brightness, etc.). In some instances, the first set of images may only include a first image captured according to the application of the image overlay to augment the set of preview frames.

In some examples, processing circuitry 20 may determine a set of pre-implant images representing the particular location of the body prior to implantation. In an example, the set of pre-implant images may include images captured prior to an implantation procedure, such that the pre-implant images represent a baseline for patient 4 that, after healing, patient 4 may return to with the, at times inevitable, addition of procedural artifacts (e.g., scarring, etc.). In such examples, a physician or physician's assistant may capture the set of pre-implant images while placing a white balance card (e.g., representing pure white) next to the body of patient 4. In an illustrative and non-limiting example, a nurse or image acquisition representative may, prior to implantation of IMD 6, capture, via camera 32, one or more skin color baseline images of an implantation site (e.g., an anticipated implantation site) of patient 4 while the image acquisition simultaneously or concurrently captures an image of a color reference, such as a white-balance reference card held within the frame.

Processing circuitry 20 may determine the set of pre-implant images with a color reference to allow processing circuitry 20 to identify a color truth for the pigmentation and/or skin type of patient 4. Processing circuitry 20 may store the set of pre-implant images to a storage device (e.g., a cloud storage device or storage device 24), where AI engine(s) 28 and/or ML model(s) 30 may determine a color truth (e.g., via cloud solutions) for patient 4. The color truth may be useful, as described herein, in determining baseline characteristics of patient 4 and for projecting healing characteristics of patient 4 over time based on images captured post-implant. In this way, given the diversity in skin tone and body type around the world, processing circuitry 20 may obtain images of the implantation site prior to and immediately following implantation in order to accurately identify abnormalities (e.g., excessive or abnormal bruising) at the implantation site across various cohorts.

In some examples, the set of pre-implant images comprises a single image or multiple images that represent the particular location of the body of patient 4 captured pursuant to particular lighting conditions or from a particular vantage point relative to a set of potential vantage points representing various different views of the implantation site. In an illustrative example, processing circuitry 20 may determine, from the set of pre-implant images, baseline characteristics of the body of patient 4 prior to the implantation. In some examples, the baseline characteristics may include pigmentation, skin type, etc.

In some examples, AI engine(s) 28 and/or ML model(s) 30 may automatically determine a micro cohort for patient 4 based on the set of pre-implant images, such as a micro cohort based on skin pigmentation. In some examples, a user may, via UI 22, manually self-identify a cohort in which the user self-identifies, such as based on skin type or pigmentation. In another example, processing circuitry 20 may utilize manually entered information and baseline characteristics data to automatically identify a micro cohort for patient 4 that uses the manually-entered information as an assumption input to, for example, AI engine(s) 28 and/or ML model(s) 30 configured to automatically, or at least semi-automatically, identify micro cohorts for further image processing and/or for training purposes as described herein. In some examples, AI engine(s) 28 and/or ML model(s) 30 may automatically infer, from a pre-process at the time of taking a first image of patient 4, a cohort of patient 4 that will align the best results for analyzing images of patient 4.

In an illustrative example, processing circuitry 20 may transmit, via communication circuitry 26, the pre-implant images to a device (e.g., another one of computing device(s) 2) configured to operate a skin color classification algorithm for pre-processing. In another example, processing circuitry 20 may operate skin color classification algorithm, in which case the pre-implant images may only be stored to storage device 24. The algorithm may be trained on thousands of skin photos and uses a color scale, such as Von Luschan's chromatic scale, the Fitzpatrick scale, or combinations thereof. Processing circuitry, e.g., processing circuitry 20 of computing device(s) 2, processing circuitry 64 of edge device(s) 12, processing circuitry 98 of server(s) 94, or processing circuitry 40 of medical device(s) 17, may utilize the color scale in order classify a skin type of patient 4 into various skin type categories so that ML model(s) 28 and/or AI engine(s) 30 may be able to accurately identify abnormalities in the skin following implantation of one of medical device(s) 17 (e.g., IMD 6). The skin type classification may include a classification or organization of the skin type of patient 4 into skin-type subsets, such as various subsets corresponding to particular color scales of the von Luschan scale and/or the Fitzpatrick scale, for example. In any case, processing circuitry 20 patient 4 may automatically segment patient 4 into a micro-cohort, for example, based on the skin-type classification. That is, processing circuitry 20 may automatically determine the cohort for patient 4 based on one or more pre-implant images. in another example, processing circuitry 20 may automatically determine the cohort for patient 4 based on one or more post-implant images (e.g., the first set of images and/or the second set of images).

In such examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may apply, in accordance with each cohort, a particularly defined implantation-site analysis algorithm to yield best results for specific cohorts, such as automatically determined cohorts, by accounting for differences in skin-types. Additionally, during app onboarding, processing circuitry 20 may provide, via UI 22, patient 4 with the option to self-identify their ethnicity, age, weight, biological sex and body-type. As described herein, if provided, processing circuitry 20 may use these inputs to fine-tune results of AI engine(s) 28 and/or ML model(s) 30.

Processing circuitry 20 may determine, based at least in part on the baseline characteristics, the projection of alteration characteristics. In such examples, the alteration characteristics from the projection are configured to approximate, over time, the baseline characteristics of the body of the patient. That is, processing circuitry 20 may determine from a post-implant image a trajectory back toward a baseline of patient 4, such as in terms of returning to a state that includes a sufficiently healed scar at an implantation site of IMD 6.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may identify a second set of images (1906). In an example, processing circuitry 20 may identify the second set of images that represent the particular location of the body at a progression interval that follows in time the first set of images. Similar to the first set of images, the second set of images may include a single image, while in other examples, the second set of images may include multiple images. Likewise, processing circuitry 20 may perform a similar validation for images of the second set of images, and may discard images that fail the validation test. In one example, processing circuitry 20 may determine whether images are captured according to a particular orientation (e.g., portrait, angled, etc.), and may prompt the user, via UI 22, when identifying an image captured at in improper orientation, to capture images according to the particular orientation. In another example, processing circuitry 20 may identify objects, via object recognition, and notify a user, via UI 22, when an image represents an improper object, such as an object that does not appear to represent a relevant implantation site.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may determine a second set of alteration characteristics (1908). In an example, processing circuitry 20 may determine, from the second set of images, the second set of alteration characteristics.

In an illustrative example, processing circuitry 20 may determine the first set of images so as to include at least one first post-implant image and at least one second post-implant image, where those images are captured at successive time intervals. The successive time intervals may be spaced apart in time by a first duration of time. In an example, the duration of time may include a relatively short period of time, such as an hour or a day. In such examples, the second set of images may include at least one third post-implant image captured at a check-in time that comes after a time when the first set of images are captured.

In such examples, the second duration of time may be greater than the first duration of time, such as one week following the last capture of the first set of images. That is, the first set of images may be captured at frequent intervals immediately following the implantation or at least following a time when bandages are removed from the implantation site, such as every hour or every other hour for a first number of days. The first set of images are captured at frequent intervals in order to determine how the characteristics of the images alter over time (e.g., healing indicators). In such examples, the second set of images comprise a successive fourth image captured at a second check-in time that follows a first check-in time by a third duration of time, such as after two or three weeks following when capture of the first image of the baseline set. In such examples, the second set of alteration characteristics comprises a healing trend of relative alteration characteristics between successive images of the second set of images. That is, the second set of alteration characteristics may be based on a healing progression between at least two images of the second set of images, where the healing progression may be compared to the first set of alteration characteristics determined from the first set of images and/or the pre-implant set of images. Processing circuitry 20 may further determine the second set of alteration characteristics based on the pre-implant set of images and/or the first set of images so as to track a trajectory from the first set of images to the second set of images, from the second set of images to a baseline for patient 4 that is based on the pre-implant images, and/or a combination of such trajectories.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may compare the second set of alteration characteristics to the projection of alteration characteristics (1910). In an example, processing circuitry 20 may compare the second set of alteration characteristics to the projection. In an illustrative example, processing circuitry 20 may, to compare the second set of alteration characteristics to the projection, determine a difference amount from the second set of alteration characteristics and the projection. In some examples, processing circuitry 20 may determine a difference amount from the second set of alteration characteristics and the projection by comparing the second set of alteration characteristics to a particular portion of the projection that corresponds to a projected time corresponding to the second set of images (e.g., a time when the second set of images was identified, such as when the second set of images was acquired, captured, received, timestamped, communicated from another device, and/or obtained), where the projected time is projected based at least in part on intervals or points in time that correspond to a historical set of images (e.g., the first set of images, pre-implant images, the first set of images and pre-implant images, etc.).

In a non-limiting example, processing circuitry 20 may determine a projection that indicates that, based on a historical set of images, a particular alteration should occur relative to an implantation site of patient 4 at a particular time in the future (e.g., a projected time). Processing circuitry 20 may, in some instances, prompt patient 4 to capture a second set of images (e.g., one image or a plurality of images) at the projected time and may compare characteristics of the second set of images against the projection to determine to what degree a healing of patient 4 is tracking onto the projection. Where the difference between the projection and the second set of characteristics exceeds a particular threshold, processing circuitry 20 may determine that a closer analysis is warranted or that additional images should be captured of the implantation site for a supplemental or enhanced analysis. In another example, processing circuitry 20 may, rather than prompt patient 4 for images, may identify the second set of images and determine from the projection, a particular portion from the projection that coincides with the second set of images (e.g., coinciding in terms of time intervals). In any case, processing circuitry may compare the second set of images to the projection to determine the presence of an abnormality, such as where the comparison indicates a particular deviation amount that exceeds a predetermined threshold.

In some instances, processing circuitry 20 may determine, from a historical set of images, a projection as to how much the implantation site of patient 4 should be altering over time at a particular time in the future (e.g., a prospective time). In such instances, processing circuitry 20 may compare the second set of alteration characteristics to the projection to identify a potential abnormality, the likelihood of a potential abnormality, or whether further analysis is warranted, such as an analysis by an HCP, technician, etc. In another example, processing circuitry 20 may determine, from the second set of images and in some instances, from the first set of images, how much the implantation site of patient 4 is or appears to be altering over time at a time corresponding to the second set of images. Processing circuitry 20 may determine the second set of alteration characteristics from the determination as to how much the implantation site of patient 4 is or appears to be altering over time, and processing circuitry 20 may compare the second set of alteration characteristics to the prospective projection, where the prospective projection is indicative as to how much processing circuitry 20 expects the implantation site of patient 4 to be altering over time at a particular time from the projection that aligns with, or at least approximates, the time corresponding to one or more images from the second set of images (e.g., the time at which the second set of images were obtained).

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may output, via UI 22, an estimate as to when one or more milestone alterations of the particular location of the body are expected according to the projection. In an example, the milestone estimates may include an indication as to when redness should subside, when soreness should subside below a predefined threshold relative to pain thresholds of patient 4, when likelihood of infection has dropped below a predefined threshold, when implantation site is healed beyond a predefined healing threshold, etc. In addition, processing circuitry 20 may determine the milestone estimates based on a comparison of the second set of alteration characteristics to the projection. The comparison, in such examples, is indicative of a deviation amount that processing circuitry 20 may utilize in order to determine an estimate that is informed by current images of patient 4 and past images of patient 4. In addition, processing circuitry 20 may determine the estimate based on (e.g., as informed by) images and/or healing trends of other IMD patients (e.g., patient of a same micro cohort as patient 4). In any case, the deviation amount may indicate a degree to which a healing of patient 4 has deviated from the projection (e.g., a projection based on historical images of patient 4 and/or other IMD patients) as informed by a determination of the second set of alteration characteristics. As such, processing circuitry 20 may provide an informed estimate as to when patient 4 can expect to reach various alteration milestones of a healing process of patient 4.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may identify the potential abnormality from the comparison (1912). In an example, processing circuitry 20 may identify, based at least in part on the comparison, a potential abnormality at the particular location of the body. In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may identify the potential abnormality by determining an abnormality trend indicating an anticipated progression toward the potential abnormality or toward a worsening abnormality relative to the potential abnormality. In any case, in response to determining the potential abnormality, processing circuitry 20 may transmit (e.g., via communication circuitry 26) the first set of images and the second set of images to a device of one or more HCPs over network 10. In another example, processing circuitry 20 may utilize the abnormality determination to determine a post-implant report that, in some examples, includes a basis in physiological parameter data, device interrogation data, etc.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may identify (e.g., via an inference engine) one or more abnormality control procedures corresponding to the at least one component of the IMD (e.g., gauze, TYRX™, etc.) or corresponding to patient 4 (e.g, medications, etc.). In an example, processing circuitry 20 may determine such information via patient-input during a patient-input subsession. That is, a user (e.g., patient 4) may enter medication information, gauze information, etc., that processing circuitry 20 may reference, via AI inference engine, in order to determine, based at least in part on the one or more abnormality control procedures, the projection data. In such examples, the projection for a healing timeline and the trend towards healing may differ, such as where a TYRX™ control procedure is used or where particular medications are used.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may output a result of the comparison to a storage device (e.g., storage device 24, storage device 65, storage device 96, and/or storage device 50). In an example, processing circuitry 20 may transmit, as part of outputting the second set of images to one or more HCPs, abnormality data items configured to visually represent the potential abnormality identified in the second set of images. In an illustrative example, where processing circuitry 20 labels a result for an image as comprising a 'potential infection,' processing circuitry 20 may generate an alert and provide an alert indication to one or more HCPs (e.g., via UI 22). The alert indication may include a summary of the result, a post-implant report, one or more images, and in some instances, highlighting of the images to indicate characteristics of the potential abnormality. In addition, the alert indication may include a time-lapse of images created in accordance with one or more of the various techniques of this disclosure. In any case, processing circuitry, e.g., processing circuitry 20 of computing device(s) 2, processing circuitry 64 of edge device(s) 12, processing circuitry 98 of data server(s) 94, or processing circuitry 40 of medical device(s) 17 may maintain (e.g., via a respective storage device) a chronology of the first set of images.

In some examples, the projection techniques of this disclosure allow processing circuitry 20 to personalize the algorithm and make feedback most useful to patient 4 and clinician. This is because images of the implantation site may be captured at high frequency immediately following implant, thus, allowing processing circuitry 20 to produce a time-series (e.g., a time lapse) set of data. Processing circuitry 20 may then utilize the time-series to create a personalized baseline for the patient and allow a model to produce trend analysis, as described herein. In another example, processing circuitry 20 may utilize a preprocessing algorithm to auto-adjust all photos to scale and orientation so that physicians reviewing time-series get a consistent view as the HCP reviews historical images, seemingly, through time. In such examples, processing circuitry 20 may provide scheduled reminders prompting the user to capture particular images (e.g., with particular zoom levels, lighting, angles, etc.) at a first frequency in order to determine a first set of reference images (e.g., the first set of post-implant images), and may provide scheduled reminders prompting the user to capture particular images at a second frequency, where the second frequency may include a variable frequency, but in general, may include a frequency that is less than the first frequency, in order to determine the second set of ongoing check-in images (e.g., the second set of post-implant images). Based on at least the two sets of images, processing circuitry 20 may accurately determine the presence of abnormalities and/or determine post-implant reports that indicate abnormalities as informed by other sets of data items (e.g., physiological parameters, etc.) It should be noted that, as described herein, the various techniques of this disclosure (e.g., the projection techniques, the subsession techniques, overlay techniques, etc.) are applicable to both a "cloud" implementation (e.g., Medtronic CareLink® Network) and "edge" implementation (e.g., on the mobile app, tablet app, IoT app, etc.).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may later synchronize, for ease of access and/or algorithm tuning, the data and results of the image analysis. In one example, processing circuitry 20 may coordinate with other processors of the processing system to synchronize data and results of the image analysis between an edge network (e.g., computing device(s) 2, edge device(s) 12, medical device(s) 17, etc.) and a cloud network (e.g., server(s) 94).

Figure 20:
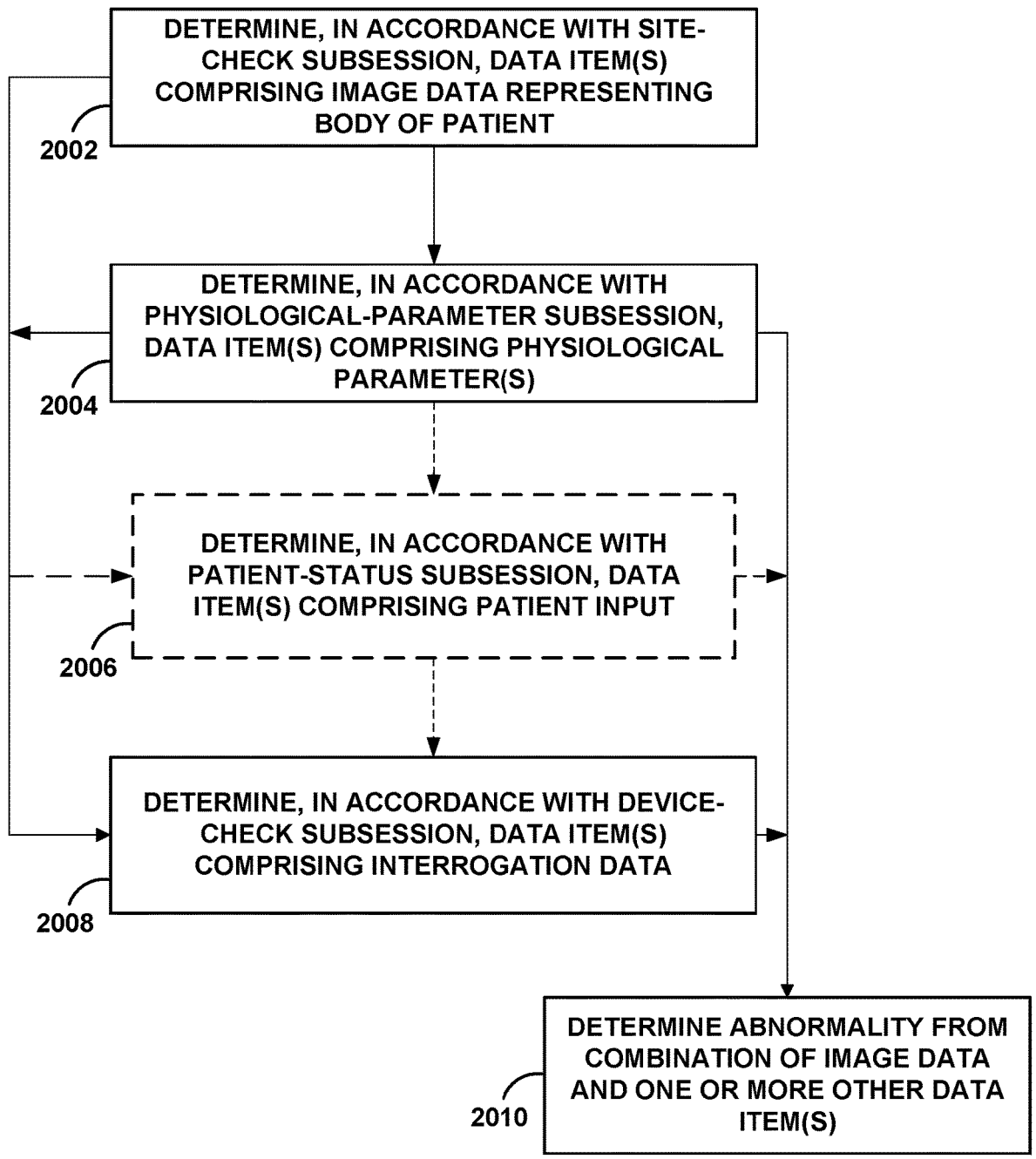
FIG. 20 is a flowchart illustrating an example method of navigating a set of UI interfaces of a virtual check-in process, in accordance with one or more techniques of this disclosure.

FIG. 20 is a flowchart illustrating an example method of navigating a set of UI interfaces of a virtual check-in process (e.g., an interactive session), in accordance with one or more techniques of this disclosure. Processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, in accordance with the site-check subsession, data item(s) comprising image data representing the body of patient 4 (2002). In another examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, in accordance with a physiological-parameter subsession, data item(s) comprising physiological parameters (2004). In an optional example, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, in accordance with a patient-status subsession, data item(s) comprising patient input (2006). As described herein, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, in accordance with a device-check subsession, data item(s) comprising device interrogation data (2008). It should be understood that the subsessions may be performed in various different sequences and with additional subsession or without one or more of the subsession described herein. In any case, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine an abnormality from the combination and/or synthesis of image data and one or more of the other data item(s) described herein (2010).

Figure 21:
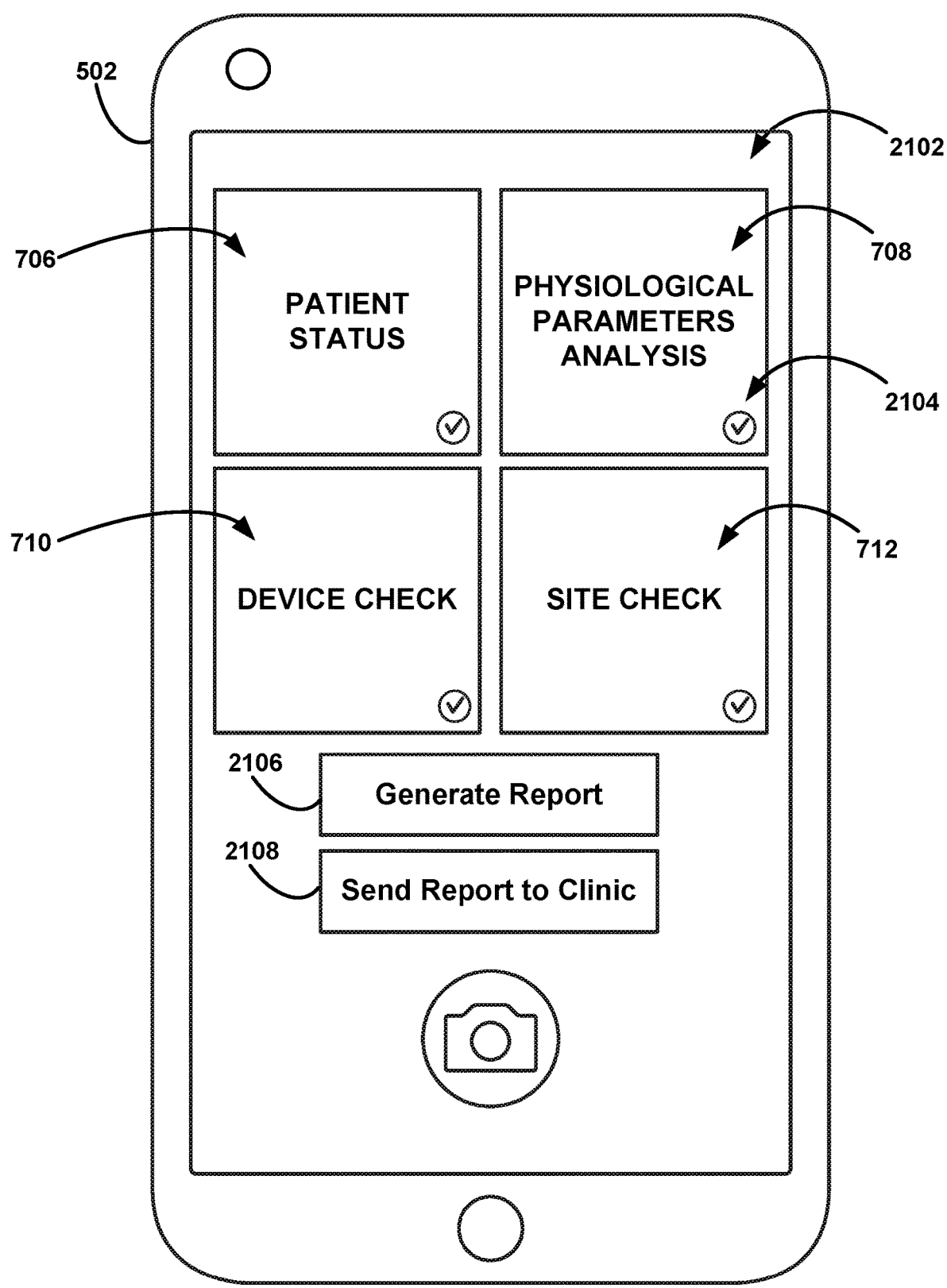
FIG. 21 is a UI visualization of an example complete check-in interface, in accordance with one or more techniques of this disclosure.

FIG. 21 is a UI visualization of an example complete check-in interface 2102, in accordance with one or more techniques of this disclosure. Complete check-in interface 2102 illustrates a UI that processing circuitry 20 may cause to be displayed upon completion of one or more of the virtual check-in subsessions (e.g., device-check subsession, site-check process, etc.). In some instances, processing circuitry 20 may output the complete check-in interface 2102 after the information is submitted that is to be forwarded to the HCP/clinician, etc. FIG. 21 illustrates a UI that computing device(s) 2 may generate and present to indicate completion of the interactive session corresponding to all of the four tiles shown in FIG. 7. As described herein, the complete check-in interface 2102 may relate to lesser or greater number of tiles in some examples, where computing device(s) 2 utilize additional or fewer interfaces to obtain data regarding patient 4 and/or medical device(s) 17. Complete check-in interface 2102 may further include a graphical icon 2104 indicating completion of, for example, the site-check subsession.

In some examples, the image(s) may be adjudicated by a teledermatology service. In such instances, the teledermatology service may be configured to generate a report (e.g., a summary report, post-implant report, etc.) based on the image(s). In addition, computing device(s) 2 may receive the report from the teledermatology service and provide, via UI 22, the report for review. In such examples, computing device(s) 2 may interface with the teledermatology service via network 10 and/or via an intermediary, such as via one of edge device(s) 12. As described herein, edge device(s) 2 may include one of computing device(s) 2, where the computing device 2 is configured to interface with and/or operate the teledermatology service in order to generate, based on the various images, a summary report for output.

In some instances, processing circuitry, e.g., processing circuitry 20 of computing device(s) 2, processing circuitry 64 of edge device(s) 12, processing circuitry 98 of server(s) 94, or processing circuitry 40 of medical device(s) 17, may generate a summary report that matches a proficiency level of a user. In one example, processing circuitry 20 may identify a particular proficiency level of a user and generate a summary report for the user in accordance with the proficiency level. The proficiency level, in this instance, may represent the proficiency of a user in reviewing reports, such as teledermatology reports. Processing circuitry 20 may determine this proficiency level automatically from user data and/or may receive user input indicating this proficiency level, such as by requesting such information from the user via a questionnaire or other input mechanism.

In an illustrative example, processing circuitry 20 may receive a single report data file. Processing circuitry 20 may then transform the data of the data file in order to generate a user-facing summary report (e.g., a post-implant report). Processing circuitry 20 may transform the data differently, for example, when processing circuitry 20 determines the report is being presented to a "novice" user (e.g., an elderly patient taking photos themselves) as compared to being presented to another use, such as an "expert" user (e.g., particular HCPs, nursing home workers, etc.). The summary report may include results of a HCP adjudication of images, physiological parameters, patient-status updates, device interrogation data (e.g., device diagnostics) and/or the results of an automated image analysis of the interactive reporting session.

In some examples, complete check-in interface 2102 may provide an option to schedule an in-person clinic follow-up. Processing circuitry 20 may cause this option to be presented, via UI 22, when a potential abnormality is detected or where processing circuitry 20 was unable to rule out an abnormality from an assessment of the camera images.

In addition, complete check-in interface 2102 may include a "generate report" icon 2106 and/or a "send report to clinic" icon 2108. The report may include, among other information, the image(s) captured by processing circuitry 20. In addition, the report may include a synthesis of data including criteria for failure based on severity of failure (e.g., criteria for finding an abnormality), number of failed tests, number of failed attempts, number of tiles failed, etc. In addition, processing circuitry 20 may generate the report based on a physician preference (e.g., type of report, specifics for data weighting, etc.). Processing circuitry 20 may, in addition, transmit the report based on a physician preference regarding notifications and/or notification frequency. Processing circuitry 20 may further synthesize the data based on characteristics of patient 4 and/or type of medical device 17 (e.g., IMD 6).

In an illustrative example, processing circuitry 20 may employ various abnormality scoring algorithms that are based on a severity of a potential abnormality detected in one or more images. The abnormality scoring algorithm may determine an abnormality score that maps to an actionable response (e.g., transmit report to HCP, automatically schedule clinician visit, etc.). Processing circuitry 20 may determine a sensitivity for an abnormality scoring algorithm, e.g., based on a severity of a potential abnormality detected in an image of a bodily site of patient 4 (e.g., an implantation site), based on IMD type, etc. The sensitivity may define a threshold that can range from a conservative threshold that causes a particular output (e.g., failure determination, transmit report to HCP, etc.) in response to a determination of any image indicating an abnormality or analysis of one or more images against a projection indicating an abnormality. In another example, the sensitivity may define a complex threshold that utilizes a weighted composite score that, in a non-limiting example, factors the severity of the failure across the subsessions, along with the underlying algorithms that define each subsession (whether failed or not), relative to any underlying medical conditions of patient 4, to determine if a failure is determined that warrants a particular response, e.g., based on a mapping of an abnormality score to particular response outputs. In addition, the sensitivity may further define a threshold that factors in physician programmable limits for medical device(s) 17.

In some examples, processing circuitry 20 may provide feedback to patient 4 through graphical simplified icons. In another example, processing circuitry 20 may obtain a preference from a HCP that indicates, rather than simplified icons, to provide complex results. In such instances, processing circuitry 20 may provide feedback to patient 4 as complex results.

Figure 22:
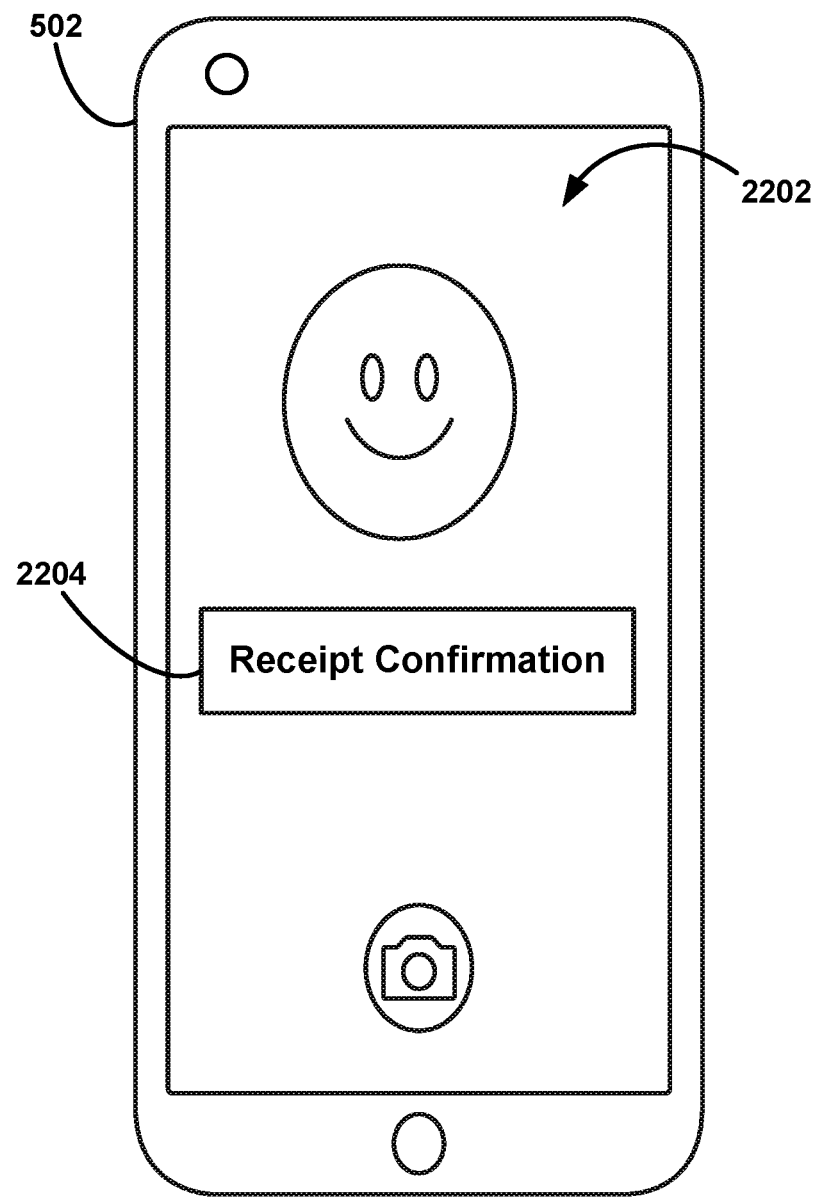
FIG. 22 is a UI visualization of an example complete check-in interface, in accordance with one or more techniques of this disclosure.

FIG. 22 is a UI visualization of an example complete check-in interface 2202, in accordance with one or more techniques of this disclosure. In an example, complete check-in interface 2202 indicates a confirmation of receipt 2204, either by the HCP's office or by an intermediate system that is responsible for submission to the HCP's office. That is, processing circuitry 20 may receive confirmation from an intermediate system (e.g., edge device(s) 12) and in turn, may provide receipt confirmation 2204. Receipt confirmation 2204 may represent receipt of the post-implant report at the office of a HCP of patient 4. In another example, receipt confirmation 2204 may represent confirmation that the post-implant report has been saved successfully to a database (e.g., one of server(s) 94, a plurality of server(s) 94 comprising a cloud storage database, server(s) 94 and edge device(s) 12 comprising a cloud storage database, etc.). In such examples, authorized HCP may, via computing device 2 of the HCP, access the report from the database. In an illustrative example, receipt confirmation may further include uploading the summary report to an EMR database. As described herein, the techniques of this disclosure are applicable to both a "cloud" implementation (e.g., Medtronic CareLink® Network) and/or "edge" implementation (e.g., on a mobile app). As such, the post-implant report may be uploaded and stored in any number of different locations and accessed from those locations in any number of different ways.

Figure 23:
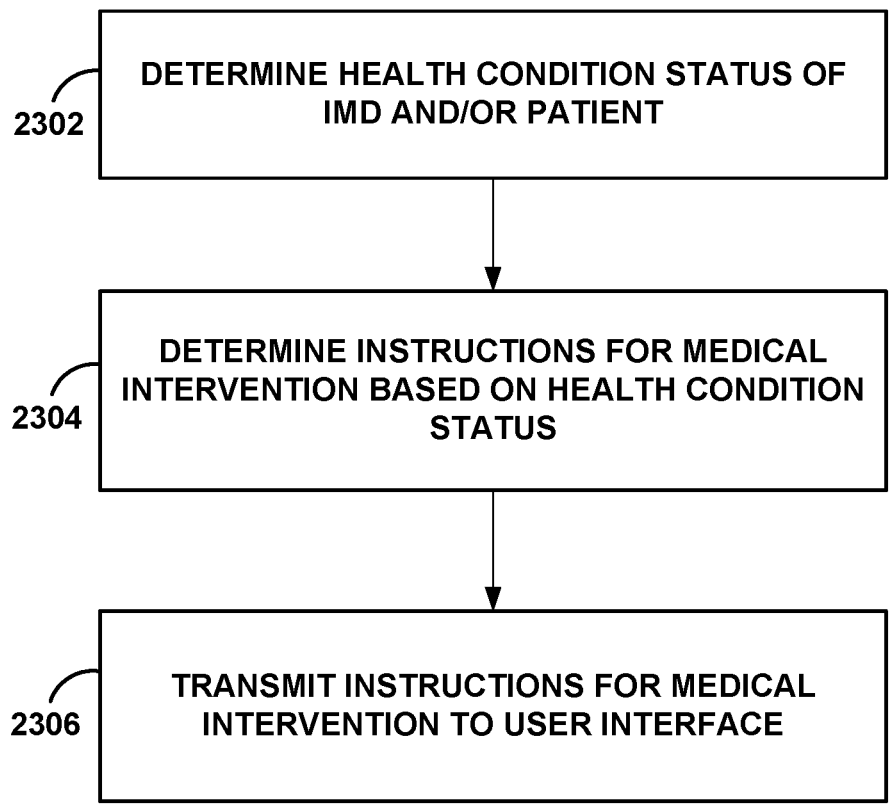
FIG. 23 is a flowchart illustrating an example method of determining instructions for medical intervention concerning an IMD patient, in accordance with one or more techniques of this disclosure.

FIG. 23 is a flowchart illustrating an example method of determining instructions for medical intervention concerning an IMD patient, in accordance with one or more techniques of this disclosure. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine, from a post-implant report, a health condition status of at least one of medical device(s) 17 (e.g., IMD(s) 6) and/or patient 4 (2302). The health condition status may include an indication that processing circuitry 20 has determined an abnormality at the implantation site of IMD 6 and/or an abnormality with the performance of one or more medical device(s) 17 (e.g., IMD 6), an abnormality in a physiological parameter, and/or an abnormality with a patient-status input. In some instances, processing circuitry 20 may determine the health condition status based on a synthesis (e.g., combination) of data items obtained via a plurality of subsessions (e.g., a site-check subsession and a physiological parameter subsession) of an interactive check-in session. In some examples, processing circuitry 20 determines the health condition status based on images received via UI 22. Although described as being generally performed by computing device(s) 2, the example method of FIG. 23 may be performed by, e.g., any one or more of edge device(s) 12, medical device(s) 17, or server(s) 94, e.g., by the processing circuitry of any one or more of these devices.

Processing circuitry, e.g., processing circuitry 20 of computing device(s) 2, processing circuitry 64 of edge device(s) 12, processing circuitry 98 of server(s) 94, or processing circuitry 40 of medical device(s) 17, may determine instructions for medical intervention based on the health condition status of patient 4 (2304). For example, where processing circuitry 20 determines the presence of an abnormality at the implantation site of IMD(s) 6, processing circuitry 20 may determine instructions for medical intervention based on the abnormality. In another example, where processing circuitry 20 determines the presence of an abnormality at the implantation site of IMD(s) 6 and an abnormality in a physiological parameter of patient 4, processing circuitry 20 may determine instructions for medical intervention based on a post-implant report that processing circuitry 20 may generate based at least in part on the multiple abnormalities. In some examples, processing circuitry 20 may determine different instructions for different severity levels or abnormality categories. For example, processing circuitry 20 may determine a first set of instructions for one abnormality that processing circuitry 20 determines is likely less severe than another abnormality. In some examples, processing circuitry 20 may not determine intervention instructions where processing circuitry 20 determines that the abnormality level does not satisfy a predefined threshold. In some examples, processing circuitry 20 may provide an alert, such as a text- or graphicsbased notification, a visual notification, etc. In some examples, processing circuitry 20 may cause an audible alarm to sound or cause a tactile alarm, alerting patient 4 of a determined abnormality. In other examples, computing device(s) 2 may provide a visual light indication, such as emitting a red light for high severity or a yellow light for medium severity. The alert may indicate a potential, possible or predicted abnormality event (e.g., a potential infection).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may transmit the instructions for medical intervention to be display via a user interface, such as UI 22 (2306). In some examples, processing circuitry 20 may transmit the instructions to a device of a HCP (e.g., a caretaker), such as a pager of the HCP. In examples where processing circuitry 64 generates the instructions, processing circuitry 20 may transmit the instructions for medical intervention to a user interface, such as UI 22. The instructions may include the post-implant report and/or individual abnormality indications (e.g., ECG abnormalities, etc.). In some examples, edge device(s) 12, medical device(s) 17 (e.g., IMD 6), server(s) 94, and/or computing device(s) 2 may use the gathered data to predict adverse health events (e.g., worsening infections) using integrated diagnostic methods. That is, computing device(s) 2 may use the abnormality determination, including a likelihood or severity determination, as an evidence node of a probability model deployed, for example, by AI engine(s) 28 and/or ML model(s) 30, in order to determine a probability score indicating the likelihood that an implantation site of patient 4 is infected, is likely to become infected within a predetermined amount of time, that one of medical device(s) 17 (e.g., IMD 6) is likely to experience a functional abnormality (e.g., a malfunction), etc. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may further include, as evidence nodes for a probability determination (e.g., abnormality prediction), criteria for failure based on severity of failure (e.g., criteria for finding an abnormality), number of failed tests, number of failed attempts, number of tiles or subsessions failed, patient characteristics, type of medical device(s) 17 (e.g., IMD 6), physician preferences, etc.

While described from the perspective of a user computing device 2 performing the techniques of this disclosure, it should be noted that the system of this disclosure supports bidirectional communication between a user (e.g., patient 4) and an HCP. The bidirectional communication may function using similar UIs on both ends of the communication line. In such examples, an HCP may, via computing device 2 of the HCP, access images uploaded by the user via computing device 2 of the user, physiological parameter data items, medical device information, patient information, etc. In addition, the HCP may, via computing device 2 of the HCP, determine the presence or absence of an abnormality from the data upload, and transmit a summary report back to computing device 2 of the user (e.g., patient 4), for example, including one or more indications of an abnormality.

Illustrative examples of the disclosure include:

Example 1: A method of monitoring a patient of an IMD, the method comprising: providing, via a computing device, an interactive session configured to allow a user to navigate a plurality of subsessions comprising at least a first subsession and a second subsession distinct from the first subsession, wherein the first subsession comprises capturing image data via one or more cameras; determining, via the computing device, a first set of data items in accordance with the first subsession of the interactive session, the first set of data items including the image data; determining, via the computing device, a second set of data items in accordance with the second subsession of the interactive session, the second set of data items distinct from the first set of data items and comprising one or more of: data obtained from the IMD, at least one physiological parameter of the patient, or user-input data; determining, based at least in part on the first set of data items and the second set of data items, an abnormality corresponding to at least one of the patient or the IMD; and outputting, via the computing device, a post-implant report of the interactive session, wherein the post-implant report includes indication of the abnormality and indication of an amount of time that has transpired since the date of implantation of the IMD.

Example 2: A method according to Example 1, wherein the first subsession comprises determining an alteration projection of a bodily site over time from a set of images; and determining an abnormality based at least in part on a comparison of the image data and the alteration projection.

Example 3: A method according to any of Examples 1 or 2, wherein providing the interactive session comprises: training, via the computing device, a session generator on one or more of: cohort parameters or IMD information; deploying, via the computing device, the session generator to generate the interactive session; and providing, via the session generator, the interactive session that, as a result of the training, is at least in part personalized for the user.

Example 4: A method according to any of Examples 1 through 3, wherein the IMD information includes interrogation data, and wherein the method further comprises: performing, via the computing device, a pairing process, the pairing process configured to pair the computing device with the IMD; and receiving, via the pairing process, the interrogation data regarding the IMD; and storing, via the computing device, the interrogation data as historical interrogation data for reference.

Example 5: A method according to any of Examples 1 through 4, wherein providing the interactive session comprises: identifying a follow-up schedule for the patient, the follow-up schedule defined by one or more time periods in which the computing device is configured to prompt the user to conduct the interactive session; and providing the interactive session in accordance with the follow-up schedule.

Example 6: A method according to Example 5, wherein identifying the follow-up schedule comprises: receiving, via communication circuitry of the computing device, a push notification; and determining, based on the push notification, a first time period for the follow-up schedule.

Example 7: A method according to any of Examples 5 or 6, the one or more time periods include at least one time period that corresponds to a predetermined amount of time from a date of implantation of the IMD.

Example 8: A method according to any of Examples 1 through 7, wherein the image data comprises one or more frames that represent images of a body of the patient.

Example 9: A method according to Example 8, wherein a portion of the body of the patient comprises an implantation site of the IMD, and wherein the one or more frames represent images of the implantation site.

Example 10: A method according to any of Examples 1 through 9, wherein providing the interactive session comprises: providing a top-level interface that includes a first interface tile, wherein the first interface tile corresponds to the first subsession, and wherein the first subsession comprises a first subinterface level that is at a lower level relative to a level of the top-level interface.

Example 11: A method according to Example 10, wherein the first set of data items comprises an image overlay, and wherein the method further comprises: outputting, via the computing device, the image overlay at the first subinterface level.

Example 12: A method according to any of Examples 10 or 11, wherein providing the first subsession comprises: detecting, via the computing device, selection of the first interface tile; and providing, via the computing device, the first subsession of the interactive session.

Example 13: A method according to Example 12, wherein determining the first set of data items comprises: providing, via the computing device, a prompt for the user to utilize the one or more cameras to capture the image data; and determining, subsequent to the prompt, at least a portion of the first set of data items.

Example 14: A method according to any of Examples 10 through 13, wherein providing the second subsession comprises: detecting, via the computing device, selection of a second interface tile, wherein the first interface tile and the second interface tile are distinct from one another; and providing, in response to selection of the second interface tile, the second subsession of the interactive session.

Example 15: A method according to Example 14, wherein the top-level interface includes the second interface tile.

Example 16: A method according to any of Examples 14 or 15, further comprising: providing, via a second subsession interface, the second subsession of the interactive session; modifying the second interface tile to indicate completion of the second subsession; providing, subsequent to the second subsession, the first subsession of the interactive session; modifying the first interface tile to indicate completion of the first subsession; providing, subsequent to the first subsession or the second subsession, a third subsession of the interactive session; and determining, via the computing device, a third set of data items in accordance with the third subsession of the interactive session, the third set of data items distinct from the first set of data items.

Example 17: A method according to Example 16, wherein determining the third set of data items comprises: receiving physiological parameter signals; and determining, from the physiological parameter signals, the third set of data items.

Example 18: A method according to any of Examples 1 through 17, wherein the abnormality comprises a first abnormality, and wherein determining the post-implant report comprises: outputting, via communication circuitry of the computing device, the second set of data items to another device; receiving, via communication circuitry of the computing device, a result of an analysis of the third set of data items, the result indicating that the second set of data items does not indicate the presence of a second abnormality; and determining the post-implant report based at least in part on the first abnormality and the second set of data items.

Example 19: A method according to any of Examples 1 through 15, wherein the second subsession comprises a physiological-parameter subsession, wherein determining the second set of data items comprises: receiving, in accordance with the second subsession, at least one physiological parameter corresponding to the patient; and determining, from the at least one physiological parameter, the second set of data items.

Example 20: A method according to Example 19, wherein receiving the at least one physiological parameter comprises: receiving, via communication circuitry of the computing device, the at least one physiological parameter from a plurality of medical devices.

Example 21: A method according to any of Examples 19 or 20, wherein the at least one physiological parameter comprises at least one of: an electrocardiogram (ECG) parameter, a respiration parameter, an impedance parameter, an activity parameter, or a pressure parameter.

Example 22: A method according to Example 21, wherein the ECG parameter represents an abnormal ECG, and wherein determining an abnormality comprises:
determining, based at least in part on the abnormal ECG, the abnormality.

Example 23: A method according to any of Examples 1 through 15, wherein the second subsession comprises a device-check subsession, wherein determining the second set of data items comprises: performing, via communication circuitry of the computing device, an interrogation of one or more medical devices corresponding to the patient, wherein the one or more medical devices include the IMD; and determining, from the interrogation, the second set of data items.

Example 24: A method according to any of Example 23, wherein performing the interrogation comprises: receiving, via a computing network, the second set of data items.

Example 25: A method according to any of Examples 23 or 24, wherein determining the post-implant report comprises: determining, from the second set of data items, that the one or more medical devices satisfy one or more performance thresholds; and determining, based at least in part on the second set of data items, the post-implant report.

Example 26: A method according to any of Examples 1 through 3, wherein the second subsession comprises a patient-status subsession, wherein determining the second set of data items comprises: receiving user-input data in accordance with the second subsession of the interactive session; and determining, from the user-input data, the second set of data items.

Example 27: A method according to Example 26, wherein the user-input data comprises one or more of: patient-entered data, medication information, symptom information, physiological metrics, or anatomical metrics.

Example 28: A method according to any of Examples 26 or 27, wherein the interactive session comprises a third subsession and a fourth subsession, wherein the third subsession comprises a physiological-parameter subsession and the fourth subsession comprises a device-check subsession, wherein determining the abnormality comprises: determining, in accordance with the third subsession, a third set of data items, the third set of data items comprising the at least one physiological parameter of the patient; determining, in accordance with the fourth subsession, a fourth set of data items, the fourth set of data items comprising interrogation data; and determining the abnormality based at least in part on the third set of data items or the fourth set of data items.

Example 29: A method according to any of Examples 1 through 28, wherein providing the second subsession comprises: initiating, by the computing device, the second subsession subsequent to the first subsession.

Example 30: A method according to any of Examples 1 through 29, wherein determining the first set of data items comprises: receiving, via communication circuitry of the computing device, the first set of data items, and wherein determining the second set of data items comprises: receiving, via the computing device, the second set of data items.

Example 31: A method according to any of Examples 1 through 15, wherein the second set of data items comprises information indicative of: an abnormality of the at least one physiological parameter of the patient or an abnormality of a device parameter corresponding to one or more medical devices.

Example 32: A method according to any of Examples 1 through 31, wherein determining indication of the abnormality comprises: outputting, to an abnormality determiner for an abnormality analysis, at least one of the first set of data items or the second set of data items; and determining, by the computing device, a result of the abnormality analysis, wherein the result indicates the abnormality.

Example 33: A method according to Example 32, wherein the abnormality determiner includes at least one of an AI engine or a ML model.

Example 34: A method according to any of Examples 32 or 33, wherein the computing device includes the abnormality determiner, and wherein determining the abnormality comprises: deploying, by the computing device, the abnormality determiner to determine the abnormality, wherein the abnormality determiner is trained to identify, based at least in part on the image data, the abnormality.

Example 35: A method according to any of Examples 1 through 23, wherein outputting the post-implant report comprises: outputting, by the computing device, the post-implant report to a device of a HCP via a computing network.

Example 36: A method according to any of Examples 1 through 35, wherein the user is the patient.

Example 37: A method according to any of Examples 1 through 36, determining, by the computing device, that the interactive session is complete; and providing a notification, via the computing device, that the interactive session is complete.

Example 38: A method according to any of Examples 1 through 37, wherein outputting the post-implant report comprises: outputting, by the computing device, a result of the post-implant report for display.

Example 39: A system for monitoring a patient of an IMD, the system comprising one or more means for performing the methods of any of Examples 1 through 38. For example, the system of Example 39 may include a memory configured to store image data; and one or more processors implemented in circuitry and configured to: provide an interactive session configured to allow a user to navigate a plurality of subsessions comprising at least a first subsession and a second subsession distinct from the first subsession, wherein the first subsession comprises capturing the image data via one or more cameras; determine a first set of data items in accordance with the first subsession of the interactive session, the first set of data items including the image data; determine a second set of data items in accordance with the second subsession of the interactive session, the second set of data items distinct from the first set of data items and comprising one or more of: data obtained from the IMD, at least one physiological parameter of the patient, or user-input data; determine, based at least in part on the first set of data items and the second set of data items, an abnormality corresponding to at least one of the patient or the IMD; and output a post-implant report of the interactive session, wherein the post-implant report includes indication of the abnormality and indication of an amount of time that has transpired since the date of implantation of the IMD.

Example 40: A system according to Example 39, wherein to determine the post-implant report, the one or more processors are configured to: determine, from the second set of data items, the abnormality; and determine, based at least in part on the abnormality and the first set of data items, the post-implant report.

Example 41: A system according to any of Examples 39 or 40, wherein to provide the interactive session, the one or more processors are configured to: train a session generator on one or more of: cohort parameters or IMD information; deploy the session generator to generate the interactive session; and provide the interactive session that, as a result of the training, is at least in part personalized for the user.

Example 42: A system according to any of Example 41, wherein the IMD information includes interrogation data, and wherein the one or more processors are further configured to: perform a pairing process, the pairing process configured to pair a mobile device with the IMD; and receive, via the pairing process, the interrogation data regarding the IMD; and store the interrogation data as historical interrogation data for reference.

Example 43: A system according to any of Examples 39 through 42, wherein to provide the interactive session, the one or more processors are configured to: identify a follow-up schedule for the patient, the follow-up schedule defined by one or more time periods in which the computing device is configured to prompt the user to conduct the interactive session; and provide the interactive session in accordance with the follow-up schedule.

Example 44: A system according to Example 43, wherein to identify the follow-up schedule, the one or more processors are configured to: receive, via communication circuitry, a push notification; and determine, based on the push notification, a first time period for the follow-up schedule.

Example 45: A system according to any of Examples 43 or 44, wherein the one or more time periods include at least one time period that corresponds to a predetermined amount of time from the date of implantation of the IMD.

Example 46: A system according to any of Examples 39 through 45, wherein the image data comprises one or more frames that represent images of a body of the patient.

Example 47: A system according to Example 46, wherein a portion of the body of the patient comprises an implantation site of the IMD, and wherein the one or more frames represent images of the implantation site.

Example 48: A system according to any of Examples 39 through 47, wherein to provide the interactive session, the one or more processors are configured to: provide a top-level interface that includes a first interface tile, wherein the first interface tile corresponds to the first subsession, and wherein the first subsession comprises a first subinterface level that is at a lower level relative to a level of the top-level interface.

Example 49: A system according to Example 48, wherein the first set of data items comprises an image overlay, and wherein the one or more processors are further configured to: output the image overlay at the first subinterface level.

Example 50: A system according to Example 49, wherein the image overlay comprises a static image overlay retrieved from an overlay library comprising the at least one image overlay.

Example 51: A system according to any of Examples 49 or 50, wherein the one or more processors are further configured to: determine, based at least in part on patient data, IMD information, and/or a template overlay, a custom image overlay as the image overlay.

Example 52: A system according to any of Examples 48 through 51, wherein to provide the first subsession, the one or more processors are configured to: detect selection of the first interface tile; and provide the first subsession of the interactive session.

Example 53: A system according to any of Examples 39 through 52, wherein to determine the first set of data items, the one or more processors are configured to: provide, via a user interface (UI), a prompt for the user to utilize the one or more cameras to capture the image data; and determining, subsequent to the prompt, at least a portion of the first set of data items.

Example 54: A system according to any of Examples 48 through 53, wherein to provide the second subsession, the one or more processors are configured to: detect selection of a second interface tile, wherein the first interface tile and the second interface tile are distinct from one another; and provide, in response to selection of the second interface tile, the second subsession of the interactive session.

Example 55: A system according to Example 54, wherein the top-level interface includes the second interface tile.

Example 56: A system according to any of Examples 54 or 55, wherein the one or more processors are further configured to: provide, via a second subsession interface, the second subsession of the interactive session; modify the second interface tile to indicate completion of the second subsession; provide, subsequent to the second subsession, the first subsession of the interactive session; modify the first interface tile to indicate completion of the first subsession; provide, subsequent to the first subsession or the second subsession, a third subsession of the interactive session; and determine a third set of data items in accordance with the third subsession of the interactive session, the third set of data items distinct from the first set of data items.

Example 57: A system according to Example 56, wherein to determine the third set of data items, the one or more processors are configured to: receive physiological parameter signals; and determine, from the physiological parameter signals, the third set of data items.

Example 58: A system according to any of Examples 39 through 57, wherein the abnormality comprises a first abnormality, and wherein to determining the post-implant report, the one or more processors are configured to: output the second set of data items to another device; receive a result of an analysis of the third set of data items, the result indicating that the second set of data items does not indicate the presence of a second abnormality; and determine the post-implant report based at least in part on the first abnormality and the second set of data items.

Example 59: A system according to any of Examples 39 through 55, wherein the second subsession comprises a physiological-parameter subsession, wherein to determine the second set of data items, the one or more processors are configured to: receive, in accordance with the second subsession, at least one physiological parameter corresponding to the patient; and determine, from the at least one physiological parameter, the second set of data items.

Example 60: A system according to Example 59, wherein to receive the at least one physiological parameter, the one or more processors are configured to: receive the at least one physiological parameter from a plurality of medical devices.

Example 61: A system according to any of Examples 59 or 60, wherein the at least one physiological parameter comprises at least one of: an ECG parameter, a respiration parameter, an impedance parameter, an activity parameter, or a pressure parameter.

Example 62: A system according to Example 61, wherein the ECG parameter represents an abnormal ECG, and wherein to determine an abnormality, the one or more processors are configured to: determine, based at least in part on the abnormal ECG, the abnormality.

Example 63: A system according to any of Examples 39 through 55, wherein the second subsession comprises a device-check subsession, wherein to determine the second set of data items, the one or more processors are configured to: perform an interrogation of one or more medical devices corresponding to the patient, wherein the one or more medical devices include the IMD; and determine the second set of data items.

Example 64: A system according to Example 63, wherein to perform the interrogation, the one or more processors are configured to: receive, via a computing network, the second set of data items.

Example 65: A system according to any of Examples 63 or 64, wherein to determine the post-implant report, the one or more processors are configured to: determine, from the second set of data items, that the one or more medical devices satisfy one or more performance thresholds; and determine, based at least in part on the second set of data items, the post-implant report.

Example 66: A system according to any of Examples 39 through 55, wherein the second subsession comprises a patient-status subsession, wherein to determine the second set of data items, the one or more processors are configured to: receiving user-input data in accordance with the second subsession of the interactive session; and determining, from the user-input data, the second set of data items.

Example 67: A system according to Example 66, wherein the user-input data comprises one or more of: patient-entered data, medication information, symptom information, physiological metrics, or anatomical metrics.

Example 68: A system according to any of Examples 66 or 67, wherein the interactive session comprises a third subsession and a fourth subsession, wherein the third subsession comprises a physiological-parameter subsession and the fourth subsession comprises a device-check subsession, wherein to determine the abnormality, the one or more processors are configured to: determine, in accordance with the third subsession, a third set of data items, the third set of data items comprising the at least one physiological parameter of the patient; determine, in accordance with the fourth subsession, a fourth set of data items, the fourth set of data items comprising interrogation data; and determine the abnormality based at least in part on the third set of data items or the fourth set of data items.

Example 69: A system according to any of Examples 39 through 68, wherein to provide the second subsession, the one or more processors are configured to: initiate the second subsession subsequent to the first subsession.

Example 70: A system according to Example 69, wherein to determine the first set of data items, the one or more processors are configured to: receive, via communication circuitry of the computing device, the first set of data items, and wherein to determine the second set of data items, the one or more processors are configured to: receive, via a UI of the computing device, the second set of data items.

Example 71: A system according to any of Examples 39 through 70, wherein the second set of data items comprises information indicative of: an abnormality of the at least one physiological parameter of the patient or an abnormality of a device parameter corresponding to one or more medical devices.

Example 72: A system according to any of Examples 39 through 71, wherein to determine indication of the abnormality, the one or more processors are configured to: output, to an abnormality determiner for an abnormality analysis, at least one of the first set of data items or the second set of data items; and determine a result of the abnormality analysis, wherein the result indicates the abnormality.

Example 73: A system according to Example 72, wherein the abnormality determiner includes at least one of an AI engine or a ML model.

Example 74: A system according to any of Examples 72 or 73, wherein to determine the abnormality, the one or more processors are configured to: deploy the abnormality determiner to determine the abnormality, wherein the abnormality determiner is trained to identify, based at least in part on the image data, the abnormality.

Example 75: A system according to any of Examples 39 through 74, wherein to output the post-implant report, the one or more processors are configured to: output the post-implant report to a device of one or more HCPs via a computing network.

Example 76: A system according to any of Examples 39 through 75, wherein the user is the patient.

Example 77: A system according to any of Examples 39 through 76, wherein the one or more processors are configured to: determine that the interactive session is complete; and provide a notification that the interactive session is complete.

Example 78: A system according to Example 77, wherein to output the post-implant report, the one or more processors are configured to: output a result of the post-implant report for display.

Example 79: A system according to any of Examples 39 through 78, wherein the system comprises a computing device, wherein the computing device comprises at least one of the processors and at least one of the cameras, wherein the at least one processor is configured to: determine, based at least in part on the first set of data items and the second set of data items, the abnormality.

In some implementations, the above-described Examples 1-38 and/or 39-79 can be implemented using an apparatus comprising one or more means for performing some or all of the various operations. As an Example 78, an apparatus for monitoring a patient of an IMD includes: means for providing an interactive session to a user, the interactive session configured to allow the user to navigate a plurality of subsessions comprising at least a first subsession and a second subsession distinct from the first subsession, wherein the first subsession comprises capturing image data via one or more cameras; means for determining a first set of data items in accordance with the first subsession of the interactive session, the first set of data items including the image data; means for determining a second set of data items in accordance with the second subsession of the interactive session, the second set of data items distinct from the first set of data items and comprising one or more of: data obtained from an IMD, at least one physiological parameter of a patient, or user-input data; means for determining, based at least in part on the first set of data items and the second set of data items, an abnormality corresponding to at least one of the patient or the IMD; and means for outputting a post-implant report of the interactive session, wherein the post-implant report includes indication of the abnormality and/or indication of an amount of time that has transpired since the date of implantation of the IMD.

In some implementations, the above-described Examples 1-38 and/or 39-79 can be implemented using a computer-readable storage medium storing instructions that when executed cause one or more processors of a device to perform some or all of the various operations. As an Example 79, a computer-readable storage medium can be provided storing instructions that, when executed, cause one or more processors of a system or device for monitoring a patient of an IMD to: provide an interactive session to a user, the interactive session configured to allow the user to navigate a plurality of subsessions comprising at least a first subsession and a second subsession distinct from the first subsession, wherein the first subsession comprises capturing image data via one or more cameras; determine a first set of data items in accordance with the first subsession of the interactive session, the first set of data items including the image data; determine a second set of data items in accordance with the second subsession of the interactive session, the second set of data items distinct from the first set of data items and comprising one or more of: data obtained from an IMD, at least one physiological parameter of a patient, or user-input data; determine, based at least in part on the first set of data items and the second set of data items, an abnormality corresponding to at least one of the patient or the IMD; and output a post-implant report of the interactive session, wherein the post-implant report includes indication of the abnormality and/or indication of an amount of time that has transpired since the date of implantation of the IMD.

Example 80: A method comprising: obtaining, by processing circuitry of a computing device, image data associated with a patient body; and determining, by the computing device based on the obtained image data, a present status of an implant-related wound on the patient body.

Example 81: A method according to Example 80, further comprising prompting a mobile device user to capture the image data using the mobile device a predetermined time after an implantation resulting in the implant-related wound.

Example 82: A method according to any of Examples 80 or 81, obtaining, by processing circuitry of a mobile device, data associated with functioning of a medical device implanted within a patient body; and determining, based on the captured image data, performance metrics of the medical device based on the obtained data.

Various examples have been described. However, one skilled in the art will appreciate that various modifications may be made to the described examples without departing from the scope of the claims. For example, although described primarily with reference to ECG parameters, in some examples, other physiological parameters (e.g., impedance) or device parameters (e.g., temperature sensor data) may be used as evidence of a potential abnormality (e.g., device migration), where such evidence may be used in conjunction with the image data to accurately determine the presence of the potential abnormality, such as within a degree of certainty or at a particular confidence interval (e.g., greater than X % confidence, greater than 95% confidence, etc.).

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

Based upon the above discussion and illustrations, it is recognized that various modifications and changes may be made to the disclosed technology in a manner that does not necessarily require strict adherence to the examples and applications illustrated and described herein. Such modifications do not depart from the true spirit and scope of various aspects of the disclosure, including aspects set forth in the claims.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Combinations of the above should also be included within the scope of computer-readable media.

Instructions may be executed by one or more processors, such as one or more DSPs, general purpose microprocessors, ASICs, FPGAs, CPLDs, or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Any of the above-mentioned "processors," and/or devices incorporating any of the above-mentioned processors or processing circuitry, may, in some instances, be referred to herein as, for example, "computers," "computer devices," "computing devices," "hardware computing devices," "hardware processors," "processing units," "processing circuitry," etc. Computing devices of the above examples may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In some examples, the computing devices may be controlled by a proprietary operating system. Conventional operating systems control and schedule computer processes for execution, perform memory management, provide file system, networking, I/O services, and provide UI functionality, such as GUI functionality, among other things.

The techniques of this disclosure may be implemented in a wide variety of devices or apparatuses, including an integrated circuit (IC) or a set of ICs (e.g., a chip set). Various components, modules, or units are described in this disclosure to emphasize functional aspects of devices configured to perform the disclosed techniques, but do not necessarily require realization by different hardware units.

Various examples have been described. These and other examples are within the scope of the following claims.

What is claimed is:

1. A method of imaging a body of a patient of an implantable medical device (IMD), the method comprising:
   identifying, via processing circuitry of a computing device, a first set of images that represent a particular location of the body in which at least one component of the IMD coincides
   determining, from the first set of images, a projection of alteration characteristics of the particular location of the body projected over time, wherein the projection of alteration characteristics includes a projection of healing over time to a future time to indicate that a particular alteration should occur at the future time;
   identifying, via the processing circuitry, a second set of images that represent the particular location of the body at a progression interval that follows in time the first set of images;
   determining, from the second set of images, a second set of alteration characteristics;
   comparing, via the processing circuitry, the second set of alteration characteristics to the projection; and
   identifying, based at least in part on the comparison, a potential abnormality at the particular location of the body,
   wherein determining the projection comprises:
      determining a common alignment reference for aligning the first set of images in a time-lapse representation of the first set of images;
      aligning, according to the common alignment reference, a plurality of images from the first set of images to determine the time-lapse representation; and
      determining, from the plurality of aligned images, the projection of alteration characteristics.

2. The method of claim 1, wherein the particular location of the body includes an implantation site of the at least one component of the IMD, and wherein the common alignment reference comprises one or more of: a relative angle of the implantation site, a relative size of the implantation site, image lighting characteristics, skin pigmentation characteristics, a relative orientation of the implantation site, or a relative location of the implantation site in respective frames of image data representing the first set of images.

3. The method of claim 1, wherein the particular location of the body includes an implantation site of the at least one component of the IMD, and wherein aligning the plurality of images comprises:
   providing, via the processing circuitry, an image overlay configured to augment a set of preview frames of image data;
   determining, via the processing circuitry, that an image of the particular location of the body from the set of preview frames overlaps with the image overlay;
   obtaining, based at least in part on the overlap, a first image of the first set of images, wherein the first image represents the particular location of the body in accordance with the common alignment reference; and
   aligning, via the plurality of images, images of the implantation site with the common alignment reference.

4. The method of claim 1, wherein determining the projection comprises:
   determining, via the processing circuitry of the computing device, a set of pre-implant images representing the particular location of the body prior to implantation;
   determining, from the set of pre-implant images, baseline characteristics of the body of the patient prior to the implantation; and
   determining, based at least in part on the baseline characteristics, the projection of alteration characteristics.

5. The method of claim 4, wherein the alteration characteristics from the projection are configured to approximate, over time, the baseline characteristics of the body of the patient.

6. The method of claim 5, wherein the particular location of the body includes an implantation site of the at least one component of the IMD, and wherein the set of pre-implant images comprises a single image representing the particular location of the body captured pursuant to particular lighting conditions or from a particular vantage point relative to a set of potential vantage points representing various different views of the implantation site.

7. The method of claim 1,
   wherein the first set of images comprise at least a first image and a second image captured at successive time intervals, wherein the successive time intervals are spaced apart in time by a first duration of time, and
   wherein the second set of images comprises a third image captured at a check-in time that follows in time a first interval of the successive time intervals by a second duration of time, wherein the second duration of time is greater than the first duration of time.

8. The method of claim 7, wherein the check-in time comprises a first check-in time, and wherein the second set of images comprises a successive fourth image captured at a second check-in time that follows the first check-in time by a third duration of time, wherein the third duration of time is greater than the first duration of time, and
   wherein the second set of alteration characteristics comprises a healing trend of relative alteration characteristics between successive images of the second set of images.

9. The method of claim 1, further comprising:
   outputting, via a user interface of the computing device, an estimate as to when one or more milestone alterations of the particular location of the body are expected according to the projection.

10. The method of claim 1, wherein determining the projection comprises:
    identifying, via an inference engine, one or more abnormality control procedures corresponding to the at least one component of the IMD or the patient; and
    determining, based at least in part on the one or more abnormality control procedures, the projection.

11. The method of claim 1, wherein identifying the potential abnormality comprises:
    determining an abnormality trend indicating an anticipated progression toward the potential abnormality or toward a worsening abnormality relative to the potential abnormality.

12. The method of claim 1, further comprising:
    in response to determining the potential abnormality, transmitting, via communication circuitry of the computing device, the first set of images and the second set of images to a device of one or more health care professionals (HCPs) over a computing network.

13. The method of claim 12, further comprising:
    outputting, via the processing circuitry of the computing device, a result of the comparison to a storage device of the computing device; and
    transmitting, as part of transmitting the second set of images, abnormality data items configured to visually represent the potential abnormality identified in the second set of images.

14. The method of claim 12, further comprising:
    maintaining, via a storage device of the computing device, a chronology of the first set of images.

15. A system for imaging a body of a patient of an implantable medical device (IMD), the system comprising:
    a memory configured to store one or more frames of image data, the one or more frames representing at least a first set of images; and
    one or more processors in communication with the memory, the one or more processors configured to:
       identify the first set of images that represent a particular location of the body in which at least one component of the IMD coincides;
       determine, from the first set of images, a projection of alteration characteristics of the particular location of the body projected over time, wherein the projection of alteration characteristics includes a projection of healing over time to a future time to indicate that a particular alteration should occur at the future time;
       identify a second set of images that represent the particular location of the body at a progression interval relative to the first set of images;
       determine, from the second set of images, a second set of alteration characteristics;
       compare the second set of alteration characteristics to the projection; and
       identify, based at least in part on the comparison, a potential abnormality at the particular location of the body,
       wherein to determine the projection, the one or more processors are configured to:
          determine a common alignment reference for aligning the first set of images;
          align, according to the common alignment reference, a plurality of images from the first set of images; and
          determine, from the plurality of aligned images, the projection of alteration characteristics.

16. The system of claim 15, wherein to identify the potential abnormality, the one or more processors are configured to:
    determine an abnormality trend indicating an anticipated progression toward the potential abnormality or toward a worsening abnormality.

17. The system of claim 15, wherein to determine the projection, the one or more processors are configured to:
    identify a set of pre-implant images representing the particular location of the body;
    determine, based at least in part on the set of pre-implant images, baseline characteristics of the body of the patient; and
    determine, based at least in part on the baseline characteristics, the projection of alteration characteristics.

18. A non-transitory computer-readable storage medium having stored thereon instructions that, when executed, cause one or more processors to at least:

identify a first set of images that represent a particular location of a body of a patient in which at least one component of an implantable medical device (IMD) coincides;
determine, from the first set of images, a projection of alteration characteristics of the particular location of the body projected over time, wherein the projection of alteration characteristics includes a projection of healing over time to a future time to indicate that a particular alteration should occur at the future time;
identify a second set of images that represent the particular location of the body;
determine, from the second set of images, a second set of alteration characteristics;
compare the second set of alteration characteristics to the projection;
identify, based at least in part on the comparison, a potential abnormality at the particular location of the body; and
in response to determining the potential abnormality, transmit the first set of images and the second set of images to a device of one or more health care professionals (HCPs) over a computing network.

19. A method of imaging a body of a patient of an implantable medical device (IMD), the method comprising:
identifying, via processing circuitry of a computing device, a first set of images that represent a particular location of the body in which at least one component of the IMD coincides;
determining, from the first set of images, a projection of alteration characteristics of the particular location of the body projected over time;
identifying, via the processing circuitry, a second set of images that represent the particular location of the body at a progression interval that follows in time the first set of images;
determining, from the second set of images, a second set of alteration characteristics;
comparing, via the processing circuitry, the second set of alteration characteristics to the projection; and
identifying, based at least in part on the comparison, a potential abnormality at the particular location of the body,
wherein the first set of images comprise at least a first image and a second image captured at successive time intervals, wherein the successive time intervals are spaced apart in time by a first duration of time, and
wherein the second set of images comprises a third image captured at a check-in time that follows in time a first interval of the successive time intervals by a second duration of time, wherein the second duration of time is greater than the first duration of time.

20. A method of imaging a body of a patient of an implantable medical device (IMD), the method comprising:
identifying, via processing circuitry of a computing device, a first set of images that represent a particular location of the body in which at least one component of the IMD coincides;
determining, from the first set of images, a projection of alteration characteristics of the particular location of the body projected over time, wherein the projection of alteration characteristics includes a projection of healing over time to a future time to indicate that a particular alteration should occur at the future time;
identifying, via the processing circuitry, a second set of images that represent the particular location of the body at a progression interval that follows in time the first set of images;
determining, from the second set of images, a second set of alteration characteristics;
comparing, via the processing circuitry, the second set of alteration characteristics to the projection; and
identifying, based at least in part on the comparison, a potential abnormality at the particular location of the body,
wherein determining the projection comprises:
determining, via the processing circuitry of the computing device, a set of pre-implant images representing the particular location of the body prior to implantation;
determining, from the set of pre-implant images, baseline characteristics of the body of the patient prior to the implantation; and
determining, based at least in part on the baseline characteristics, the projection of alteration characteristics.

21. A method of imaging a body of a patient of an implantable medical device (IMD), the method comprising:
identifying, via processing circuitry of a computing device, a first set of images that represent a particular location of the body in which at least one component of the IMD coincides;
determining, from the first set of images, a projection of alteration characteristics of the particular location of the body projected over time, wherein the projection of alteration characteristics includes a projection of healing over time to a future time to indicate that a particular alteration should occur at the future time;
identifying, via the processing circuitry, a second set of images that represent the particular location of the body at a progression interval that follows in time the first set of images;
determining, from the second set of images, a second set of alteration characteristics;
comparing, via the processing circuitry, the second set of alteration characteristics to the projection;
identifying, based at least in part on the comparison, a potential abnormality at the particular location of the body; and
in response to determining the potential abnormality, transmitting, via communication circuitry of the computing device, the first set of images and the second set of images to a device of one or more health care professionals (HCPs) over a computing network.

22. A system for imaging a body of a patient of an implantable medical device (IMD), the system comprising:
a memory configured to store one or more frames of image data, the one or more frames representing at least a first set of images; and
one or more processors in communication with the memory, the one or more processors configured to:
identify the first set of images that represent a particular location of the body in which at least one component of the IMD coincides;
determine, from the first set of images, a projection of alteration characteristics of the particular location of the body projected over time, wherein the projection of alteration characteristics includes a projection of healing over time to a future time to indicate that a particular alteration should occur at the future time;

identify a second set of images that represent the particular location of the body at a progression interval relative to the first set of images;

determine, from the second set of images, a second set of alteration characteristics;

compare the second set of alteration characteristics to the projection; and identify, based at least in part on the comparison, a potential abnormality at the particular location of the body, wherein to determine the projection, the one or more processors are configured to:

identify a set of pre-implant images representing the particular location of the body;

determine, based at least in part on the set of pre-implant images, baseline characteristics of the body of the patient; and determine, based at least in part on the baseline characteristics, the projection of alteration characteristics.

* * * * *